United States Patent
Adair et al.

(10) Patent No.: US 10,350,245 B2
(45) Date of Patent: Jul. 16, 2019

(54) POINT-OF-CARE AND/OR PORTABLE PLATFORM FOR GENE THERAPY

(71) Applicant: Fred Hutchinson Cancer Research Center, Seattle, WA (US)

(72) Inventors: Jennifer E. Adair, Seattle, WA (US); Hans-Peter Kiem, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 56 days.

(21) Appl. No.: 15/545,555

(22) PCT Filed: Jan. 21, 2016

(86) PCT No.: PCT/US2016/014378
§ 371 (c)(1),
(2) Date: Jul. 21, 2017

(87) PCT Pub. No.: WO2016/118780
PCT Pub. Date: Jul. 28, 2016

(65) Prior Publication Data
US 2018/0169148 A1 Jun. 21, 2018

Related U.S. Application Data

(60) Provisional application No. 62/106,192, filed on Jan. 21, 2015.

(51) Int. Cl.
| | |
|---|---|
| *A61K 35/28* | (2015.01) |
| *A61P 35/00* | (2006.01) |
| *C12M 1/42* | (2006.01) |
| *C12N 15/867* | (2006.01) |
| *C12Q 1/68* | (2018.01) |

(52) U.S. Cl.
CPC .............. *A61K 35/28* (2013.01); *A61P 35/00* (2018.01); *C12M 35/02* (2013.01); *C12N 15/8673* (2013.01); *C12Q 1/68* (2013.01); *C12N 2740/16043* (2013.01)

(58) Field of Classification Search
CPC .................................................. A61K 35/28
See application file for complete search history.

(56) References Cited

U.S. PATENT DOCUMENTS

| | | |
|---|---|---|
| 5,676,646 A | 10/1997 | Hofmann et al. |
| 2003/0175964 A1 | 9/2003 | Martin et al. |
| 2009/0081770 A1 | 3/2009 | Srienc et al. |
| 2009/0220458 A1 | 9/2009 | Schaffer et al. |
| 2009/0233354 A1 | 9/2009 | Furcht et al. |
| 2010/0009424 A1 | 1/2010 | Forde et al. |
| 2010/0210989 A1 | 8/2010 | Macpherson et al. |
| 2010/0323403 A1 | 12/2010 | Kafri |
| 2012/0087901 A1 | 4/2012 | Nelson |
| 2012/0164118 A1 | 6/2012 | Trobridge et al. |
| 2013/0216506 A1 | 8/2013 | Discher et al. |
| 2014/0315311 A1* | 10/2014 | Miltenyi ................ C12N 15/85 435/455 |
| 2015/0011543 A1 | 1/2015 | Sauvageau et al. |

FOREIGN PATENT DOCUMENTS

WO    WO2014099198    6/2014

OTHER PUBLICATIONS

N.H. Collins (Chapter 18 Product Review, Release, and Administration. In: Gee A. (eds) Cell Therapy. Springer, Boston, MA. Published online Jul. 31, 2009. pp. 215-228). (Year: 2009).*
Schlenke et al.(ISBT Science. May 2010. 136-140). (Year: 2010).*
Grupp et al. (N Engl J Med. Apr. 18, 2013; 368(16): 1509-1518). (Year: 2013).*
Haas et al. (Mol Ther. Jul. 2, 2000 (1): 71-80). (Year: 2000).*
Lantis et al. (Cancer Immunol Res. 2013; 1-11) (Year: 2013).*
Drake et al.(Hunnan CD34+ CD133+ Hematopoietic Stem Cells Cultured with Growth Factors Including Angptl5 Efficiently Engraft Adult NOD-SCID Il2rc2/2 (NSG) Mice. [2011] PLoS One 6(4): e18382. doi:10.1371/journal.pone.0018382). (Year: 2011).*
Deyle et al. (Journal of Virology, Sep. 2010, p. 9341-9349). (Year: 2010).*
Daniel-Johnson, et al., "How do I approach ABO-incompatible hematopoietic progenitor cell transplantation", Transfusion, vol. 51, 2011, pp. 1143-1149.
Donnenberg, et al., "Intra-operative preparation of autologous bone marrow-derived CD34-enriched cellular products for cardiac therapy", Cytotherapy, vol. 13, No. 4, 2011, pp. 441-448.
PCT Invitation to Pay Additional Fees dated Mar. 23, 2016 for International Application No. PCT/US16/14378.
PCT Search Report and Written Opinion dated Jun. 2, 2016 for International Application No. PCT/US16/14378.
Adair, et al., "Development and Validation of a Globally Portable Platform for Lentivirus Mediated Hematopoietic Stem Cell Gene Therapy", Molecular Therapy, vol. 23, No. Supplement 1, May 1, 2015, pp. S34-S35.
Adair, et al. "Semi-automated closed system manufacturing of lentivirus gene-modified haematopoietic stem cells for gene therapy", Nature Communications, Oct. 20, 2016, pp. 1-10.
The Partial Supplementary European Search Report dated Dec. 7, 2018 for European patent application No. 16740786.5, 18 pages.

* cited by examiner

*Primary Examiner* — Scott Long
(74) *Attorney, Agent, or Firm* — Lee & Hayes, PC; C. Rachal Winger

(57) ABSTRACT

A platform for ex vivo isolation, production, and formulation of genetically-modified cells is described. The platform utilizes a software-enabled point-of-care and/or portable device making gene therapy more widely available.

17 Claims, 23 Drawing Sheets
Specification includes a Sequence Listing.

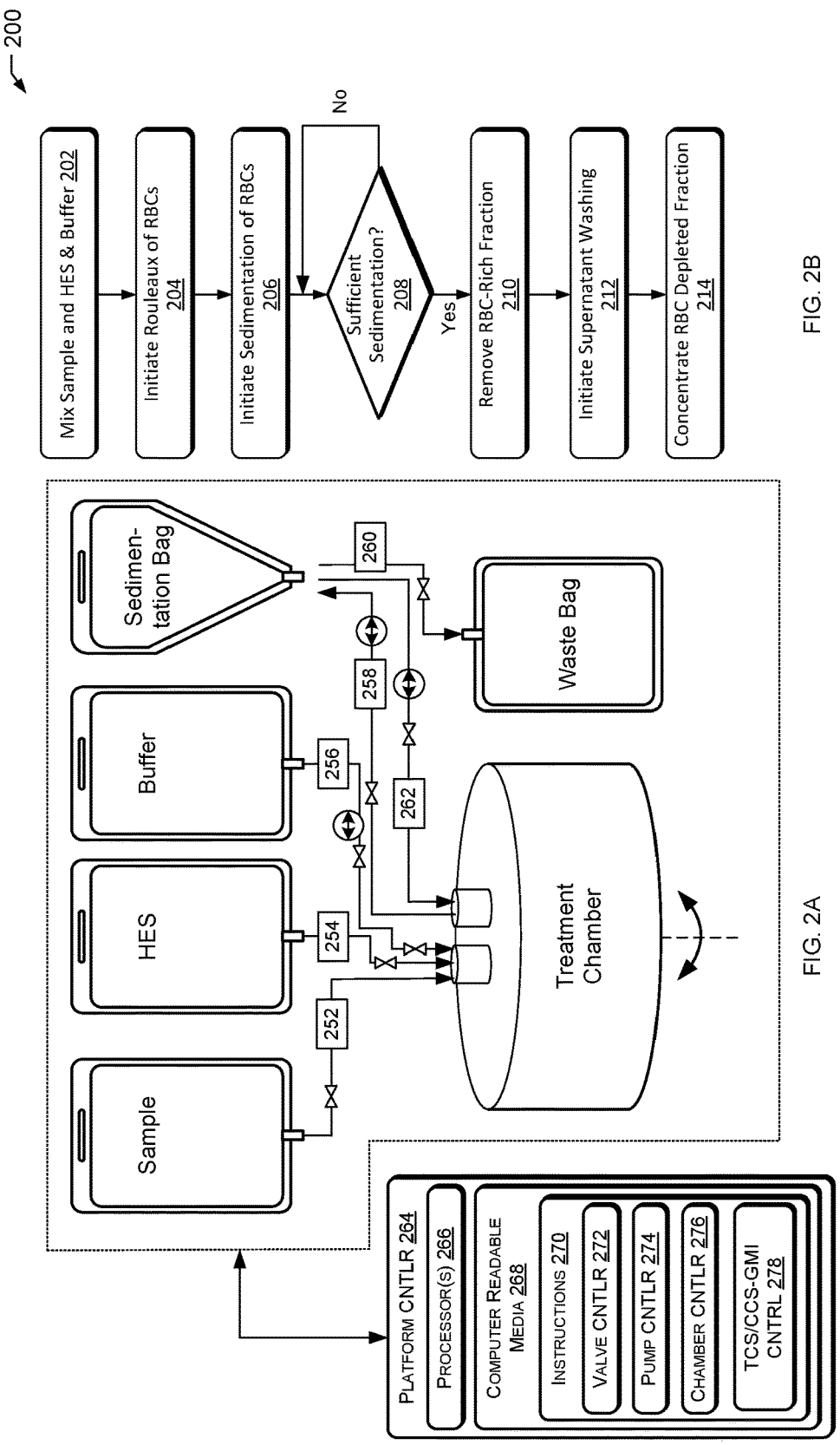

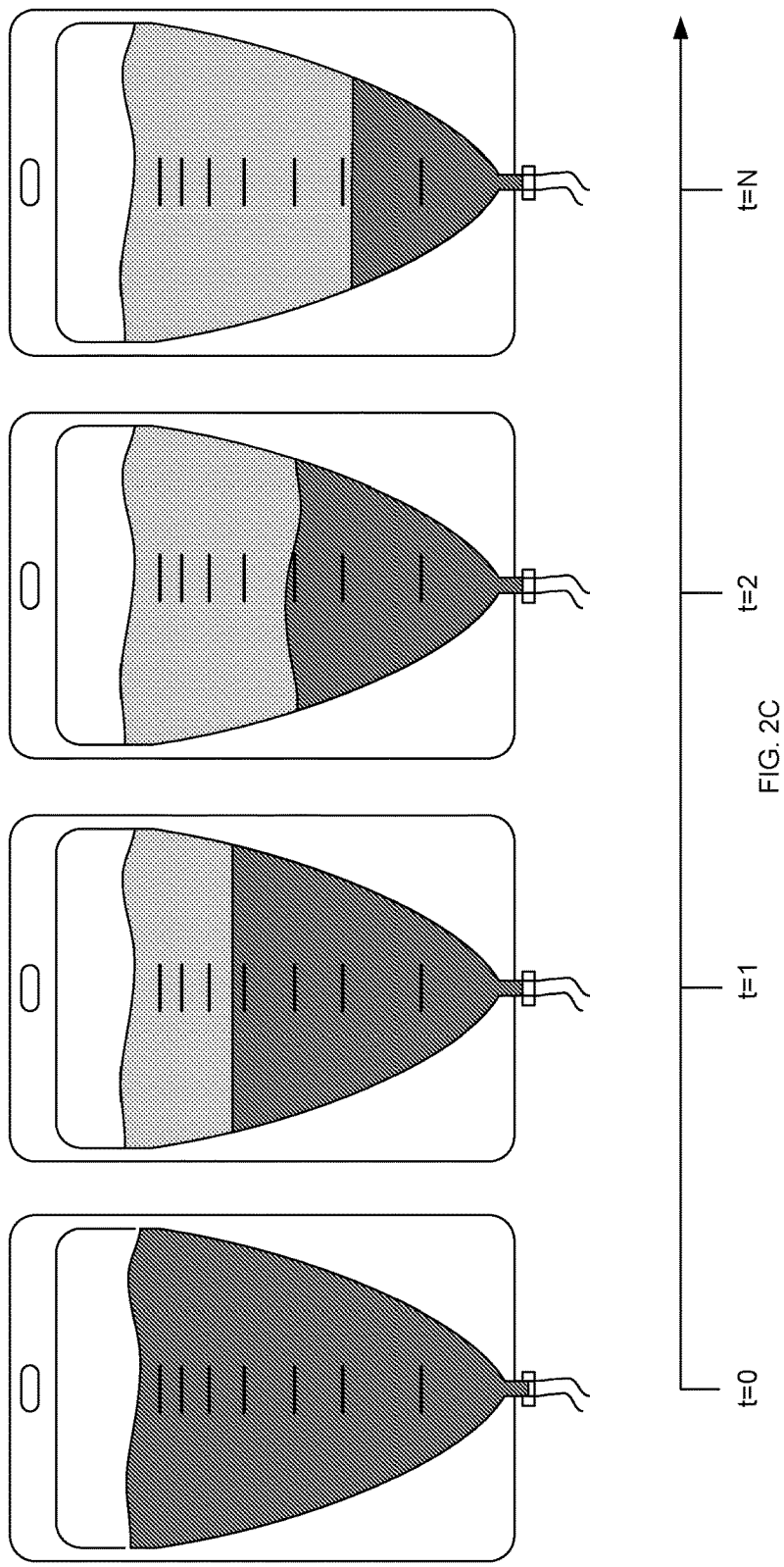

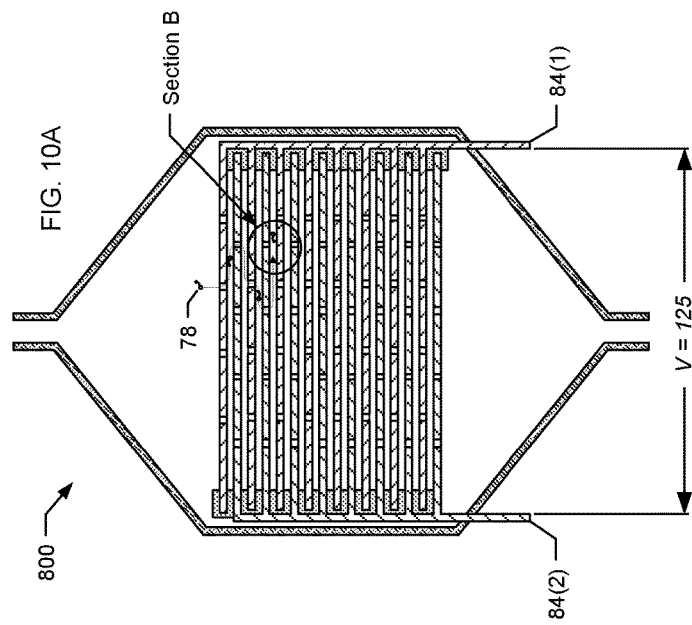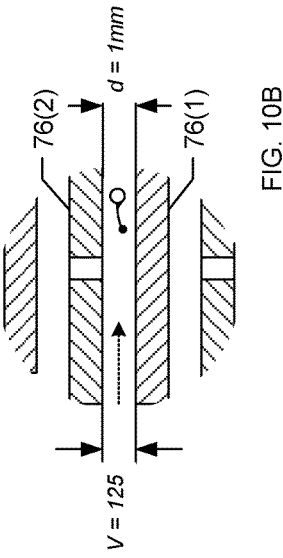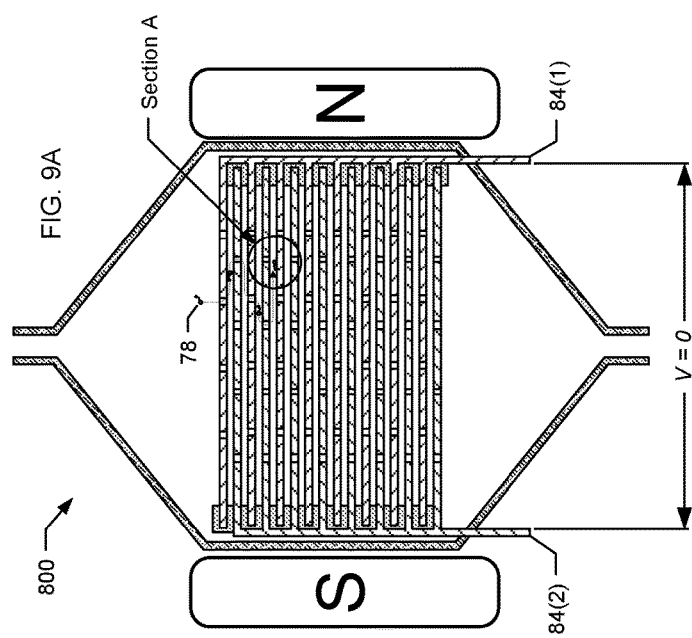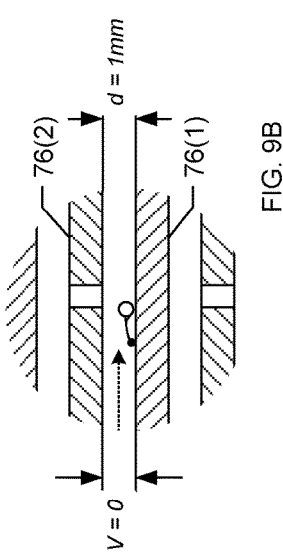

Dual anti-HIV (SIN)LV + P140K eGFP (SIN)LV + P140K

FIG. 18A
FIG. 18B
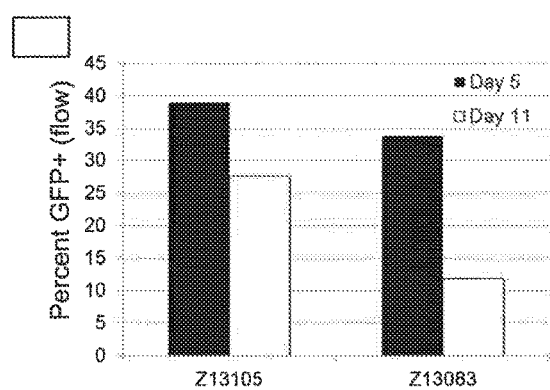
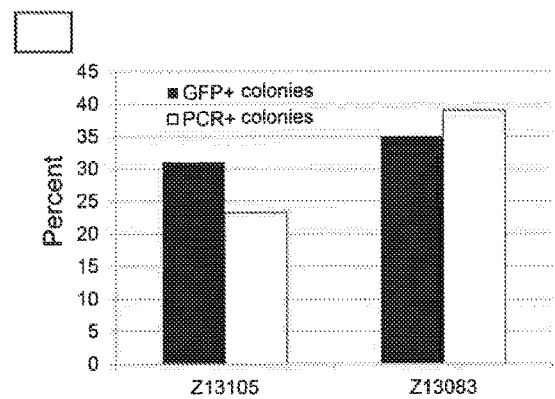

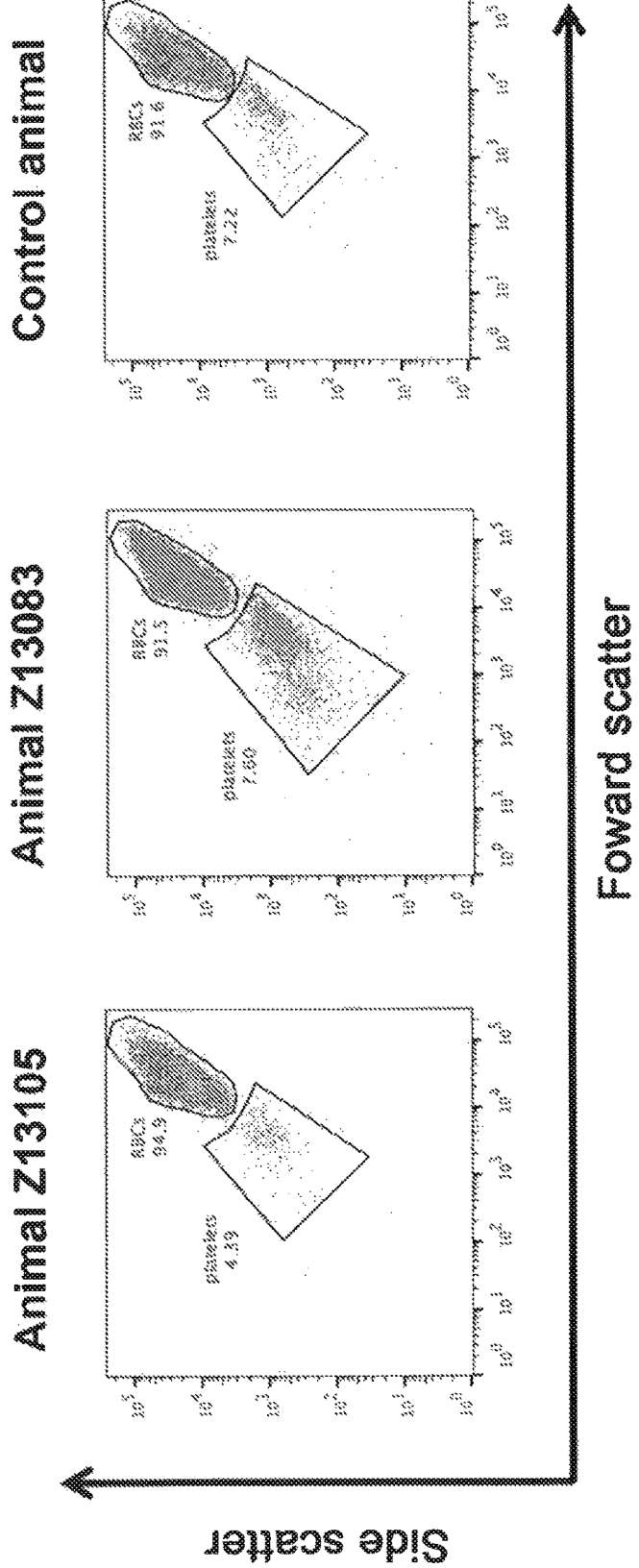

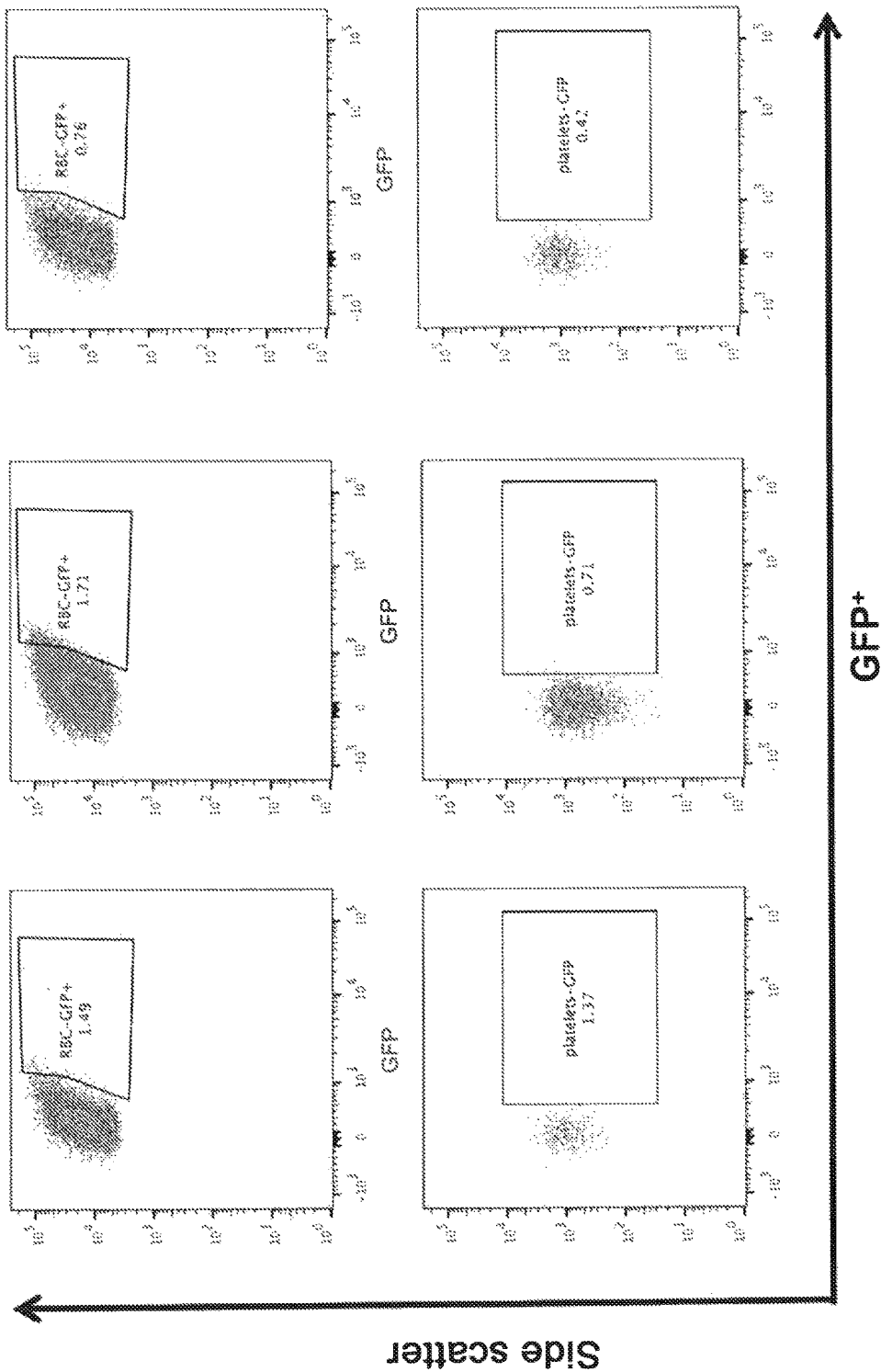

POINT-OF-CARE AND/OR PORTABLE PLATFORM FOR GENE THERAPY

CROSS-REFERENCE TO RELATED APPLICATIONS

This application is a U.S. National Phase Application based on International Patent Application No. PCT/US2016/014378 filed Jan. 21, 2016, which claims the benefit of U.S. Provisional Patent Application Number 62/106,192 filed Jan. 21, 2015, both of which are incorporated herein by reference in their entirety as if fully set forth herein.

STATEMENT REGARDING FEDERALLY SPONSORED RESEARCH OR DEVELOPMENT

This invention was made with government support under Al096111, and HL116217, awarded by the National Institutes of Health. The government has certain rights in the invention.

FIELD OF THE DISCLOSURE

The present disclosure provides a platform for ex vivo isolation, production, and formulation of gene-modified cells. The platform may execute software instructions upon a point-of-care and/or portable device to semi-autonomously perform genetic modifications on target cells with minimal user input, therefore making gene therapy more widely available.

BACKGROUND OF THE DISCLOSURE

The tremendous potential for gene therapy has been demonstrated in the last decade for many different diseases (reviewed in Ghosh, et al., Gene therapy for monogenic disorders of the bone marrow. *Br J Haematol.* (2015)). The simplest strategy proposed to distribute gene therapy involves direct in vivo gene modification. Efforts to achieve gene transfer in vivo in small and large animal models are underway (Burtner, et al., *Blood* 123, 3578-3584 (2014); Kay, et al., *Science* 262, 117-119 (1993); Ponder, et al., *Proc Natl Acad Sci USA* 99, 13102-13107 (2002); Ting-De Ravin, et al., *Blood* 107, 3091-3097 (2006); Frecha, et al., *Blood* 119, 1139-1150 (2012)), but it will likely be some time before this approach meets current safety and efficacy standards to permit clinical testing in subjects. Major hurdles include stringent evaluation of gene transfer to non-target cells balanced with achieving sufficient therapeutic gene transfer levels.

Ex vivo mediated gene transfer into target cells is one clinically applied method for gene therapy demonstrating efficacy to date. In stem cells, this approach allows for subsequent production of all blood cell types harboring the therapeutic genes for the lifetime of the patient. The isolation and genetic modification of CD34+ stem cells ex vivo provides two major benefits: elimination of gene transfer to non-target cells and reduced average amount of genetic modifiers, e.g. nucleic acid carriers, which in turn reduces costs associated with carrier production. To manufacture these products within current regulatory guidelines, however, typically requires complex centralized facilities adhering to current Good Manufacturing Practices (cGMP).

SUMMARY OF THE DISCLOSURE

The present disclosure provides a platform for ex vivo isolation, production, and formulation of gene modified cells. In particular embodiments, the platform utilizes a closed-loop sterile software-enabled portable and/or point-of-care device making gene therapy more widely available in a variety of research and therapeutic settings. At its most basic level, the device is a closed system device that includes material inputs (e.g., sample, buffers, gas) at least one treatment chamber with centrifugation and cell incubation capabilities, a closed tubing set, a pump, and a target cell selector. Controlling software enables the device to isolate, genetically-modify, and formulate target cells ex vivo, in particular embodiments, directly from a subject sample. The entire process can be completed within 30 hours with minimal to no user input. Also disclosed herein are kits including materials necessary or helpful to practice the methods and use the devices described herein.

As an overview, a sample may be obtained from a subject (e.g. a patient or a donor). Exemplary samples include peripheral blood, bone marrow, and/or apheresis and/or leukapheresis products. The sample may sterilely-enter a first treatment chamber of the device wherein the sample may undergo processing. During processing, various non-target sample components may be removed from the sample. For example, one or both of red blood cells (RBCs) or platelets (thrombocytes) may be separated from the target cells and removed from the sample.

Target cells may then be prepared for further isolation within the first treatment chamber. For example, preparing the target cells may include associating them with one or more labeling agents, e.g. directly-conjugated immunomagnetic beads, in the first treatment chamber. Furthermore, a particular "incubation" environment may be maintained within the first treatment chamber in order to facilitate association of labeling agent(s) with the target cells and/or the first treatment chamber may be operated to agitate the sample and labeling agent(s) which may induce further association.

In particular embodiments, following target cell preparation, the sample may be transferred from the first treatment chamber through a target cell selector/isolator. In particular embodiments, the isolated/selected target cells may remain in the target cell selector/isolator and be exposed to a genetic modifier (e.g., a nucleic acid, DNA, RNA, proteins, viral vectors, or other tools and modalities described elsewhere herein). In particular embodiments, the target cell selector/isolator includes electroporation capabilities to facilitate the introduction of genetic modifiers into the target cells. In particular embodiments, the isolated/selected cells may be returned to the first treatment chamber (or a supplemental treatment chamber) and can be exposed to a genetic modifier. The treatment chamber (first and/or supplemental) may once again be maintained at an incubation environment, e.g. by maintaining a temperature or introducing a gas mixture. Moreover, the genetic modifier may be added in stages to improve gene-modification. Finally, the gene-modified target cells are purified and formulated for administration to a subject. It should be appreciated that although the foregoing discussion may refer to some exemplary embodiments as utilizing a nucleic acid as the genetic modifier(s), the use of any other type of genetic modifier whether currently known or subsequently developed is also within the scope of the present disclosure.

As indicated previously, each of the described steps, among others described in more detail elsewhere herein, can be performed within one point-of-care and/or portable closed-loop, sterile software-enabled device within 30 hours of sample receipt.

BRIEF DESCRIPTION OF THE FIGURES

The detailed description is described with reference to the accompanying figures. In the figures, the same reference numbers in different figures indicate similar or identical items.

FIG. 2A shows a schematic diagram of an exemplary system for depleting red blood cells (RBCs) from a sample. FIG. 2B is a flow chart of an exemplary method for depleting RBCs using the exemplary system of FIG. 2A. FIG. 2C illustrates a funnel shaped sedimentation bag with a sample having undergoing RBC Rouleau. As illustrated the RBCs concentrate into an increasingly dense sediment as time progresses.

FIGS. 9A-9B illustrate the CCS-GMI in a magnetized state during the performance of Magnetic Activated Cell Sorting (MACS).

FIGS. 10A-B illustrate the CCS-GMI in an electrified state during the performance of electroporation.

(FIG. 12A) The clinical-grade LV encoding two anti-HIV transgenes (shCCR5 and C46), as well as a synthetic 06-benzylguanine resistant MGMT mutant P140K transgene. (FIG. 12B) The enhanced green fluorescent protein (eGFP) and synthetic $O_6$-benzylguanine resistant MGMT mutant P140K transgene-encoding LV used for gene transfer and in vivo tracking in nonhuman primates. Both vectors lack the X' open reading frame present in the Woodchuck hepatitis virus post-transcriptional element (wpre). AmpR (ampicilin resistance gene); RSV (Rous Sarcoma Virus); PSI (encapsidation sequence); RRE (rev response element); cPPT (central polypurine tract); SFFV (Spleen Focus-forming Virus); PGK (phosphoglycerate kinase); LTR (long terminal repeat).

(FIG. 15A) Human cell engraftment levels in peripheral blood of individual adult NSG mice receiving LV transduced CD34$^+$ cells at various time points post injection. At time of sacrifice 12 weeks after injection, bone marrow was analyzed for both total human cell content and human CD34$^+$ cell levels (FIG. 15B). (FIG. 15C) The level of gene modified human cells in both the peripheral blood and bone marrow was determined by quantitative PCR.

FIGS. 18A-B. Gene marking in growth factor primed bone marrow nonhuman primate CD34+ cells following automated transduction. Following semi-automated transduction and harvest, aliquots of the final cell product for infusion into myeloablated monkeys were cultured in liquid media including recombinant human growth factors GCSF, SCF, TPO, Flt3-L, IL-3 and IL-6 for subsequent flow cytometry (FIG. 18A), or in methylcellulose media containing the same recombinant human growth factors for colony forming assay (FIG. 18B) and subsequent flow cytometry or PCR reactivity.

FIGS. 19A-B. Sustainable hematopoiesis and engraftment of lentivirus gene modified CD34$^+$ cells in vivo in the nonhuman primate following point-of-care and/or portable manufacturing. Two animals (Z13105 and Z13083) received autologous, lentivirus gene modified CD34+ cells produced under semi-automated conditions following myeloablative TBI. (FIG. 19A) Graphs depict hematopoietic recovery by absolute neutrophil counts (open circles; ○) and platelet counts (closed circles; ●) on the primary y-axis, engraftment of gene modified peripheral blood granulocytes (closed gray squares; ■) and lymphocytes (open gray squares; □) and measured tacrolimus levels in serum (closed diamonds; ♦) on the secondary y-axis as a function of time after transplantation (x-axis). (FIG. 19B) Percent of gene modified (eGFP+) lymphocytes expressing CD3, and the percentage of eGFP+/CD3+ cells expressing CD4 and/or CD8 observed in peripheral blood (y-axis) over time after transplant (x-axis).

FIG. 20. Transgene expression in nonhuman primate red blood cells and platelets in vivo following automated transduction. At 258 and 222 days post-transplant for animals Z13105 and Z13083, respectively, flow cytometry revealed GFP transgene expression in RBC and platelets relative to a control (non-transplanted) animal (lower panel). Upper panel represents scatter properties of RBC and platelets for each animal. Gates were established using the control animal.

DETAILED DESCRIPTION

Figure 1:
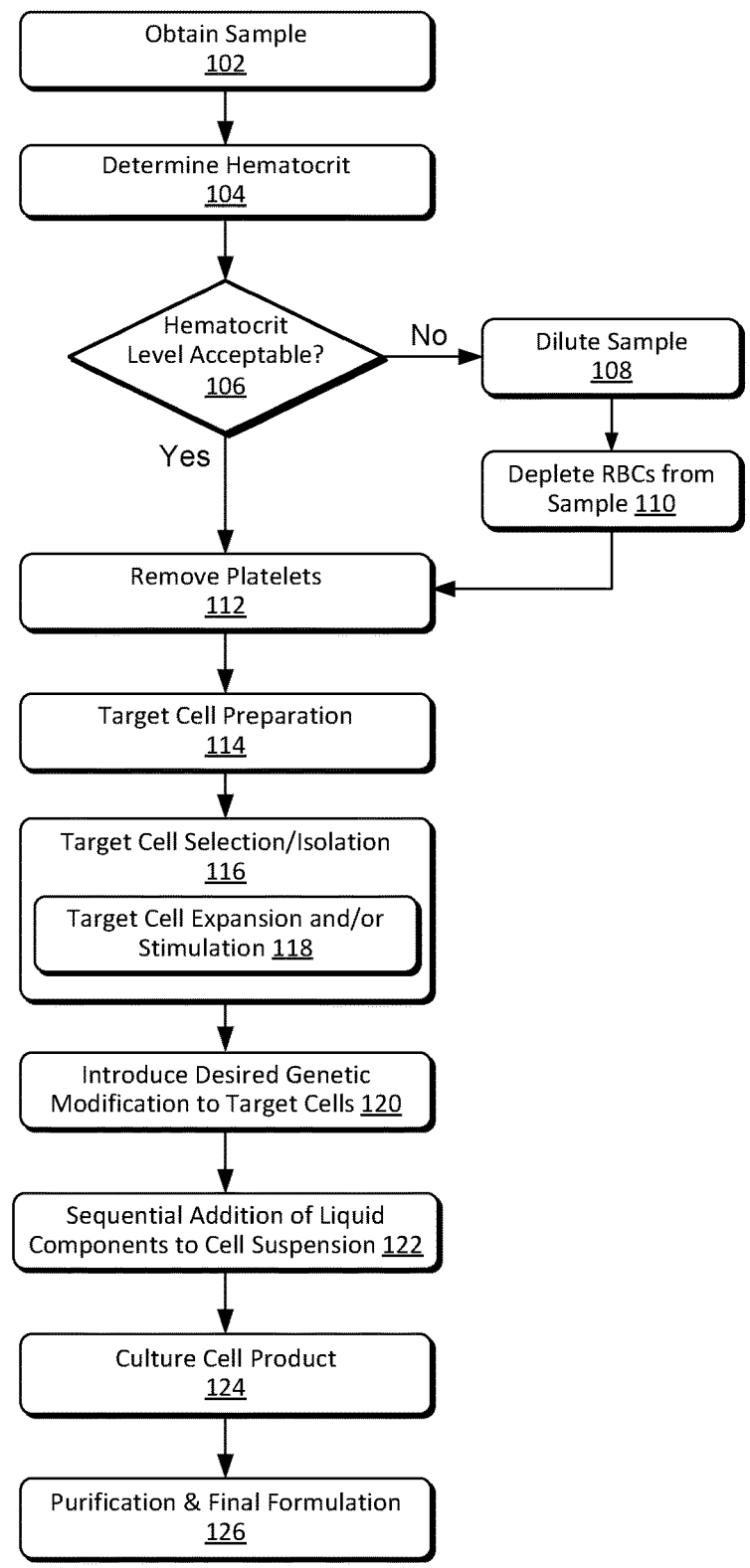
FIG. 1 is a flow chart of an exemplary method for genetically modifying target cells using a point-of-care and/or portable gene therapy device configured with associated executable instructions in accordance with an exemplary embodiment of systems and methods disclosed herein.

The tremendous potential for gene therapy has been demonstrated in the last decade for many different diseases. For examples using hematopoietic stem and progenitor (CD34+) cells, see Ghosh, et al., Gene therapy for monogenic disorders of the bone marrow. Br J Haematol, (2015). More particularly, lentivirus mediated gene transfer into CD34+ stem and progenitor cells (HSPCs) has now demonstrated clinical success in a variety of diseases including primary inherited immunodeficiencies, hemoglobinopathies, lysosomal storage disorders and cancer. Current gene therapy clinical trials are also underway to treat sickle cell anemia and infectious diseases such as HIV.

The simplest strategy proposed to distribute gene therapy involves direct in vivo gene modification. Efforts to achieve gene transfer in vivo in small and large animal models are underway (Burtner, et al., Blood 123, 3578-3584 (2014); Kay, et al., Science 262, 117-119 (1993); Ponder, et al., Proc Natl Acad Sci USA 99, 13102-13107 (2002); Ting-De Ravin, et al., Blood 107, 3091-3097 (2006); Frecha, et al., Blood 119, 1139-1150 (2012)), but it will likely be some time before this approach meets current safety and efficacy standards to permit clinical testing in patients. Major hurdles in this field include stringent evaluation of gene transfer to non-target cells balanced with achieving sufficient therapeutic gene transfer levels to target cells of interest.

Ex vivo lentivirus (LV)-mediated gene transfer into CD34+ cells is the most clinically applied method for stem cell gene therapy demonstrating efficacy to date. This approach allows for subsequent production of all blood cell types harboring the therapeutic gene for the lifetime of the patient. The isolation and genetic modification of CD34+ cells ex vivo provides two major benefits: elimination of gene transfer to non-target cells and reduced average used amount of genetic modifiers, such as for example LV particles, which in turn reduces costs associated with vector production. To manufacture these products within current regulatory guidelines, however, typically requires complex centralized facilities adhering to current Good Manufacturing Practices (cGMP) facility with trained staff, limiting this treatment to only highly developed countries and facilities within them capable of supporting GMP infrastructure.

Manufactured in accordance with Current Good Manufacturing Practices means that the formulation prepared for administration is sufficiently safe to permit administration to a human subject under controlling regulations and government authorizations. Generally, the controlling regulations and authorizations will dictate that the formulation meet pre-approved acceptance criteria regarding identity, strength, quality and purity. Acceptance criteria include numerical limits, ranges, or other suitable measures of test results used to determine whether a formulation meets the Current Good Manufacturing Practices. A specification sets forth the analytical procedures that are used to test conformance with the acceptance criteria. Formulations can be assessed in batches. A batch is a specific quantity of a formulation tested to ensure compliance with acceptance criteria.

In particular embodiments, to confirm compliance with Current Good Manufacturing Practices, the following procedures are performed:

1. Final Release Sterility Testing (bacterial, fungal and yeast) per USP<71>. Preparation of testing is conducted in controlled cleanrooms and includes 14-day incubation and compendial sterility by direct inoculation, membrane filtration and swab.
2. Final Product Viability Testing is conducted in a controlled cleanroom by trypan blue exclusion and 7AAD staining by flow cytometry.
3. Cell enumeration is conducted on controlled labs by manual hemacytometer count, and/or automated hemacytometer count, and/or automated blood cell counter.
4. Testing for *mycoplasma* is conducted by a culture based method and/or a rapid PCR test and/or a non-rapid PCR test.
5. Testing for endotoxin is performed by limulus amebocyte lysate assay.

In particular embodiments, a rapid gram stain may be performed.

Other assessment procedures can include expression of target gene(s) for genetic modification, colony-forming capacity or other in vitro test specific to cell fitness such as cell surface marker expression, cell expansion and/or engraftment or persistence into xenotransplant animal models. Vector copy number assays can be performed when retroviral vectors are applied, deep sequencing of cellular DNA when gene editing approaches are applied, and/or sequencing of loci of integration when integrating retroviral vectors are applied. Tests of function specific to the target genetic modification and/or disease setting can also be performed. For example, FA cells are very sensitive to mitomycin C treatment. After gene transfer of a functional FA gene, the genetically modified cells can be exposed to mitomycin C and a determination of whether or not the sensitivity has been reduced or eliminated can be made.

In particular embodiments, Release Testing is performed to confirm compliance with Current Good Manufacturing Practices. In particular embodiments, Release Testing includes:

| Parameter | Method | Specification |
|---|---|---|
| Microbial Contamination | Gram Stain | No Microbial Organisms Observed |
| Endotoxin | LAL Lysate Kinetic Turbidimetric | <5 EU/kg |
| Viability | Trypan Blue Exclusion | ≥70% |

In particular embodiments, Release Testing includes:

| Parameter | Method | Specification |
|---|---|---|
| Sterility | USP <71> Sterility Tests | No Growth |
| Mycoplasma | qPCR | Negative for mycoplasma species |
| Transduction Efficiency | PCR | Value Reported |
| Replication Competent Virus | Per Indiana University School of Medicine | Negative for replication competent virus |
| Colony Forming Unit | PCR | Value Reported |

In particular embodiments, Release Testing includes:

| Test | Required Result |
|---|---|
| Gram Stain | Negative |
| 3 Day Sterility | Negative |
| 14 Day Sterilitly | Negative |
| Mycoplasma | Negative |
| Endotoxin | ≤0.5 EU/ml |
| Cell Viability by Trypan Blue Dye Exclusion | ≥70% |

The present disclosure provides a platform for ex vivo isolation, production, and formulation of gene modified cells. The platform utilizes a software-enabled point-of-care and/or portable device making gene therapy more widely available in a variety of research and therapeutic settings. In particular embodiments, a point-of-care device is one that resides within a facility (e.g., hospital or doctor's office); room (e.g., subject room) or area (e.g. tent) where a subject (e.g., patient) is treated. In particular embodiments, a portable device is one that can be transported from one area to another using a standard laboratory cart (e.g a cart with dimensions 32"L×32"W×36"H) in a facility or room or using a motorized vehicle around an area. In particular embodiments, a portable device is one that weighs less than 250 lbs., less than 200 lbs., less than 150 lbs., or less than 100 lbs. In particular embodiments, a portable device is one with dimensions of less than 100 cm (w); less than 60 cm (d); and less than 80 cm, 60 cm, or 50 cm (h).

At its most basic level, the device is a closed system device that includes material inputs (e.g., sample, buffers, gas) at least one treatment chamber with centrifugation and cell incubation capabilities, a closed tubing set, a pump, and a target cell selector. Controlling software enables the device to isolate, genetically-modify, and formulate target cells ex vivo, in particular embodiments, directly from a subject sample. In particular embodiments, the entire process can be completed within 30 hours, within 25 hours or within 20 hours with minimal to no user input. In particular embodiments, the entire process is completed within 72 hours or within 64 hours. In particular embodiments, minimal user input means that between sample input into the device and recovery of genetically-modified cells formulated for administration to a subject, the user interacts with the device no more than 20, 15, 10, or 5 times and/or interacts with the device for no more than 12 hours, 10 hours, 8 hours, 5 hours, 4 hours, or 3 hours. Exemplary interactions from a user can include one or more of: connecting a sterile tubing set; verifying maintenance of a closed, sterile system; determining that a stage should be repeated (e.g., sedimentation); verifying successful completion of a stage; allowing a new stage to begin following a process quality check; providing reagents for device input; and determining and/or calculating volumes for addition or removal. Interactions can be timed by, following sample receipt, the amount of time the user is preparing for or actually interacting with the device.

In particular embodiments, one or more rounds of selection result in isolation of target cells. Therefore, the combined phrase selection/isolation is used. One or more rounds of purification of genetically-modified target cells results in formulation. Therefore, the disclosure refers to purification and formulation. This explanation is provided to clarify that the recited terms do not necessarily represent separate processes, but can instead represent a difference in degree (selection→isolation; purification→formulation).

Processes disclosed herein may be illustrated as a collection of blocks in a logical flow graph, which represent a sequence of operations that can be implemented in hardware, software, human input, or a combination thereof. It should also be appreciated that the logical flow paths depicted are not to be construed to indicate that the described process steps need be performed in any particular order unless otherwise expressly and unambiguously stated as such elsewhere herein. Stated alternatively, the logical flow paths herein represent but a few of many possible orders which the steps may be performed. Furthermore, particular operations within the figures of the present disclosure are disclosed as being optional operations which may, or may not be performed in any particular embodiment. Moreover, any component and/or operation of a particular figure may be practiced in conjunction with (or absent from for that matter) from any other component and/or operation of a particular figure. In the context of software, the blocks represent computer-executable instructions stored on one or more computer-readable storage media (e.g., machine readable storage media) that, when executed by one or more hardware processors, cause mechanical components of a point-of-care and/or portable target cell gene therapy device to perform the recited operations. Generally, computer-executable instructions include routines, programs, objects, components, data structures, and the like that perform particular functions or implement particular abstract data types. Embodiments may be provided as a computer program product including a non-transitory computer-readable storage medium having stored thereon instructions (in compressed or uncompressed form) that may be used to program a computer (or other electronic device) to perform processes or methods described herein. The computer-readable storage medium may include, but is not limited to, hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of media/computer-readable medium suitable for storing electronic instructions. Although the computer-executable instructions and/or software disclosed herein may be readable and/or executable by a general purpose computer (as essentially any software may be), the performance of target cell separation and/or genetic modification in accordance with various embodiments disclosed herein utilize a purpose computer which is uniquely configured to transform/separate the sample and/or genetically modify the target cells. Moreover, the performance of target cell separation and/or genetic modification in accordance with the present disclosure represents a great improvement upon traditional methods of performing gene modification. For example, particular embodiments disclosed herein greatly reduce the risk of sample contamination by performing an entire gene modification protocol from sample insertion to final product formulation within a single closed circuit system, greatly reduce dependencies on immovable medical facilities, reduces the time required to conduct a gene modification protocol, among other benefits that one of skill in the art will recognize based on a review of the present disclosure.

FIG. 1 provides a flow chart of an exemplary method 100 for genetically modifying target cells using a point-of-care and/or portable device (POCD) configured with computer-executable instructions. At block 102, a sample is obtained which includes target cells (e.g., one or more type of cells which can be genetically modified and used for treating a subject). In particular embodiments, target cells include hematopoietic stem cells and/or hematopoietic progenitor cells (HSPC). HSPC can be chosen for genetic therapies in part due to their ability to self-renew and/or differentiate into (i) myeloid progenitor cells which ultimately give rise to monocytes and macrophages, neutrophils, basophils, eosinophils, erythrocytes, megakaryocytes/platelets, or dendritic cells; or (ii) lymphoid progenitor cells which ultimately give rise to T-cells, B-cells, and lymphocyte-like cells called natural killer cells (NK-cells). For a general discussion of hematopoiesis and HSPC differentiation, see Chapter 17, Differentiated Cells and the Maintenance of Tissues, Alberts et al., 1989, Molecular Biology of the Cell, 2nd Ed., Garland Publishing, New York, N.Y.; Chapter 2 of Regenerative Medicine, Department of Health and Human Services, Aug. 5, 2006, and Chapter 5 of Hematopoietic Stem Cells, 2009, Stem Cell Information, Department of Health and Human Services.

HSPC can be positive for a specific marker expressed in increased levels on HSPC relative to other types of hematopoietic cells. For example, such markers include CD34, CD43, CD45RO, CD45RA, CD49f, CD59, CD90, CD109, CD117, CD133, CD166, HLA DR, or a combination thereof. Also, the HSPC can be negative for an expressed marker relative to other types of hematopoietic cells. For example, such markers include Lin, CD38, or a combination thereof. Preferably, the HSPC are CD34+ cells or cell fractions depleted of lineage-specific markers including CD3, CD4, CD8, CD13, CD14, CD15, CD16, CD19, CD20, CD56 or any combination thereof.

Sources of HSPC include cord blood, peripheral blood and bone marrow, therefore, these sources are exemplary samples to be obtained at block 102. Methods regarding collection, anti-coagulation and processing, etc. of blood samples are well known in the art. See, for example, Alsever et al., 1941, N.Y. St. J. Med. 41:126; De Gowin, et al., 1940, J. Am. Med. Ass. 114:850; Smith, et al., 1959, J. Thorac. Cardiovasc. Surg. 38:573; Rous and Turner, 1916, J. Exp. Med. 23:219; and Hum, 1968, Storage of Blood, Academic Press, New York, pp. 26-160.

HSPC in peripheral blood are preferably mobilized prior to collection. Peripheral blood HSPC can be mobilized by any method known in the art. Peripheral blood HSPC can be mobilized by treating the subject with any agent(s), described herein or known in the art, that increase the number of HSPC circulating in the peripheral blood of the subject. For example, in particular embodiments, peripheral blood is mobilized by treating the subject with one or more cytokines or growth factors (e.g., G-CSF, kit ligand (KL), IL-I, IL-7, IL-8, IL-11, Flt3 ligand, SCF, thrombopoietin, or GM-CSF (such as sargramostim)). Different types of G-CSF that can be used in the methods for mobilization of peripheral blood include filgrastim and longer acting G-CSF-pegfilgrastim. In particular embodiments, peripheral blood is mobilized by treating the subject with one or more chemokines (e.g., macrophage inflammatory protein-1α (MIP1α/CCL3)), chemokine receptor ligands (e.g., chemokine receptor 2 ligands GROβ and GROβ$_{A4}$), chemokine receptor analogs (e.g., stromal cell derived factor-1α (SDF-1α) protein analogs such as CTCE-0021, CTCE-0214, or SDF-1α such as Met-SDF-Iβ), or chemokine receptor antagonists (e.g., chemokine (C—X—C motif) receptor 4 (CXCR4) antagonists such as AMD3100). In particular embodiments, peripheral blood is mobilized by treating the subject with one or more anti-integrin signaling agents (e.g., function blocking anti-very late antigen 4 (VLA-4) antibody, or anti-vascular cell adhesion molecule 1 (VCAM-1)). In particular embodiments, peripheral blood is mobilized by treating the subject with one or more cytotoxic drugs such as cyclophosphamide, etoposide or paclitaxel. In particular embodiments, peripheral blood can be mobilized by administering to a subject one or more of the agents listed above for a certain period of time. For example, the subject can be treated with one or more agents (e.g., G-CSF) via injection (e.g., subcutaneous, intravenous or intraperitoneal), once daily or twice daily, for 1, 2, 3, 4, 5, 6, 7, 8, 9, 10, 11, 12, 13 or 14 days prior to collection of HSPC. In specific embodiments, HSPC are collected within 1, 2, 3, 4, 5, 6, 7, 8, 12, 14, 16, 18, 20 or 24 hours after the last dose of an agent used for mobilization of HSPC into peripheral blood. In particular embodiments, HSPC are mobilized by treating the subject with two or more different types of agents described above or known in the art, such as a growth factor (e.g., G-CSF) and a chemokine receptor antagonist (e.g., CXCR4 receptor antagonist such as AMD3100), or a growth factor (e.g., G-CSF or KL) and an anti-integrin agent (e.g., function blocking VLA-4 antibody). In particular embodiments, different types of mobilizing agents are administered concurrently or sequentially. For additional information regarding methods of mobilization of peripheral blood see, e.g., Craddock et al., 1997, Blood 90(12):4779-4788; Jin et al., 2008, Journal of Translational Medicine 6:39; Pelus, 2008, Curr. Opin. Hematol. 15(4):285-292;

Papayannopoulou et al., 1998, Blood 91(7):2231-2239; Tricot et al., 2008, Haematologica 93(11):1739-1742; and Weaver et al., 2001, Bone Marrow Transplantation 27(2): S23-S29).

HSPC from peripheral blood can be collected from the blood through a syringe or catheter inserted into a subject's vein. For example, the peripheral blood can be collected using an apheresis machine. Blood flows from the vein through the catheter into an apheresis machine, which separates the white blood cells, including HSPC from the rest of the blood and then returns the remainder of the blood to the subject's body. Apheresis can be performed for several days (e.g., 1 to 5 days) until enough HSPC have been collected.

HSPC from bone marrow can be obtained, e.g., directly from bone marrow from the posterior iliac crest by needle aspiration (see, e.g., Kodo et al., 1984, J. Clin Invest. 73:1377-1384), or from the blood following pre-treatment with cytokines (such as G-CSF and/or AMD3100) that induce cells to be released from the bone marrow compartment.

At block 104, a hematocrit level of the sample may be determined. The hematocrit level may be determined by centrifuging the sample within a treatment chamber, e.g. the treatment chamber illustrated in FIG. 2A, to separate RBCs of a sample into a layer such that the packed cell volume may be determined. It should be appreciated that the sample may be combined with an anticoagulant in order to assist with determining the hematocrit level and that such an anticoagulant may be added to the treatment chamber prior to or during centrifugation. Alternatively, the hematocrit level may be determined by measuring optical properties of the sample. For example, a spectrometer may be used to analyze the sample. It should be appreciated that any type of known spectroscopic methods of determining hematocrit level may be used such as, for example, Raman spectroscopy and/or light scattering techniques.

At decision block 106, a determination can be made as to whether the hematocrit level determined at block 104 is acceptable for purposes of performing an intended selection/isolation, production, and formulation method. In particular embodiments, a hematocrit level threshold is predetermined above which the sample undergoes a RBC depletion method. For example, in particular embodiments, samples with a hematocrit level greater than or equal to 25% automatically undergo a RBC depletion method. In general, an exemplary RBC depletion method may include diluting the sample at block 108 and then depleting RBCs from the sample at block 110.

Referring now to FIGS. 2A and 2B, another exemplary RBC depletion method 200 may include mixing the sample with an HES solution within the treatment chamber at block 202 and as indicated by arrow 252 which corresponds to a sample input and 254 which corresponds to a media input. Block 202 may also include adding a buffer solution to the treatment chamber as indicated by arrow 256 which corresponds to a buffer input. Specific amounts of HES and/or buffer to add at block 202 may be determined based on the initial volume of the sample and/or a maximum volume of the treatment chamber. For example, in particular embodiments if the sample has a hematocrit level above 25% it may be diluted with 20% volume HES and buffer (e.g. PBS/EDTA) up to a maximum volume of the treatment chamber, e.g. 300 mL.

At block 204, rouleau of the RBCs can be initiated. In particular embodiments, rouleau is initiated by performing slow centrifugation (e.g., 35-45×g or 40×g) within the treatment chamber. It should be appreciated that the intended g force, e.g. 35-45 g, can be calculated based on the rotational speed of the centrifuge (rpm) and the radius of rotation. At block 206, sedimentation of the RBCs is initiated by transferring the sample from the treatment chamber to a sedimentation bag as indicated by arrow 258. In particular embodiments, a determination is made at decision block 208 as to whether a sufficient amount of sedimentation has occurred. Such a determination may be made by receiving a user input from a user whom has visually examined the sedimentation bag and contents thereof. In particular embodiments, if sufficient sedimentation has not yet occurred then the method proceeds along the arrow labeled "No" and later returns to block 208. In contrast, if sufficient sedimentation has occurred the method may proceed to block 210 at which the RBC-Rich fraction of the blood sample, e.g. that fraction which has formed as sediment within the sedimentation bag, is removed from the sedimentation bag as indicated by arrow 260. In particular embodiments, the RBC-Fraction removal is performed in a stepwise fashion by user defined volumes until the desired RBC pellet size is reached. For example, with particular reference to FIG. 2C, a sample may be transferred to a funnel shaped sedimentation bag in which Rouleau and sedimentation is to occur. As time progresses from t=0 to t=N the RBC-Fraction forms an increasingly concentrated sediment/pellet. In particular embodiments, a funnel shaped sedimentation bag which includes volume demarcations (as illustrated in FIG. 2C) may be visually inspected once an appropriate amount of sedimentation has occurred and the user may enter a user defined volume corresponding to the RBC pellet which is then transferred from the sedimentation bag while the Target Cell Fraction remains in the sedimentation bag. It should be appreciated that the Target Cell fraction may include platelets or other blood components. In particular embodiments, the instructions 270 may include default amounts of time for sedimentation and default volumes to be removed at specific times, e.g. the instructions may be programed to remove a 50 mL or 75 mL or 100 mL 30 minutes after the sample is transferred to the sedimentation bag.

At block 212, the sample (e.g. the RBC Depleted fraction) is transferred back into the first treatment chamber as indicated by arrow 262 for supernatant washing. While the depicted use of the treatment chamber is preferred, in particular embodiments the POCD may include one or more supplemental treatment chambers for, for example, supernatant washing. Supernatant washing may remove any unwanted component of the sample such as, for example, residual HES from block 202. For example, buffer may be again added to the sample in the treatment chamber wherein centrifugation is performed to wash out residual HES. At block 214, the RBC Depleted fraction of the sample may be concentrated to a desired volume for subsequent processing. For example, the RBC Depleted fraction may undergo centrifugation to remove buffer while leaving the target cells in the treatment chamber. Block 214 may also optionally include aspiration.

For those particular embodiments disclosed herein which perform red blood cell (RBC) depletion, computer-executable instructions stored on one or more memories may be executed to cause one or more hardware components of a POCD to perform one or more steps described in relations to FIGS. 2A and 2B. Exemplary description of computer-executable instructions are denoted herein as SW1 and are described as follows in Table 1:

TABLE 1

Exemplary description of computer-executable RBC depletion instructions.

SW1 Description 1. RBC depletion of bone marrow or peripheral blood
SW1 Description 2. RBC depletion of bone marrow or peripheral blood. Starting sample at ≤25% HCT is mixed with HES and buffer depending on initial product volume. Each stage has a maximum volume and includes
rouleau induction, followed by transfer of product to a sedimentation bag. Following sedimentation, RBC-rich fraction removal is initiated until a selected RBC pellet size is reached. Following completion of RBC removal, supernatant washing is initiated to remove residual HES. The RBC depleted fraction remains in the device chamber for labeling.
SW1 Description 3. RBC depletion of bone marrow or peripheral blood. Starting bone sample at ≤25% HCT is mixed with 20% volume HES and PBS/EDTA buffer depending on initial product volume. Each stage has a maximum volume of 300 mL and includes a slow centrifugation step to initiate rouleau, followed by slow transfer of product to a sedimentation bag. Following a desired sedimentation time, the user is prompted to initiate RBC-rich fraction removal until the desired RBC pellet size is reached. Once the user confirms completion of RBC removal, the program automatically initiates supernatant washing to remove residual HES. Once washing is complete, the RBC depleted fraction is concentrated and remains in the device chamber.
SW1 Description 4 (also referred to herein as J1). This program is suitable for RBC depletion of bone marrow or peripheral blood of initial volume ≥ 10 mL. Starting bone sample at ≤25% HCT is mixed with 20% volume HES and Buffer (e.g. PBS/EDTA) in stages depending on initial product volume. Each stage has a maximum volume of 300 mL and includes a slow centrifugation step to initiate rouleau, followed by slow transfer of product to funneled sedimentation bag provided by the user. Minimum sedimentation wait is 30 minutes and can be prematurely terminated or extended infinitely by the user through a touchscreen interface. Following a desired sedimentation time, the user can be prompted to initiate RBC-rich fraction removal in a stepwise fashion by user-defined volumes until the desired RBC pellet size is reached. Once the user confirms completion of RBC removal, the program automatically initiates supernatant washing in Buffer (e.g. PBS/EDTA) to remove residual HES. Once washing is complete, the RBC depleted fraction is concentrated to the desired volume for bead labeling (90 mL) through a centrifugation and aspiration step and remains in the device chamber.

Referring now back to FIG. 1, the method 100 may further include removing platelets from the sample at block 112. In particular embodiments, platelet removal is beneficial because of platelet ability to react with and/or absorb certain types of reagents which may be introduced at later stages of the method 100. For example, platelets which remain in the sample may absorb one or more of protamine sulfate, rapamycin, polybrene, fibronectin fragment, prostaglandins or nonsteroidal anti-inflammatory drugs which may be added at one or more stages of method 100 for the benefit of the target cells as opposed to blood platelets.

At block 114, target cells may be prepared for selection/isolation. The preparation at block 114 will depend on the particular selection/isolation method that is chosen. Selection/isolation can be performed using any appropriate technique that is not unduly detrimental to the viability of the selected/isolated cells. Examples include magnetic separation using, for example, antibody-coated magnetic beads; fluorescence activated cell sorting (FACS; Williams et al., 1985, J. Immunol. 135:1004; Lu et al., 1986, Blood 68(1): 126-133); affinity chromatography; cytotoxic agents joined to a monoclonal antibody or used in conjunction with a monoclonal antibody, e.g., complement and cytotoxins; "panning" with antibody attached to a solid matrix, e.g., plate, or other convenient technique (Broxmeyer et al., 1984, J. Clin. Invest. 73:939-953), agglutination using a lectin such as soybean (Reisner et al., 1980, Proc. Natl. Acad. Sci. U.S.A. 77:1164); etc.

Figure 3B:
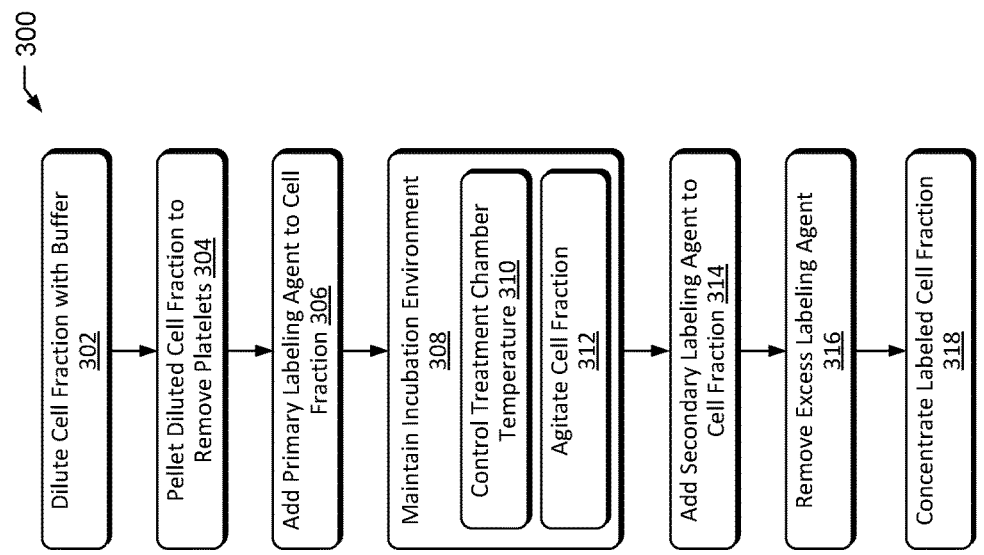
FIG. 3B is a flow chart of an exemplary method for preparing target cells using the exemplary system of FIG. 3A.
Figure 3A:
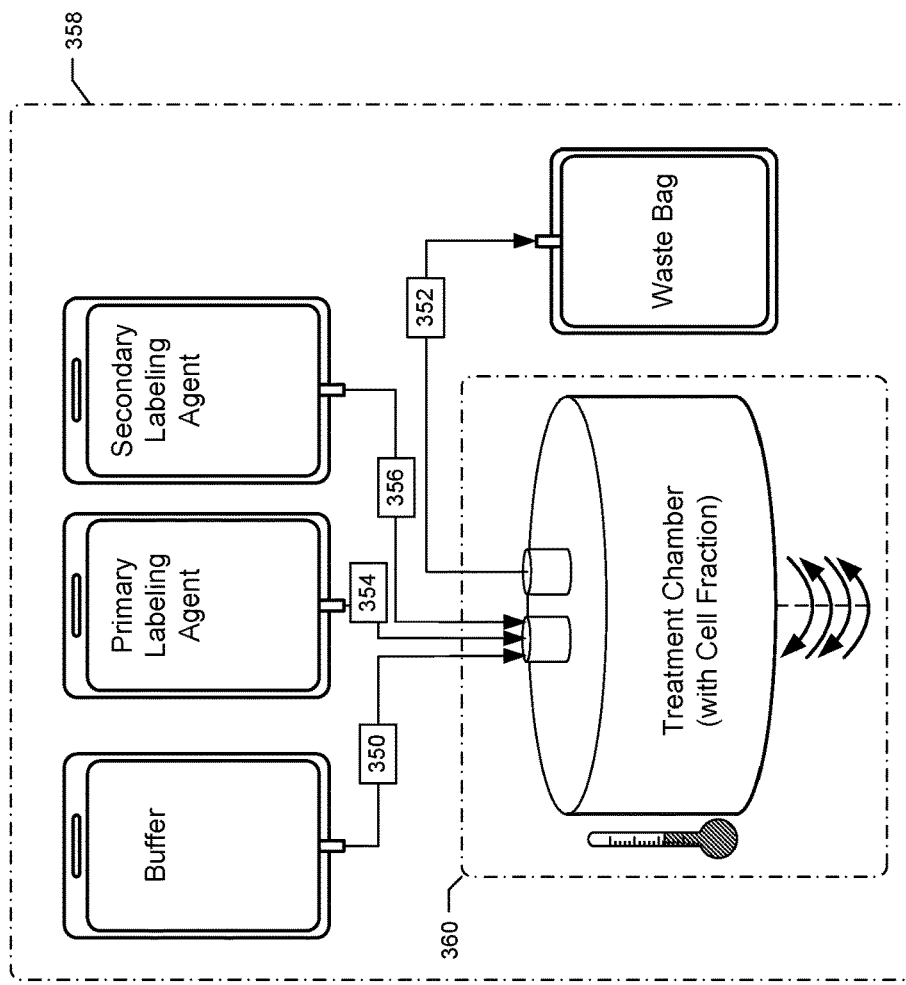
FIG. 3A shows a schematic diagram of an exemplary system for preparing (e.g. labeling and/or maintaining health of) target cells of a sample for later selection/isolation of the target cells.

Referring now to FIGS. 3A and 3B, an exemplary platelet removal and target cell selection method 300 may include diluting a cell fraction with a buffer as indicated by arrow 350. The buffer that is combined with the cell fraction at block 302 may or may not be the same buffer product(s) included in FIGS. 2A and 2B. In particular embodiments, the cell fraction is diluted in a Buffer (e.g. PBS/EDTA) prior to being pelleted at block 304 to remove platelets and/or any other samples which may interfere with subsequent selection/isolation. It should be appreciated from FIG. 3A that the pelleting of the cell fraction at block 304 may include centrifuging the cell fraction (e.g. the remaining portion of the original sample such as the RBC-Rich Fraction if RBC depletion has been performed) within the treatment chamber and, once pelleted, transferring the blood platelets from the treatment chamber to a waste receptacle, e.g. a waste bag, as indicated by arrow 352. In particular embodiments wherein the sample is an apheresis product, platelet removal may be preferably performed prior to target cell selection, concurrently with target cell selection, after target cell selection, or any combination thereof.

At block 306 a primary labeling agent may be added to the cell fraction as indicated by arrow 356. It should be appreciated from the foregoing disclosure that the primary labeling agent may include directly-conjugated immunomagnetic beads. It should be appreciated that the primary labeling agent and/or secondary labeling agent (if applicable) which may optionally be introduced at block 314 each may be added directly to the treatment chamber. Accordingly, in particular embodiments the same treatment chamber which may be used for RBC and/or platelet removal may be used for labeling the remaining target cells. In this way, the method 100 achieves a highly sensitive and complex objective with minimal equipment and/or opportunities for contamination. In particular, as should be appreciated based on the disclosure herein, the entire method 100 may be performed within a closed circuit in preferred embodiments.

At block 308, an incubation environment may be maintained within the treatment chamber to facilitate binding of the primary labeling agent with the target cells. In particular embodiments, at least part of the incubation environment is maintained for each component of the system of FIG. 3A (and FIGS. 2A, 4A, 5A, and 6A for that matter). For example, the incubation environment may be maintained within a boundary 358 which encapsulates some or all of the components of the system. For example, boundary 358 may include a glass hood which covers the system components including the treatment chamber and/or any other components such as a closed sample circuit (e.g. tubing corresponding to arrows 350, 352, 354, and 356) and containers of various products used in particular embodiments of method 100, e.g. a buffer bag or labeling agent bag. In particular embodiments, the treatment chamber is enclosed within a boundary 360 which does not enclose all other system components. Furthermore, particular embodiments include each of boundary 358 and boundary 360.

In particular embodiments, maintaining the incubation environment at block 308 includes controlling a temperature of the treatment chamber at block 310 as indicated by the thermometer symbol of FIG. 3A. For example, one or more heating or cooling units may be enclosed within the boundary 360. Furthermore, in particular embodiments, fluids and/or gases entering the treatment chamber may be passed through a heat exchange unit to quickly obtain a desired temperature. For example, in particular embodiments, the cell fraction within the treatment chamber may be maintained at 2-25 degrees Celsius during the incubation period in which the labeling agent(s) are reacting with the target cells.

In particular embodiments, maintaining the incubation environment at block 308 includes agitating the cell fraction at block 312. For example, in embodiments wherein the treatment chamber is configured to perform centrifugation the treatment chamber may spin at a slow speed to agitate or mix up the contents thereof. In particular embodiments, agitating the cell fraction at block 312 may be performed continuously. For example, the treatment chamber may continuously switch between spinning clock-wise and counter-clockwise as indicated by the alternating arrows about the vertical axis of FIG. 3A. In particular embodiments, the agitating the cell fraction may be performed on a predetermined period, e.g. 10 seconds of continuous agitation every 30 seconds such that each agitation cycle is followed by 20 seconds of non-agitation. Any other appropriate time intervals may also be used.

In particular embodiments, one or more secondary labeling agents may be added at block 314. For example, various embodiments of the method 100 may target more than one discrete type of cell and, therefore, may require more than one type of labeling agent to select the target cells. It should be appreciated that the addition of one or more secondary labeling agents may occur simultaneously with the addition of the primary labeling agent at block 306 and/or the maintaining of the incubation environment at block 308. Alternatively, the addition of one or more secondary labeling agents at block 314 may occur subsequent to the addition of the primary labeling agent at block 306. It should further be appreciated that in various embodiments the operation at block 314 is omitted, e.g. only a primary labeling agent is added.

At block 316, excess labeling agent may be separated from the cell fraction by removing the excess labeling agent from the treatment chamber without removing the cell fraction from the treatment chamber. For example, the contents of the treatment chamber including both the labeled cell fraction as well as the excess labeling agent may be centrifuged to separate these components into discrete layers and the layer corresponding to the excess labeling agent may be removed.

In particular embodiments, the labeled cell fraction may be concentrated at block 318 to a predetermined and/or user specified cell density appropriate for separating the target cells from the remaining non-target cells within the labeled cell fraction using the preferred separation method. Concentrating the cell fraction may be desirable when a target cell separator is likely to function with greater efficiency if the labeled cell fraction is passed through the target cell separator at a lower speed. For example, in an implementation wherein the target cell separator is a magnetic-activated cell sorter which uses a magnetic field to restrict magnetically labeled target cells from flowing through a magnetic separation column the slower the labeled cells pass through the sorter the more likely they may be to be retained within the target cell separator. Thus, reducing the volume of the cell fraction without removing labeled cells, i.e. concentrating the cell fraction, may improve subsequent target cell separation. Furthermore, in particular embodiments, a cell concentration which is too high may prevent instrumentation from operating properly, e.g. MACS columns or FACS machines may clog-up. Moreover, if FACS-based sorting of labeled cells is desired, high cell densities can cause inclusion of non-labeled cells during separation.

It should be appreciated that labeling the target cells may be performed using a labeling agent which selectively binds with target cell(s) and/or non-target cell, e.g. selecting a negative fraction. In particular embodiments, selectively binds means that a bead, antibody, or other binding moiety binds to a marker on a cell (e.g., CD3, CD4, CD8, CD13, CD14, CD15, CD16, CD19, CD20, CD34, CD45, CD45RA, CD45RO, CD49f, CD50, CD56, CD71, CD90, CD133) with a dissociation constant (1(D)) of $10^{-5}$ M or less, in particular embodiments of from $10^{-5}$ M to $10^{-13}$ M, or particular embodiments of from $10^{-5}$ M to $10^{-10}$ M. In particular embodiments, selectively binds means that a bead or antibody binds to a marker on a cell with a dissociation constant (1(D)) of $10^{-7}$ M or less, or in particular embodiments of from $10^{-7}$ M to $10^{-12}$ M, or in particular embodiments of from $10^{-7}$ M to $10^{-15}$ M. However, it should further be appreciated that labeling the target cells may also be performed without a labeling agent. For example, a target cell may be considered "labeled" based on an ability to distinguish and/or sort the target cells based on any identifying characteristic. In particular embodiments, one or more characteristics may be determined with regard to target cells and non-target cells as they pass between a light source and a light detector, e.g. as configured on a fluorescence-activated cell sorter, and an electrical charge (positive or negative) may be induced onto the target cells and/or non-target cells. Thus, in particular embodiments, target cells which have had a charge induced thereon may be considered labeled.

It should further be appreciated that computer-executable instructions stored on one or more memories may be executed to cause one or more hardware components of a point-of-care and/or portable target cell gene therapy device to perform one or more steps described in relations to FIGS. 3A and 3B. Exemplary description of computer-executable instructions for cell labeling (target or non-target for positive or negative selection) are denoted herein as one or both of SW1 and/or SW2 and are described as follows in Table 2.

TABLE 2

Exemplary description of computer-executable cell labeling instructions.

SW2 Description 1. Labeling of any desired cell fraction
SW2 Description 2. Labeling of any desired cell fraction with a directly-conjugated immunomagnetic bead.
SW2 Description 3. This program is suitable for labeling of any desired cell fraction with a directly-conjugated immunomagnetic bead or fluorophore-conjugated antibody(ies). The program initiates with the assumption that the cell product to be labeled is in the device chamber. The cell fraction to be labeled is first diluted in buffer and then is pelleted. Immunomagnetic beads or fluorophore-conjugated antibodies with or without blocking agent are then added and the chamber is cooled and gently shaken for an incubation period. Following incubation non-bound excess beads/antibodies are removed. Once washing is complete, labeled cell fraction remains in device chamber.
SW2 Description 4 (also referred to herein as J2). This program is suitable for labeling of any desired cell fraction with a directly-conjugated immunomagnetic bead or fluorophore-conjugated antibody(ies). The program initiates with the assumption that the cell product to be labeled is in the device chamber. The cell fraction to be labeled is first diluted in buffer and then is pelleted. Immunomagnetic beads (up to 15 mL) or fluorophore-conjugated antibody (up to 10 mL) with or without blocking agent are then added and the chamber is covered to restrict light exposure, cooled to 2-25° C. and gently shaken for a total incubation period of 30 minutes. Following incubation the labeled cell fraction is centrifuged and washed to remove non-bound excess beads or antibodies. Once washing is complete, labeled cell fraction is concentrated to desired volume and remains in device chamber.
SW3 Description 1. This program is suitable for two-step labeling of any desired cell fraction with a primary antibody/labeling agent followed by a secondary-antibody/agent magnetic bead. The program initiates with the assumption that the cell product to be labeled is in the device chamber.

TABLE 2-continued

Exemplary description of computer-executable cell labeling instructions.

SW3 Description 2. This program is suitable for two-step labeling of any desired cell fraction with a primary antibody/labeling agent followed by a secondary-antibody/agent or magnetic bead. The program initiates with the assumption that the cell product to be labeled is in the device chamber. The volume to be labeled is set to allow adjustment of cell, antibody and/or bead concentrations to desired values.
The cell fraction to be labeled is diluted in Buffer and then is pelleted. Supernatant is removed to bring the labeling volume to the desired value. The primary antibody/agent with or without blocking agent is then added for an incubation period. The secondary antibody/agent magnetic beads are then added for a second incubation period. Following incubation the labeled cell fraction is washed to remove non-bound excess antibody/agent/beads.
SW3 Description 3. This program is suitable for two-step labeling of any desired cell fraction with a primary antibody/labeling agent followed by a secondary-antibody/agent magnetic bead. The program initiates with the assumption that the cell product to be labeled is in the device chamber. The volume to be labeled is set by the user to allow adjustment of cell, antibody and bead concentrations to desired values. The cell fraction to be labeled is first diluted in Buffer (e.g. PBS/EDTA) and then is pelleted. Supernatant is removed to bring the labeling volume to the desired value. The primary antibody/agent with or without blocking agent is then added and the chamber is gently shaken for a total incubation period. The secondary antibody/agent magnetic beads are then added, and the chamber is gently shaken for a second incubation period. Following incubation the labeled cell fraction is centrifuged and washed to remove non-bound excess antibody/agent/beads. Once washing is complete, labeled cell fraction is concentrated to desired volume for enrichment and remains in device chamber.
SW3 Description 4 (also referred to herein as J3). This program is suitable for two-step labeling of any desired cell fraction with a primary antibody/labeling agent followed by a secondary-antibody/agent magnetic bead. The program initiates with the assumption that the cell product to be labeled is in the device chamber. The volume to be labeled is set by the user to allow adjustment of cell, antibody and bead concentrations to desired values. The cell fraction to be labeled is first diluted in Buffer (e.g. PBS/EDTA) and then is pelleted in a stepwise fashion. Supernatant is removed to bring the labeling volume to the desired value input by the user. The primary antibody/agent with or without blocking agent is then added and the chamber is cooled to 2-25° C. and gently shaken every 30 seconds for a total incubation period of 30 minutes. The secondary antibody/agent magnetic beads are then added, chamber temperature is maintained at 2-25° C. and the chamber is gently shaken every 30 seconds for a second incubation period of 30 minutes. Following incubation the labeled cell fraction is centrifuged and washed to remove non-bound excess antibody/agent/beads. Once washing is complete, labeled cell fraction is concentrated to desired volume for enrichment and remains in device chamber.

Referring now back to FIG. 1, the method 100 may further include isolating the target cells of the cell fraction from non-target cells at block 116. Isolating the target cells at block 116 may include any appropriate procedure such as, for example, magnetic-activated cell sorting (MACS), fluorescence-activated cell sorting (FACS), and/or affinity chromatography.

As indicated, any technique known in the art for cell selection/isolation can be used. Exemplary methods rely on cell size and/or forward, side and back light scatter properties of cells and/or differential expression of cell surface markers. Antibodies binding the cell surface markers can be conjugated with labels as indicated above, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. In particular embodiments, the selection/isolation of target cells is affected by contacting a target cell sample with a solid substrate (e.g., beads, flask, magnetic particles) to which antibodies are bound, and by removing any unbound cells, wherein the target cells can be found either in the cells bound to the solid substrate or in the unbound cells depending on the antibodies used.

In particular embodiments, a sample is processed to select/isolate (e.g. enrich for) CD34+ cells using anti-CD34 antibodies directly or indirectly conjugated to magnetic particles in connection with a magnetic cell separator which employs nano-sized super-paramagnetic particles composed of iron oxide and dextran coupled to specific monoclonal antibodies. The cell separator should be a closed sterile system, outfitted with single-use disposable tubing. Particular embodiments can alternatively include negative selection, selecting for non-CD34 cells, and allowing only CD34+ cells to pass through a selection paradigm. For example, antibodies selecting for CD133+ cells, CD43+ cells, CD45RO+ cells, CD45RA+ cells, CD49f+ cells, CD59+ cells, CD90+ cells, CD109+ cells, CD11+ cells 7, CD166+ cells, or a combination of the foregoing, can be enriched for using antibodies in positive selection embodiments. In another example, antibodies selecting for CD3+ cells, CD4+ cells, CD8+ cells, CD13+ cells, CD14+ cells, CD15+ cells, CD16+ cells, CD19+ cells, CD20+ cells, CD56+ cells, or a combination of the foregoing, can be depleted using antibodies in negative selection embodiments.

Selection/isolation thus refers to a process wherein the percentage of target cells (e.g. HSPC) in the sample is increased (relative to the percentage in the sample before the selection/isolation procedure). In particular embodiments, the increase in the number of target cells (or other suitable antigen-positive cells) as a percentage of cells in the enriched sample, relative to the sample prior to the selection/isolation procedure, is at least 25-, 50-, 75-, 100-, 150-, 200-, 250-, 300-, 350-fold, and preferably is 100-200 fold. In a preferred embodiment, CD34+ cells are selected/isolated using a monoclonal antibody to CD34, which antibody is conjugated to a magnetic bead, and a magnetic cell separation device to separate out the CD34+ cells. In particular embodiments, using anti-CD34 antibodies, target cells are enriched from 1-2% of a normal bone marrow cell population to >80% of the population.

Figure 4B:
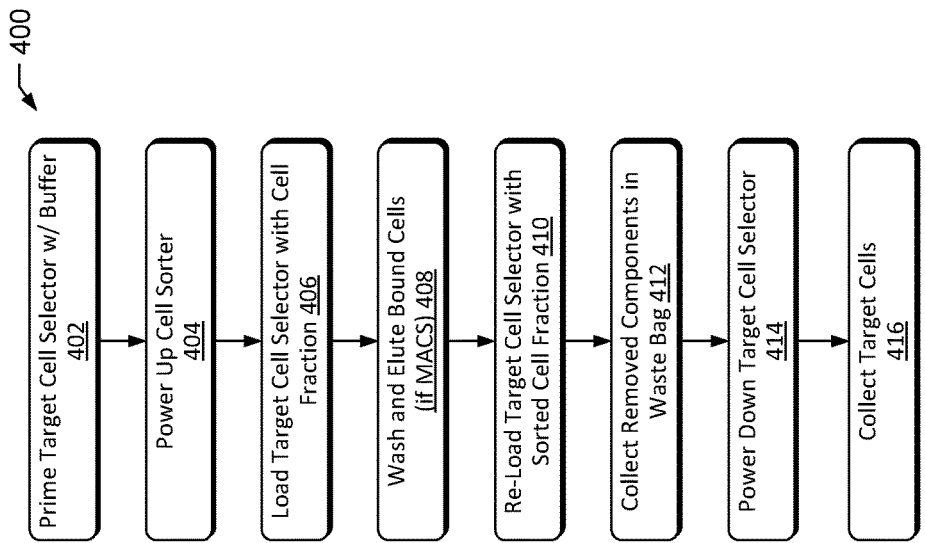
FIG. 4B is a flow chart of an exemplary method for selecting/isolating target cells using the exemplary system of FIG. 4A.
Figure 4A:
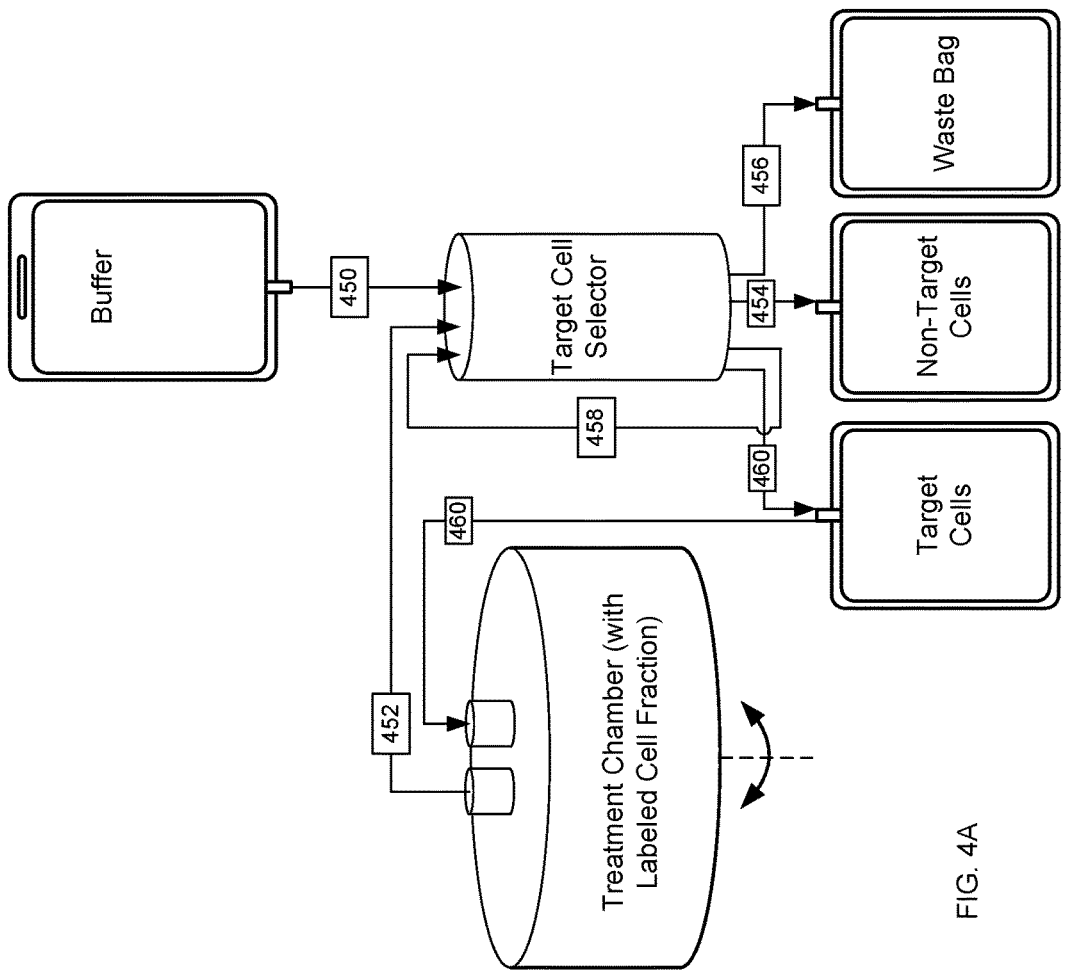
FIG. 4A shows a schematic diagram of an exemplary system for selection/isolation of target cells.

Referring now to FIGS. 4A and 4B, an exemplary target cell selection method 400 may include priming a target cell selector such as a MACS based cell selector with a buffer as indicated by arrow 450. For example, a magnetic column and pre-column of MACS based target cell selector have a buffer (e.g. PBS/EDTA) pumped through it prior to being powered on, e.g. caused to generate a magnetic field, at block 404 and/or loaded with the labeled cell fraction at block 406. In particular embodiments, the priming at block 402 occurs following the powering up of the cell sorter at block 404 or does not occur at all, e.g. the cell sorter is not primed.

At block 406, the target cell selector is loaded with the prepared (e.g., labeled) cell fraction as indicated by arrow 452. For example, the contents of the treatment chamber including the target cells, which in particular embodiments have been labeled, are passed through the target cell selector. In particular embodiments using MACS sorting technology wherein target cells have been magnetically labeled with immunomagnetic beads the target cells may become magnetically bound to a portion of the target cell selector. Alternatively, non-target cells may be labeled such that target cells are isolated causing non-target cells to bind to the target cell selector while allowing target cells to pass through. Non-target cells and other "pass-through" components of the labelled cell fraction may be collected in one or both of a Non-Target cell receptacle as indicated by arrow 454 and/or a waste receptacle as indicated by arrow 456.

In embodiments using MACS based cell selection, the bound cells may be washed and/or eluted at block 408. As described elsewhere herein, it should be appreciated that target cell selection at block may utilize non-MACS based technology, e.g. flow cytometry. Accordingly, in particular embodiments target cells would not be "bound," e.g. there would be no immunomagnetic beads used to label the target cells.

At block 410, the sorted cells may be reloaded onto the cell separator as indicated by arrow 458. Reloading the cell separator with the already sorted cell fraction may increase the selection/isolation (e.g., purity) of the final sorted cell fraction. In particular embodiments, the reloading the sorted cell fraction at block 410 occurs at a slower transfer rate than the initial loading at block 406.

At block 412, components which are removed during the washing and/or eluting at block 406 (if applicable) may be collected in a waste receptacle or bag as indicated by arrow 456.

In particular embodiments, the target cell selector may be powered down at block 414. For example, in embodiments using MACS sorting technology powering down the target cell selector at block 414 may terminate generation of a magnetic field to released selected/isolated target cells which are bound to the target cell separator. At block 416, target cells may be collected by transferring them to one or more of a target cell receptacle (e.g. the bag labeled "Target Cells" of FIG. 4A) and then from the target cell receptacle into the treatment chamber as indicated by arrows 460. Exemplary description of computer-executable instructions are denoted herein as SW4 and are described as follows in Table 3:

TABLE 3

Exemplary description of computer-executable selection/isolation instructions.

SW4 Description 1. This program is suitable for selection of any labeled cell fraction.
SW4 Description 2. This program is suitable for magnetic column based selection of any labeled cell fraction. The program initiates with the assumption that the labeled cell fraction to be selected is in the device chamber. If magnetic bead-based selection, a magnetic column and pre-column on the device are primed with buffer. The cell fraction to be selected is passed through the pre-column and over the magnetic column with the magnet turned on. Cells bound to the column are released and collected. If FACS-based sorting, the sorter is primed with buffer. Cells are passed through the sorter and labeled cells are included/excluded in the sorted population based on positive or negative selection.
SW4 Description 3. This program is suitable for magnetic column based selection of any labeled cell fraction. The program initiates with the assumption that the labeled cell fraction to be selected is in the device chamber. A magnetic column and pre-column on the device are primed with buffer. The cell fraction to be selected is passed through the pre-column and over the magnetic column with the magnet turned on. Any component of the labeled fraction which does not bind to either the pre-column or the magnetic column (termed "flow-through") is collected. Following column loading, bound cells are washed, eluted and re-loaded onto the column to increase purity of the enriched fraction. Cells bound to the column are released and collected.
SW4 Description 4. This program is suitable for magnetic column based selection of any labeled cell fraction. The program initiates with the assumption that the labeled cell fraction to be selected is in the device chamber. A magnetic column and pre-column on the device are primed with Buffer (e.g. PBS/EDTA). The cell fraction to be selected is passed through the pre-column and over the magnetic column with the magnet turned on. Any component of the labeled fraction which does not bind to either the pre-column or the magnetic column (termed "flow-through") is collected in a bag included in the pre-fabricated tubing set.

TABLE 3-continued

Exemplary description of computer-executable selection/isolation instructions.

Following column loading, bound cells are washed, eluted and re-loaded onto the column at slow speed to increase purity of the enriched fraction. Any component of the labeled fraction which is removed during the wash steps is collected in the waste bag included in the pre-fabricated tubing set. Finally, the magnet is turned off and cells bound to the column are released and collected into a bag included in the pre-fabricated tubing set. The final elution volume is 45 mL.
SW4 Description 5 (also referred to herein as J4). This program is suitable for magnetic column based selection of any labeled cell fraction. The program initiates with the assumption that the labeled cell fraction to be selected is in the device chamber. A magnetic column and pre-column on the device are primed with Buffer (e.g. PBS/EDTA). The cell fraction to be selected is passed through the pre-column and over the magnetic column with the magnet turned on. Any component of the labeled fraction which does not bind to either the pre-column or the magnetic column (termed "flow-through") is collected in a bag labeled "Negative Fraction Bag" included in the pre-fabricated tubing set. Following column loading, bound cells are washed, eluted and re-loaded onto the column at slow speed to increase purity of the enriched fraction. Any component of the labeled fraction which is removed during the wash steps is collected in the Waste Bag included in the pre-fabricated tubing set. Finally, the magnet is turned off and cells bound to the column are released and collected into the bag labeled "Target Cell Bag" included in the pre-fabricated tubing set. The final elution volume may be 45 mL.

Figure 8A:
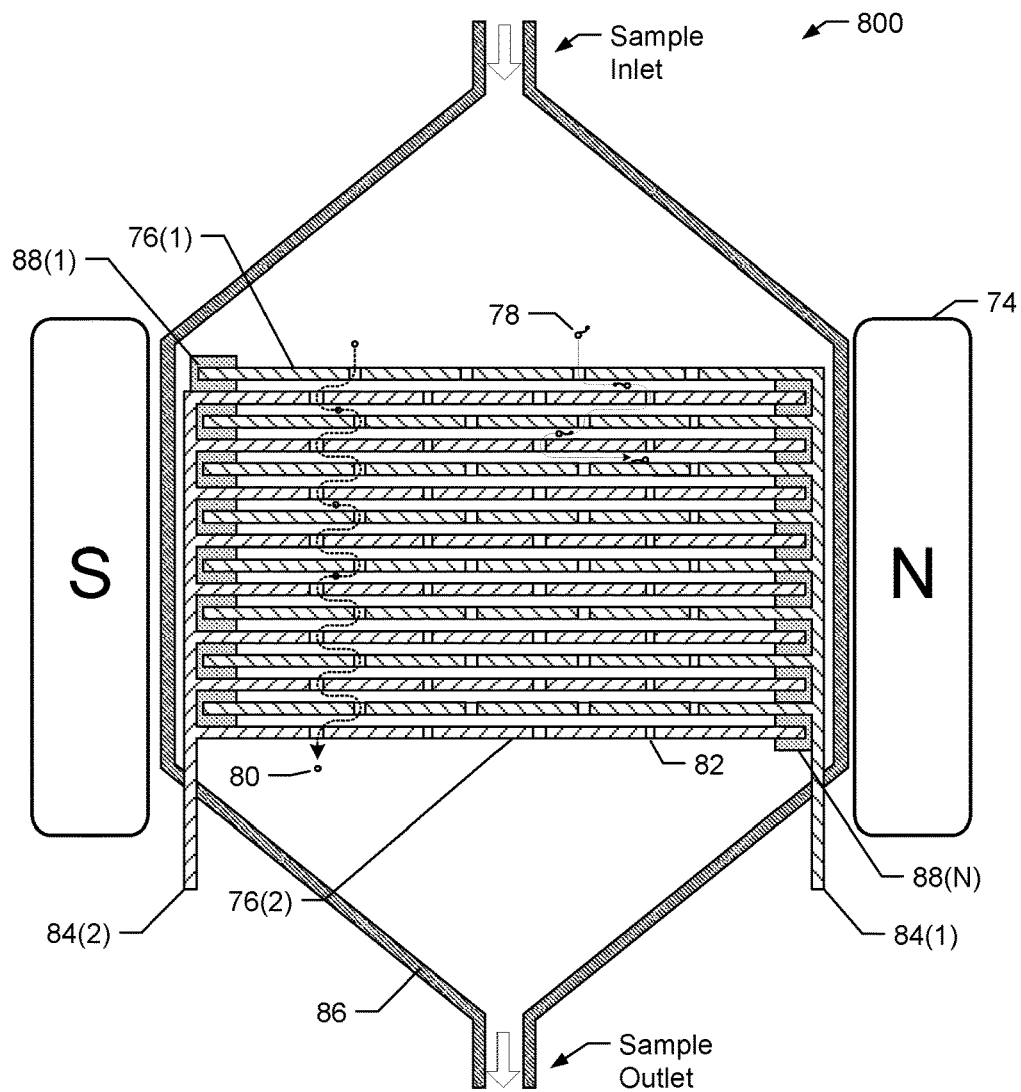
FIG. 8A illustrates a combination cell separator and genetic modification introducer (CCS-GMI) in a magnetized state.

In particular embodiments the target cells may be transferred out of the target cell selector, e.g. returned to the treatment chamber, prior to being introduced to a genetic modifier. However, referring now to FIG. 8, in particular embodiments, the target cells may remain within a combination cell separator and nucleic acid introducer (CCS-GMI) 800 during both target cell selection and nucleic acid introduction. In particular embodiments, a genetic modifier may be introduced to the target cells within a CCS-GMI 800 after having been selected therein. For example, the CCS-GMI 800 may utilize magnetic activated cell sorting (MACS) technology to magnetically retain target cells on a magnetically susceptible or ferromagnetic material without affecting the ability of non-target cells to flow through and exit the target cell separator. Such materials include iron, steel, cobalt nickel, and other ferromagnetic rare earth metals of alloys thereof. It will be appreciated by those skilled in the art that such materials may be readily magnetized and demagnetized.

Figure 5B:
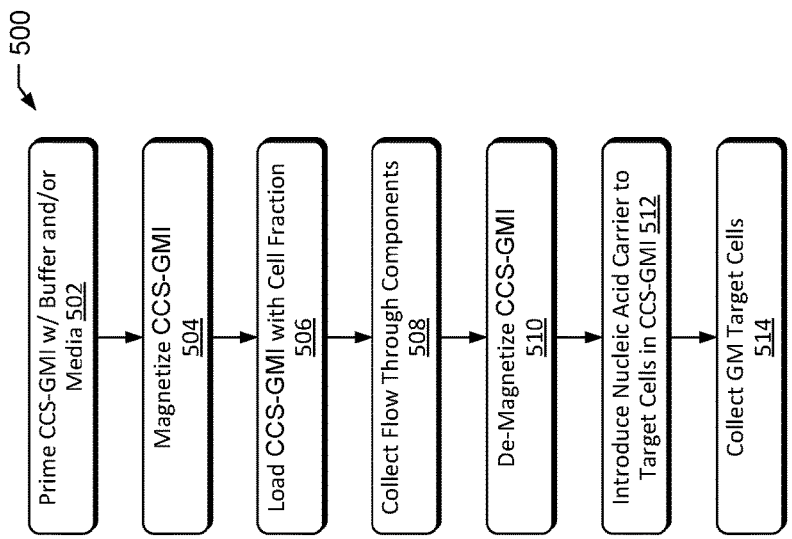
FIG. 5B is a flow chart of an exemplary method for selecting/isolating target cells using the exemplary system of FIG. 5A.
Figure 5A:
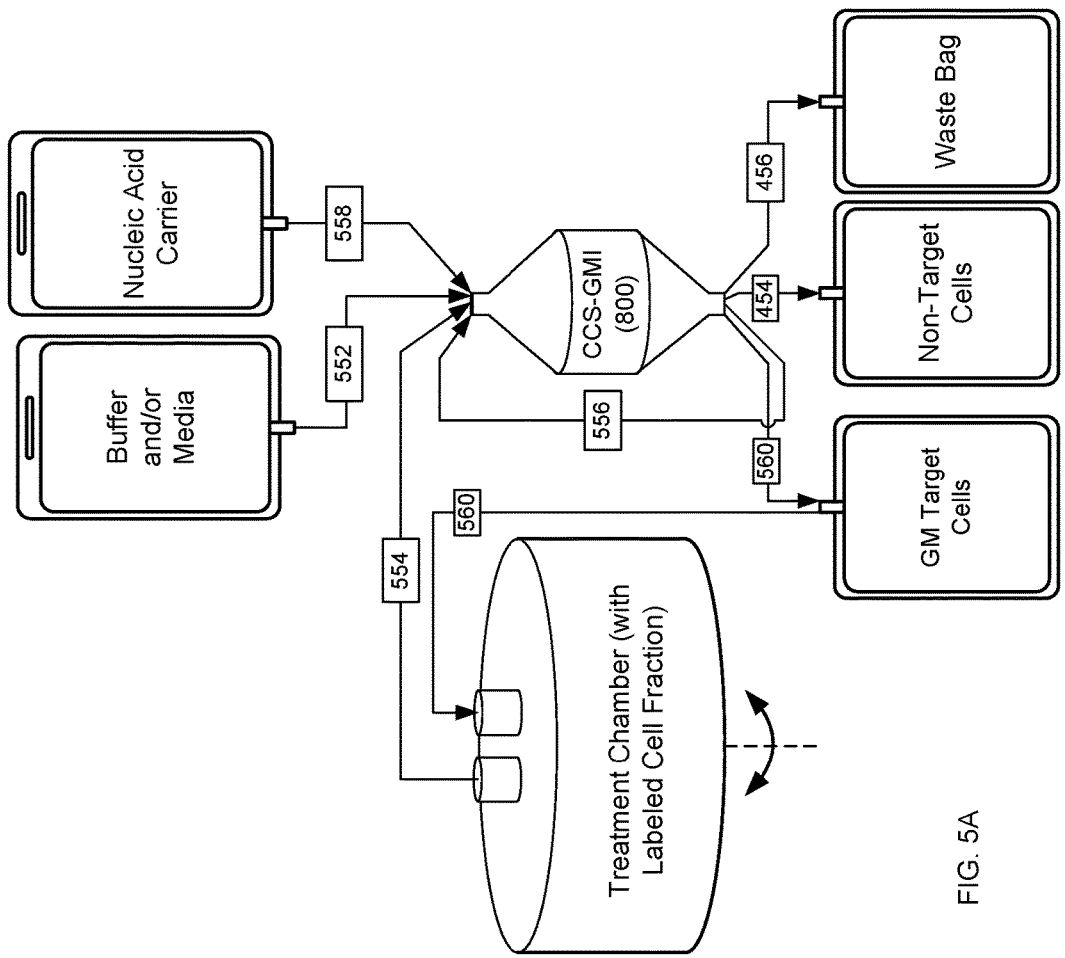
FIG. 5A shows a schematic diagram of an exemplary system for selection/isolation and gene modification of target cells.

With reference now to FIGS. 5A and 5B (collectively FIG. 5), FIG. 5A shows a schematic diagram of an exemplary system for selection/isolation and gene modification of target cells whereas FIG. 5B is a flow chart of an exemplary method 500 for selecting/isolating target cells using the exemplary system of FIG. 5A.

At block 502, the CCS-GMI 800 may be primed with buffer and/or media solution as indicated by arrow 552. It should be appreciated that any suitable buffer and/or media solution may be used to prime the CCS-GMI 800 including any buffer and/or media disclosed herein.

At block 504, the CCS-GMI 800 may be magnetized to facilitate separation/isolation of the target cells. For example, referring back to FIG. 8, the CCS-GMI 800 may be temporarily disposed between opposing magnetic poles, e.g. South pole 72 and North pole 74, thereby causing one or more magnetically susceptible materials to become magnetized to attract target cells which have been magnetically labeled. For example, a target cell 78 which has been labeled with an immunomagnetic bead (shown but not independently labeled in the figures) may be attracted to and retained on a surface of a first magnetically susceptible material 76(1) while non-target cell 80 is not magnetically labeled and thus is carried through a series of pores 82 which form at least one flow path between a sample inlet and a sample outlet. Various techniques may be readily employed for magnetizing a porous and magnetically susceptible material for the purpose of MACS. Such techniques may include permanent magnets or electromagnets. It should be appreciated that individual components may be selected from a number of readily available alternates and may be combined in a variety of configurations without departing from the general description of the CCS-GMI 800 of the present disclosure.

At block 506, the CCS-GMI 800 may be loaded with a labeled cell fraction as indicated by arrow 554 during which time target cell(s) 78 are retained within the CCS-GMI 800 while non-target cell(s) 80 and other sample components are passed through the CCS-GMI 800 and collected in one or both of a non-target cell bag or a waste bag. For example, referring now to FIGS. 9A and 9B (collectively FIG. 9), which is similar to FIG. 8, the CCS-GMI 800 is illustrated in a magnetized state during the performance of MACS with Section-A of FIG. 9A being enlarged in FIG. 9B. With particular reference to FIG. 9B, it can be seen that target cell 78 is magnetically attracted to the currently magnetized first electrode 76(1) which, as described above, may also be a magnetically susceptible material. It should be appreciated that as there is no electrical potential between the first electrode 76(1) and the second electrode 76(2) there is no electric field there between. Stated alternatively, the electric field strength (as a result of voltage applied at terminals 84(1) and/or 84(2)) is equal to 0 Volts per millimeter (mm). It should be appreciated that in performing electroporation, cells are typically exposed to very short pulses of an electric field. In many applications the pulse length is measured in terms of micro to milliseconds. The pulse length works indirectly with the field strength to increase pore formation and, therefore, the potential for intended genetic modifications to be induced into a target cell. It will be appreciated by one skilled in the art that both pulse length and applied voltage must be carefully optimized based on specific characteristics of the target cell(s) and that too long a pulse length may result in irreversible electroporation, e.g. the target cells may be killed. Accordingly, in preferred embodiments voltage is not applied between the first and second electrodes 76(1) and 76(2) during the performance of cell separation/isolation, e.g. MACS.

In particular embodiments, loading the CCS-GMI 800 at block 506 includes re-circulating the sample through the CCS-GMI 800 as indicated by arrow 556. Thus, any labeled target cells which were un-retained during a previous pass through the CCS-GMI 800 may become retained during a subsequent pass. At block 508, excess buffer and/or media may be collected in a waste bag as indicated by arrow 456.

At block 510, the CCS-GMI 800 may be de-magnetized. For example, referring now to FIGS. 10A and 10B (collectively FIG. 10), which are similar to FIG. 8, the CCS-GMI 800 is illustrated in a non-magnetized state during the performance of an electroporation pulse with Section-B of FIG. 9A being enlarged in FIG. 9B. With particular reference to FIG. 9B, it can be seen that target cell 78 is no longer magnetically attracted to the previously magnetized first electrode 76(1) but rather moves freely through a fluid suspension, e.g. a buffer or media solution, within the CCS-GMI 800.

At block 512, a genetic modifier may be introduced to the target cells following selection/isolation thereof. For example, reversible electroporation may be used to generate temporary pores within a membrane of the target cell 78 to allow for a genetic modifier, e.g. naked DNA or RNA, to enter the cell. In particular embodiments, an electric field is created within a volume of the CCS-GMI 800 in which the MACS is also performed. It should be appreciated that electric field strength may be measured as the voltage delivered across an electrode gap and may be expressed as E=Voltage/distance (of the electrode gap).

With particular reference to FIG. 10B, in particular embodiments, one or more magnetically susceptible materials may further serve as opposing electrodes to generate an electric field. For example, the first magnetically susceptible material 76(1) be spaced apart from a second magnetically susceptible material 76(1) such that applying a voltage across the first and second magnetically susceptible materials may generate an electric field there between. Stated alternatively, in particular embodiments, the first magnetically susceptible material 76(1) may also serve as a first electrode and the second magnetically susceptible material may also serve as a second electrode. In particular embodiments, the first electrode 76(1) may include a first terminal 84(1) and the second electrode 76(2) may include a second terminal 84(2). Furthermore, each of the first terminal 84(1) and the second terminal 84(2) may protrude from a housing 86 (labeled in FIG. 8A) of the CCS-GMI 800 to allow for a voltage to be applied for generation of an electric field. In particular embodiments, the housing 86 may include metal, glass, plastic, polymeric material, or combinations thereof. In one embodiment, the housing 86 includes polycarbonate.

In particular embodiments, the introduction of the nucleic acid at block 512 occurs after the loading of block 506 and de-magnetization of block 510. For example, in contrast to FIG. 9 (e.g. at which time the CCS-GMI is magnetized), in FIG. 10 an electrical potential does exist between the first and second electrodes 76(1) and 76(2) and, therefore, the target cell 78 is being exposed to an electric field which may generate pores in the target cells membrane. In the illustrated embodiment, the intended electric field strength of 1.25 kV/cm is generated by application of 125 volts across terminals 84(1) and 84(2) since the distance between electrodes is 1 mm. It should be appreciated that if the electrode gap were 2 mm then 250 volts would be required to generate the intended electric field strength of 1.25 kV/cm. In particular embodiments, the nucleic acid intended for introduction to the target cell may enter the CCS-GMI 800 with the target cell(s) 78, e.g. the two may be combined prior to the MACS process. It should appreciated, however, that in particular embodiments the nucleic acid intended for introduction may be introduced during a final period of the MACS process, e.g. when an appropriate amount of target cells have already been magnetically affixed to the magnetically susceptible materials but prior to their release, as indicated by arrow 558. For example, the target cell(s) 78 may be transferred into and magnetically retained in the CCS-GMI 800, then while the target cell(s) 78 are being retained nucleic acid(s) may be transferred into the CCS-GMI 800, then the target cell(s) may be exposed to an electric field either prior to, during, or after their magnetic release. Such embodiments may be preferable because a lesser volume and/or higher concentration of nucleic acid molecules may be controllably placed proximate to the target cell(s) 78. In particular embodiments, the nucleic acid(s) intended for genetic modification of the target cell(s) 78 may be introduced following a time at which the target cell(s) have been magnetically released. In particular embodiments, the nucleic acid may be introduced prior to a MACS process. In particular embodiments, the CCS-GMI 800 may be used to perform MACS but not electroporation, whereas in particular embodiments the CCS-GMI 800 may be used to perform electroporation but not MACS. It should be appreciated that in particular embodiments the sample inlet, e.g. labeled in FIG. 8A, may correspond to arrows 450, 452, and 458 of FIG. 4A and that the sample outlet, e.g. also labeled in FIG. 8A, may correspond to arrows 454, 456, 458, and 460 of FIG. 4A.

Figure 8B:
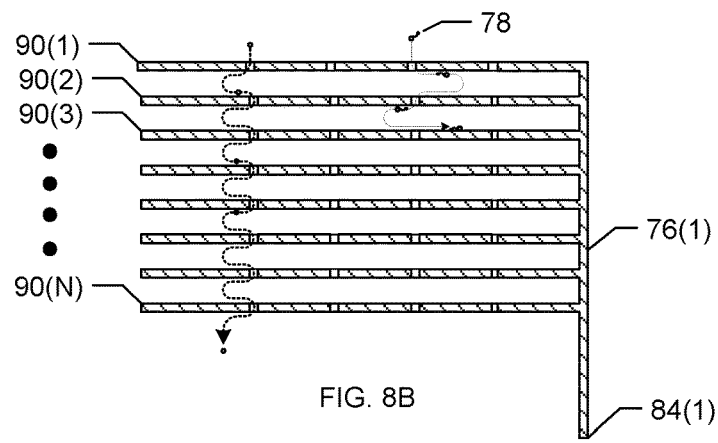
FIG. 8B illustrates a first electrode of the CCS-GMI of FIG. 8A.
Figure 11:
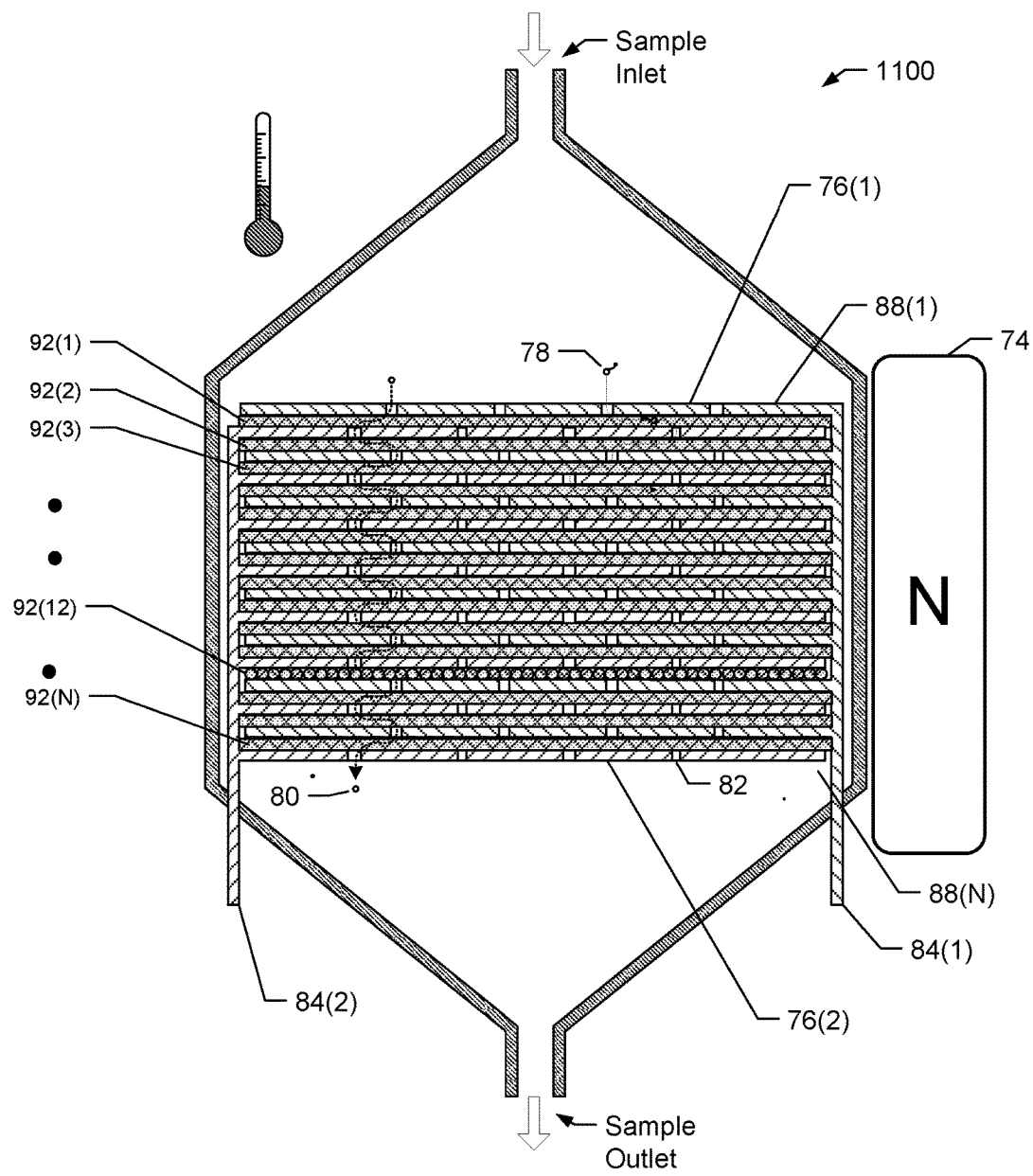
FIG. 11 illustrates a device which may perform one or both of cell separation or electroporation.

Referring now to FIG. 8B, in particular embodiments the first electrode 76(1) may include a first plurality of protrusions 90(1)-90(N) which may mate with a second plurality of protrusions of the second electrode 76(2). The electrodes 76 may include any suitable conductive material such as, for example, steel or aluminum. In particular embodiments, the first terminal 84(1) and the second terminal 84(2) are respective conductors of a two conductor wire which protrude from the housing at a single location. For example, in particular embodiments a two conductor wire may protrude through the housing at a single location and each individual conductor may be conductively affixed, e.g. soldered, to opposing electrodes.

Referring back now to FIG. 8A, in particular embodiments, the CCS-GMI 800 may include one or more insulators 88(1)-88(N) between the first electrode 76(1) and the second electrode 76(2). In preferred embodiments, the insulators 88 are constructed of from an electrical insulator such that an electrical current is unable to pass through the insulators 88 from the first electrode 76(1) to the second electrode 76(2) when a voltage is supplied to the first terminal 84(1) and/or the second terminal 84(2). Furthermore, in preferred embodiments, the insulators 88 may provide physical support between various portions of the first electrode 76(1) and the second electrode 76(2) to generate precise and/or uniform spacing between electrodes. It should be appreciated that increased precision and/or uniformity of electrode spacing may translate to increased control and/or uniformity of one or more characteristics of a generated electric field, e.g. electric field strength.

In particular embodiments, the electrodes include a different structure than the magnetically susceptible material. For example, a magnetically susceptible material may be placed between the electrodes. Referring now to FIG. 10, a cell separator and/or electroporator 1100 is illustrated with a plurality of magnetically susceptible materials (MSMs) 92(1)-92(N) placed between electrodes 76(1) and 76(2). It should be appreciated that in preferred embodiments the magnetically susceptible material may be a porous or otherwise permeable matrix through which a sample may freely flow. In particular embodiments, the MSMs 92 may be wires, metal coated fibers, steel wool, or small spheres. It may be preferable that the MSMs 92 include small spheres, e.g. as illustrated at 92(12), which may enable accurate spacing to be maintained between the electrodes 76(1) and 76(2). In particular embodiments, a coating may be applied to the MSMs which make up the permeable matrix. The coating may be selected to be substantially impermeable to ions to protect the MSMs from corrosion as well as to inhibit the escape of cations from the matrix which may damage the cells. Additional details with regard to the MSMs, and MACS generally, may be found in U.S. Pat. No. 8,727,132. The coating may be selected to be an electrical insulator such that the internal electric charges of the coating do not flow freely and, therefore, electric current is unable to pass through the coating to the MSMs. Accordingly, the coating may prevent electric current from flowing from the first electrode to the second electrode In particular embodiments, the cell separator and/or electroporator 1100 may include or be placed proximate to a temperature control unit to maintain and/or control the temperature of the cells during one or both of the MACS process and the electroporation process. It will be appreciated by one skilled in the art that the temperature at which the target cell(s) 78 are maintained during electroporation may affect the efficiency of the electroporation. For example, some mammalian cell lines are effectively electroporated at room temperature. Moreover, the electroporation pulses may actually raise the temperature of the sample. For some cell lines, the increased temperature due to the pulses may cause increased cell death and lower the transfection efficiency. However, maintaining the sample at lower temperatures can diminish the heating effects on cell viability and efficiency. Furthermore, because reversible electroporation generates transient formation of pores, maintaining the cells at a reduced temperature following the pulse may allow the pores to remain open longer to allow more uptake of the nucleic acid. Accordingly, in particular embodiments, it may be preferable to dissipate heat caused by the generation of the electric field.

In particular embodiments, the electric field is generated by a controlled application of DC current for a short duration of time, e.g. a DC pulse. In particular embodiments, the electric field is generated by a controlled application of AC current to bring together or align cells. For example, electrofusion and/or electroporation may be performed with the CCS-GMI 800 and/or cell separator and/or electroporator 1100 disclosed herein. Additional details with regard to the electroporation devices may be found in; U.S. Patent Application Publication No. 2005/0277183; U.S. Pat. Nos. 8,105, 818; 8,043,838.

Referring now to FIG. 6 in conjunction to FIG. 4, in particular embodiments the target cells may be transferred out of the target cell selector, e.g. returned to the treatment chamber, prior to being introduced to a genetic modification. For example, in particular embodiments blocks 116 and 120 of method 100 are performed within a single device, e.g. CCS-GMI 800, and in particular embodiments block 116 is performed within a cell separator whereas block 120 is performed within one or more different system components, e.g. the treatment chamber. In particular embodiments, once the target cells are transferred out of target cell selector, method 100 may continue to block 118 at which the selected/isolated target cells may optionally undergo expansion, or stimulation, or both. In particular embodiments, when target cells are HSPC and expansion is performed, the HSPC can be cultured in the presence of one or more of Notch agonists, aryl hydrocarbon receptor antagonists, pyrimidoindole derivatives (e.g., UM 729 or UM 171), cytokines, chemokines, steroids (e.g., prostaglandin E2), and/or steroid derivatives. These molecules can be in a fluid contacting the cells. Exposure to particular molecules enhances infection with lentiviruses. For example, UM729 and Rapamycin enhance lentivirus transduction efficiency.

Notch agonists include any compound that binds to or otherwise interacts with Notch proteins or other proteins in the Notch pathway such that Notch pathway activity is promoted. Exemplary Notch agonists are the extracellular binding ligands Delta and Serrate (e.g., Jagged), RBP JϰI Suppressor of Hairless, Deltex, Fringe, or fragments thereof which promote Notch pathway activation. Nucleic acid and amino acid sequences of Delta family members and Serrate family members have been isolated from several species and are described in, for example, WO 1993/12141; WO 1996/27610; WO 1997/01571; and Gray et al., 1999, Am. J. Path. 154:785-794.

In particular embodiments, the Notch agonist is Delta1$^{ext-IgG}$. In particular embodiments, Delta1$^{ext-IgG}$ is applied at a concentration between 0.2 and 20 μg/ml, between 1.25 and 10 μg/ml, or between 2 and 6 μg/ml.

As is understood by one of ordinary skill in the art, additional culture conditions can include expansion in the presence of one more growth factors, such as: angiopoietin-like proteins (Angptls, e.g., Angptl2, Angptl3, Angptl7, Angptl5, and Mfap4); erythropoietin; fibroblast growth factor-1 (FGF-1); Flt-3 ligand (Flt-3L); granulocyte colony stimulating factor (G-CSF); granulocyte-macrophage colony stimulating factor (GM-CSF); insulin growth factor-2 (IFG-2); interleukin-3 (IL-3); interleukin-6 (IL-6); interleukin-7 (IL-7); interleukin-11 (IL-11); stem cell factor (SCF; also known as the c-kit ligand or mast cell growth factor); thrombopoietin (TPO); and analogs thereof (wherein the analogs include any structural variants of the growth factors having the biological activity of the naturally occurring growth factor; see, e.g., WO 2007/1145227 and U.S. Patent Publication No. 2010/0183564).

In particular embodiments, the amount or concentration of growth factors suitable for expanding HSPC is the amount or concentration effective to promote proliferation of HSPC, but substantially no differentiation of the HSPC.

The amount or concentration of growth factors suitable for expanding HSPC depends on the activity of the growth factor preparation, and the species correspondence between the growth factors and HSPC, etc. Generally, when the growth factor(s) and HSPC are of the same species, the total amount of growth factor in the culture medium ranges from 1 ng/ml to 5 μg/ml, from 5 ng/ml to 1 μg/ml, or from 5 ng/ml to 250 ng/ml. In additional embodiments, the amount of growth factors can be in the range of 5-1000 or 50-100 ng/ml.

In particular embodiments, the foregoing growth factors are present in the culture condition for expanding HSPC at the following concentrations: 25-300 ng/ml SCF, 25-300 ng/ml Flt-3L, 25-100 ng/ml TPO, 25-100 ng/ml IL-6 and 10 ng/ml IL-3. In more specific embodiments, 50, 100, or 200 ng/ml SCF; 50, 100, or 200 ng/ml of Flt-3L; 50 or 100 ng/ml TPO; 50 or 100 ng/ml IL-6; and 10 ng/ml IL-3 can be used.

In particular embodiments, HSPC can be expanded by exposing the HSPC to a Notch agonist, and 50 ng/ml or 100 ng/ml SCF; to a Notch agonist, and 50 ng/ml or 100 ng/ml of each of Flt-3L, IL-6, TPO, and SCF; or a Notch agonist, and 50 ng/ml or 100 ng/ml of each of Flt-3L, IL-6, TPO, and SCF, and 10 ng/ml of IL-11 or IL-3.

In particular embodiments, HSPC expansion disclosed herein does not utilize an extracellular matrix protein such as fibronectin (FN), or a fragment thereof (e.g., CH-296 (Dao et. al., 1998, Blood 92(12):4612-21)) or RetroNectin® (a recombinant human fibronectin fragment; (Clontech Laboratories, Inc., Madison, Wis.).

In particular embodiments for expanding HSPC, the cells are cultured with Delta ligand and 50 ng/ml, of each of SCF and TPO. In particular embodiments for expanding HSPC, the cells are cultured with Delta ligand and preferably 50 ng/ml of each of SCF and Flt-3L. In particular embodiments for expanding HSPC, the cells are cultured with Delta ligand and 50 ng/ml of each of SCF, Flt-3L and TPO. In particular embodiments for expanding HSPC, the cells are cultured with Delta ligand and 50 ng/ml, of each of SCF, Flt-3L, TPO, and IL-6. In particular embodiments, the HSPC are cultured further in the presence of 5 to 15 ng/ml, and preferably 10 ng/ml of IL-3. In particular embodiments, the HSPC are cultured further in the presence of 5 to 15 ng/ml, and preferably 10 ng/ml, GM-CSF. In particular embodiments, the one or more growth factors used is not GM-SCF or IL-7.

In particular embodiments, the percentage of CD34+ cells in the expanded HSPC sample, obtained using the described methods is higher than the percentage of CD34+ cells in the isolated HSPC prior to expansion. In particular embodiments, expansion results in (or more than) a 50-, 75-, 100-150-, 200-, 250-, 300-, 350-, 400-, 450-, 500-, 1000-, 2000-, 3000-, 4000-, 5000-fold increase in the number of HSPC in the expanded sample, relative to the unexpanded sample. In particular embodiments, cell populations are also preferably expanded until a sufficient number of cells are obtained to provide for at least one infusion into a human subject, typically around $10^4$ cells/kg to $10^9$ cells/kg or $2 \times 10^6$ cells/kg subject body weight.

For additional information regarding appropriate culturing and/or expansion conditions, see U.S. Pat. No. 7,399,633; U.S. Patent Publication No. 2010/0183564; Freshney Culture of Animal Cells, Wiley-Liss, Inc., New York, N.Y. (1994)); Varnum-Finney et al., 1993, Blood 101:1784-1789; Delaney et al., 2005, Blood 106:2693-2699; Ohishi et al., 2002, J. Clin. Invest. 110:1165-1174; Delaney et al., 2010, Nature Med. 16(2): 232-236; WO 2006/047569A2; WO 2007/095594A2; U.S. Pat. No. 5,004,681; WO 2011/127470 A1; WO 2011/127472A1; and See Chapter 2 of Regenerative Medicine, Department of Health and Human Services, August 2006, and the references cited therein.

Figure 6B:
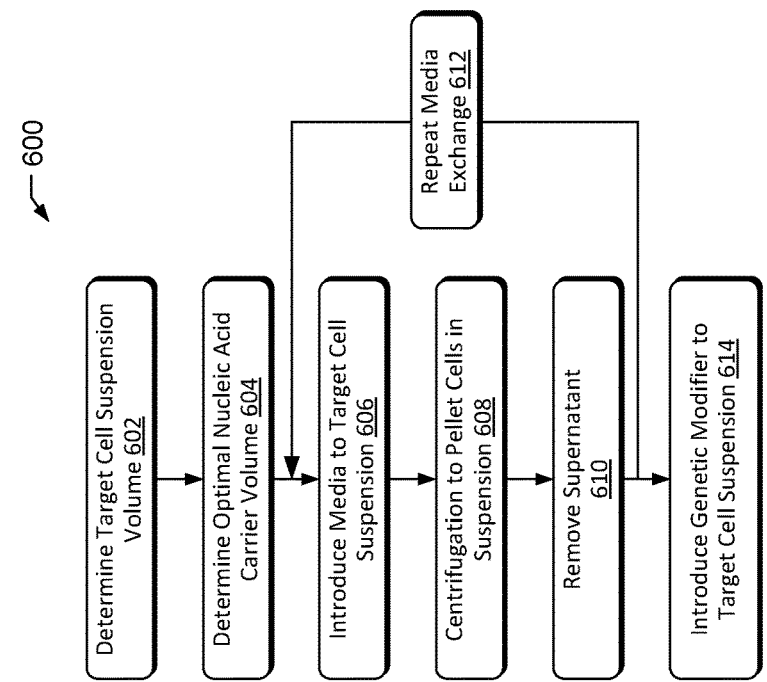
FIG. 6B is a flow chart of an exemplary method for introducing genetic modifications to the selected target cells using the exemplary system of FIG. 6A.
Figure 6A:
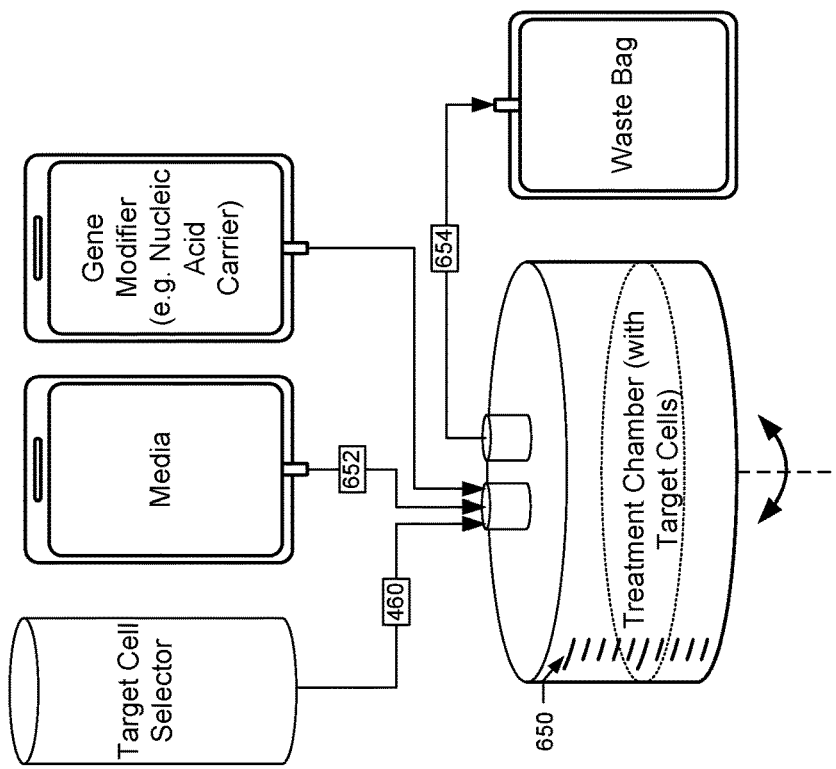
FIG. 6A shows a schematic diagram of an exemplary system for introducing genetic modifiers to target cells to facilitate gene-modification thereof.

Referring now to FIGS. 6A and 6B, once the target cells are transferred back into a treatment chamber (e.g., the first treatment chamber), and expansion has taken place if applicable, method 100 may continue to block 120 at which a desired nucleic acid can be introduced to target cells as indicated by arrow 460.

At block 602, an optimal or desired target cell suspension volume may be determined. For example, the volume of the cell suspension which was transferred to the treatment chamber at arrow 460 may be determined. In particular embodiments, the determination at block 602 is received via a user input. For example, a user may examine the target cell suspension that is in the treatment chamber and estimate its volume. In particular embodiments, the treatment chamber may include a visual aid 650 to assist the user in determining the volume at block 602. For example and with particular reference to FIG. 5A, the visual aid 650 may enable the user to compare the height of the cell suspension (as indicated by the dashed line) with the visual aid 650. Although the visual aid 650 is illustrated in the form of tick-marks, it should be appreciated that the visual aid may take other forms. In particular embodiments, the determination may be made automatically without user input. For example, in embodiments wherein the treatment chamber is configured to perform centrifugation and is equipped with a camera to identify layers formed during centrifugation then the determination at block 602 may be made by centrifuging the cell suspension and identifying a boundary formed between the cell suspension and a gaseous volume of the treatment chamber.

In particular embodiments, the desired target cell suspension volume is independent of the initial volume of the target cell suspension transferred to the treatment chamber at block 460. For example, in particular embodiments a user may specify a desired target cell suspension volume at block 602.

At block 604, an optimal nucleic acid carrier volume may be determined. The optimal nucleic acid carrier volume may be determined based on a target ratio of nucleic acid molecules to target cells. For example, if a target ratio is 20 nucleic acid molecules per target cell then a known or estimated concentration of nucleic acid molecules per unit volume of suspension may be used in conjunction with the volume determination made at block 602 and a known or estimated concentration of target cells per unit volume of target cell suspension to determine the optimal nucleic acid molecule carrier volume at block 604. Ideally, the total volume of carrier should not exceed 30% of the culture volume to avoid cellular toxicity. The user can define the target culture volume to achieve optimal cell concentrations. For CD34+ HSPC, acceptable cell concentrations are 1-2 million cells per mL of culture media and vector volume.

In particular embodiments, the determination of block 602 and/or 604 may occur prior to, simultaneous with, or after the target cell suspension is transferred into the treatment chamber.

At blocks 606 through 610 a media exchange is performed during which one or more volumes of a specified media are introduced to the target cell suspension within the treatment chamber. In particular, at block 606 a first volume of a specified media may be introduced to the target cell suspension as indicated by arrow 652. In particular embodiments, introducing media to the target cell suspension at block 606 may include agitation of the target cell suspension within the media. For example, an agitation action similar to that of block 312 may occur to facilitate sufficient contact between the target cells and the specified media. At block 608, the contents of the treatment chamber including both the target cells and media may be centrifuged to pellet the cells within the suspension. In particular embodiments, the centrifugation at block 608 is performed in a step-wise fashion. At block 608, the formed supernatant may be removed from the treatment chamber. For example, in embodiments wherein the supernatant is substantially includes the specified media, the media may be removed at block 610. In particular embodiments, the removed media is transferred to a waste receptacle to be subsequently discarded as indicated by arrow 654.

At block 612, the media exchange of blocks 606 through 610 may be repeated. In particular embodiments, the media exchange may be performed a plurality of times (e.g., 2, 3, 4, 5, 6, 7, 8, 9, or more than 10 times), e.g. repeated at block 612 twice, prior to introducing any genetic modifiers to the target cell suspension. In particular embodiments, a user-defined final cell suspension volume is obtained. For example, a user may determine and/or define an optimal nucleic acid carrier volume at block 604 which is then obtained during the final performance of block 610.

At block 614, a genetic modifier may be introduced to the target cell suspension. In particular embodiments, the nucleic acid carrier may be introduced directly into the treatment chamber.

Numerous techniques for the introduction of one or more genetic modifiers genetic modifications into cells can be used, provided that the necessary developmental and physiological functions of the recipient cells are not disrupted. See e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92). In particular embodiments, the technique should provide for the stable transfer of nucleic acid to the cell, so that the nucleic acid is expressible by the cell and preferably heritable and expressible by its cell progeny.

Exemplary methods include transfection, electroporation (as described previously), microinjection, liposomes/lipofection (Tarahovsky and Ivanitsky, 1998, *Biochemistry (Mosc)* 63:607-618), ribozymes (Branch and Klotman, 1998, *Exp. Nephrol.* 6:78-83), calcium phosphate mediated transfection, infection with a viral or bacteriophage vector containing the gene sequences, cell fusion, chromosome-mediated gene transfer, microcell-mediated gene transfer, sheroplast fusion, administration of naked DNA, DNA complexes and/or triplex DNA (Chan and Glazer, 1997, *J. Mol. Med.* 75:267-282), transposons/transposases, etc.

Within the treatment chamber, genetic modifications can be induced with a genetic modifier. In the case of naked DNA, DNA complexes and/or triplex DNA, for example, the carrier can be a liquid. As is understood by one of ordinary skill in the art, carriers also include liposomes, vectors, etc. It should be appreciated that, in additional to other genetic modifiers disclosed throughout the disclosure, a genetic modifier may also include one or more of naked DNA, naked mRNA, an adenoviral vector, or an adeno-associated vector, guide RNA (for example, for CRISPR applications), zinc fingers, meganucleases, TALENs, meganuclease-TALEN fusions (megaTALs), and/or genes flanked by regions of homology. Regions of homology may be any suitable length such as, for example, 100 bp to 30,000 bp (e.g., at least 500 bp, at least 1,000 bp, at least 2,000 bp, at least 5,000 bp, at least 10,000 bp, or at least 20,000 bp). Any length suitable to drive integration into the genome of the target cell and resulting genetic modification may be used.

A "vector" is a nucleic acid molecule that is capable of transporting another nucleic acid. Vectors may be, e.g., viruses, phage, a DNA vector, a RNA vector, a viral vector, a bacterial vector, a plasmid vector, a cosmid vector, and an artificial chromosome vector. An "expression vector" is any type of vector that is capable of directing the expression of a protein encoded by one or more genes carried by the vector when it is present in the appropriate environment.

Viral vectors are usually non-replicating or replication-impaired vectors, which means that the viral vector cannot replicate to any significant extent in normal cells (e.g., normal human cells), as measured by conventional means (e.g. via measuring DNA synthesis and/or viral titer). Non-replicating or replication-impaired vectors may have become so naturally (i.e., they have been isolated as such from nature) or artificially (e.g., by breeding in vitro or by genetic manipulation). There will generally be at least one cell-type in which the replication-impaired viral vector can be grown—for example, modified vaccinia Ankara (MVA) can be grown in CEF cells. Typically, viral vectors are incapable of causing a significant infection in a subject, typically in a mammalian subject.

"Retroviruses" are viruses having an RNA genome. In particular embodiments, a retroviral vector contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail regarding retroviral vectors can be found in Boesen, et al., 1994, *Biotherapy* 6:291-302; Clowes, et al., 1994, *J. Clin. Invest.* 93:644-651; Kiem, et al., 1994, *Blood* 83:1467-1473; Salmons and Gunzberg, 1993, *Human Gene Therapy* 4:129-141; Miller, et al., 1993, *Meth. Enzymol.* 217:581-599; and Grossman and Wilson, 1993, *Curr. Opin. in Genetics and Devel.* 3:110-114.

"Gammaretroviruses" refers to a genus of the retroviridae family. Exemplary gammaretroviruses include mouse stem cell virus, murine leukemia virus, feline leukemia virus, feline sarcoma virus, and avian reticuloendotheliosis viruses.

Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., J. Virol. 66:2731-2739, 1992; Johann et al., J. Virol. 66:1635-1640, 1992; Sommerfelt al., Virol. 176:58-59, 1990; Wilson et al., J. Virol. 63:2374-2378, 1989; Miller et al., J. Virol. 65:2220-2224, 1991; and PCT/US94/05700).

Particularly suitable are lentiviral vectors. "Lentivirus" refers to a genus of retroviruses that are capable of infecting dividing and non-dividing cells and typically produce high viral titers. Lentiviral vectors have been employed in gene therapy for a number of diseases. For example, hematopoietic gene therapies using lentiviral vectors or gamma retroviral vectors have been used for x-linked adrenoleukodystrophy and beta thalassaemia. See, e.g., Kohn et al., Clin. Immunol. 135:247-54, 2010; Cartier et al., Methods Enzymol. 507:187-198, 2012; and Cavazzana-Calvo et al., Nature 467:318-322, 2010. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

In particular embodiments, other retroviral vectors can be used in the practice of the methods of the invention. These include, e.g., vectors based on human foamy virus (HFV) or other viruses in the *Spumavirus* genera.

Foamy viruses (FVes) are the largest retroviruses known today and are widespread among different mammals, including all non-human primate species, however are absent in humans. This complete apathogenicity qualifies FV vectors as ideal gene transfer vehicles for genetic therapies in humans and clearly distinguishes FV vectors as gene delivery system from HIV-derived and also gammaretrovirus-derived vectors.

FV vectors are suitable for gene therapy applications because they can (1) accommodate large transgenes (>9 kb), (2) transduce slowly dividing cells efficiently, and (3) integrate as a provirus into the genome of target cells, thus enabling stable long term expression of the transgene(s). FV vectors do need cell division for the pre-integration complex to enter the nucleus, however the complex is stable for at least 30 days and still infective. The intracellular half-life of the FV pre-integration complex is comparable to the one of lentiviruses and significantly higher than for gammaretroviruses, therefore FV are also—similar to LV vectors—able to transduce rarely dividing cells. FV vectors are natural self-inactivating vectors and characterized by the fact that they seem to have hardly any potential to activate neighboring genes. In addition, FV vectors can enter any cells known (although the receptor is not identified yet) and infectious vector particles can be concentrated 100-fold without loss of infectivity due to a stable envelope protein. FV vectors achieve high transduction efficiency in pluripotent hematopoietic stem cells and have been used in animal models to correct monogenetic diseases such as leukocyte adhesion deficiency (LAD) in dogs and Fanconi anemia in mice. FV vectors are also used in preclinical studies of β-thalassemia.

Additional examples of viral vectors include those derived from adenoviruses (e.g., adenovirus 5 (Ad5), adenovirus 35 (Ad35), adenovirus 11 (Ad11), adenovirus 26 (Ad26), adenovirus 48 (Ad48) or adenovirus 50 (Ad50)), adeno-associated virus (AAV; see, e.g., U.S. Pat. No. 5,604,090; Kay et al., Nat. Genet. 24:257 (2000); Nakai et al., Blood 91:4600 (1998)), alphaviruses, cytomegaloviruses (CMV), flaviviruses, herpes viruses (e.g., herpes simplex), influenza viruses, papilloma viruses (e.g., human and bovine papilloma virus; see, e.g., U.S. Pat. No. 5,719,054), poxviruses, vaccinia viruses, etc. See Kozarsky and Wilson, 1993, *Current Opinion in Genetics and Development* 3:499-503, Rosenfeld, et al., 1991, *Science* 252:431-434; Rosenfeld, et al., 1992, *Cell* 68:143-155; Mastrangeli, et al., 1993, *J. Clin. Invest.* 91:225-234; Walsh, et al., 1993, *Proc. Soc. Exp. Biol. Med.* 204:289-300; and Lundstrom, 1999, *J. Recept. Signal Transduct. Res.* 19: 673-686. Examples include modified vaccinia Ankara (MVA) and NYVAC, or strains derived therefrom. Other examples include avipox vectors, such as a fowlpox vectors (e.g., FP9) or canarypox vectors (e.g., ALVAC and strains derived therefrom).

Other methods of gene delivery include use of artificial chromosome vectors such as mammalian artificial chromosomes (Vos, 1998, *Curr. Op. Genet. Dev.* 8:351-359) and yeast artificial chromosomes (YAC). YAC are typically used when the inserted nucleic acids are too large for more conventional vectors (e.g., greater than 12 kb).

Vectors and other methods to deliver nucleic acids can include regulatory sequences to control the expression of the nucleic acid molecules. These regulatory sequences can be eukaryotic or prokaryotic in nature. In particular embodiments, the regulatory sequence can be a tissue specific promoter such that the expression of the one or more therapeutic proteins will be substantially greater in the target tissue type compared to other types of tissue. In particular embodiments, the regulatory sequence can result in the constitutive expression of the one or more therapeutic proteins upon entry of the vector into the cell. Alternatively, the regulatory sequences can include inducible sequences. Inducible regulatory sequences are well known to those skilled in the art and are those sequences that require the presence of an additional inducing factor to result in expression of the one or more therapeutic proteins. Examples of suitable regulatory sequences include binding sites corresponding to tissue-specific transcription factors based on endogenous nuclear proteins, sequences that direct expression in a specific cell type, the lac operator, the tetracycline operator and the steroid hormone operator. Any inducible regulatory sequence known to those of skill in the art may be used.

In particular embodiments, the nucleic acid is stably integrated into the genome of a cell. In particular embodiments, the nucleic acid is stably maintained in a cell as a separate, episomal segment.

In particular embodiments, the efficiency of integration, the size of the DNA sequence that can be integrated, and the number of copies of a DNA sequence that can be integrated into a genome can be improved by using transposons. Transposons or transposable elements include a short nucleic acid sequence with terminal repeat sequences upstream and downstream. Active transposons can encode enzymes that facilitate the excision and insertion of nucleic acid into a target DNA sequence.

A number of transposable elements have been described in the art that facilitate insertion of nucleic acids into the genome of vertebrates, including humans. Examples include sleeping beauty (e.g., derived from the genome of salmonid fish); piggyback (e.g., derived from lepidopteran cells and/or the *Myotis lucifugus*); mariner (e.g., derived from *Drosophila*); frog prince (e.g., derived from *Rana pipiens*); Tol2 (e.g., derived from medaka fish); TcBuster (e.g., derived from the red flour beetle *Tribolium castaneum*) and spinON. CRISPR-Cas systems may also be used. Exemplary description of computer-executable instructions are denoted herein as SW6 and are described as follows in Table 4:

TABLE 4

Exemplary description of computer-executable nucleic acid introduction instructions.

SW 6. Description 1. This program is suitable for initiating viral vector transduction or media exchange and liquid component addition to any cell product.
SW 6. Description 2. This program is suitable for initiating viral vector transduction or media exchange and liquid component addition to any cell product. Once media exchange is completed, virus vector or additional liquid component is added to the cell suspension in the chamber.
SW 6. Description 3. This program is suitable for initiating viral vector transduction or media exchange and liquid component addition to any cell product. The program initiates with the assumption that the cell fraction to be transduced/media exchanged is in a Target Cell Bag included in the pre-fabricated tubing set. First the cell suspension is transferred from the Target Cell Bag to the device chamber. Media exchange is then performed dilution of the cell suspension with media for media exchange, then step-wise centrifugation to pellet cells in suspension, and finally removal of supernatant volume. Once media exchange is completed, virus vector or additional liquid component is added to the cell suspension.
SW 6. Description 4. This program is suitable for initiating viral vector transduction or media exchange and liquid component addition to any cell product. The program initiates with the assumption that the cell fraction to be transduced/media exchanged is in a Target Cell Bag included in the pre-fabricated tubing set. First the cell suspension is transferred from the Target Cell Bag to the device chamber. Media exchange is then performed by three cycles of the following: dilution of the cell suspension to the maximum chamber volume with media specified for media exchange, then step-wise centrifugation to pellet cells in suspension, and finally removal of maximum supernatant volume. During the final supernatant removal, the final cell suspension volume is obtained. Once media exchange is completed, virus vector or additional liquid component is added to the cell suspension in the chamber.
SW6 Description 5 (also referred to herein as J6). This program is suitable for initiating viral vector transduction or media exchange and liquid component addition to any cell product. The program initiates with the assumption that the cell fraction to be transduced/media exchanged is in the Target Cell Bag included in the pre-fabricated tubing set. The user specifies the volume of the final desired cell suspension and the volume of virus vector or other liquid component to be added to the cell suspension. First the cell suspension is transferred from the Target Cell Bag to the device chamber and the Target Cell Bag is rinsed with media specified for media exchange. Bag rinse is also transferred to the chamber. Media exchange is then performed by three cycles of the following: dilution of the cell suspension to the maximum chamber volume with media specified for media exchange, then step-wise centrifugation to pellet cells in suspension, and finally removal of maximum supernatant volume. During the final supernatant removal, the user-defined final cell suspension volume is obtained. Once media exchange is completed, virus vector or additional liquid component is added to the cell suspension in the chamber.

Referring now back to FIG. 1, the method 100 may further include a sequential addition of one or more additional liquid components to the target cell suspension at block 122. In particular embodiments, the one or more additional liquid components may include at least one of a second volume of nucleic acid carrier, a second volume of buffer, an additional media component not previously added, or a second volume of media, e.g. transduction media. In particular embodiments, the sequential addition at block 122 may be performed within the treatment chamber. For example, a user may specify a volume corresponding to each additional liquid component to be added to the cell suspension and, based on the user input, tubing paths may be cleared, e.g. to prevent contamination, and/or the specified volume of each component may be added to the treatment chamber. In particular embodiments, the sequential addition at block 122 may be performed outside the treatment chamber, e.g. within the CCS-GMI 800 or the cell separator and/or electroporator 1100. For example, following the introduction of the nucleic acid carrier to the target cells in the CCS-GMI 800 at block 512, the target cells may be maintained within the CCS-GMI 800 while a sequential addition of a liquid component is added at block 122. In particular embodiments, target cell expansion and/or stimulation may be performed following blocks 120 and/or 122. Exemplary description of computer-executable instructions are denoted herein as SW7 and are described as follows in Table 5:

TABLE 5

Exemplary description of computer-executable liquid addition instructions.

SW7 Description 1. This program is suitable for addition of any two liquid components to a cell suspension.
SW7 Description 2. This program is suitable for addition of any two liquid components to a cell suspension. The program may initiate with the assumption that the cell suspension for component addition is in the device chamber. The device then adds a volume of each component to the device chamber.
SW7 Description 3. This program is suitable for addition of any two liquid components to a cell suspension. The program may initiate with the assumption that the cell suspension for component addition is in the device chamber. The device then sequentially adds a specified volume of each component to the device chamber.
SW7 Description 4. This program is suitable for sequential addition of any two liquid components to a cell suspension. The program may initiate with the assumption that the cell suspension for component addition is in the device chamber. The user specifies the desired volume of each liquid component to add to the cell suspension. The device then sequentially adds the specified volume of each component to the device chamber.
SW7 Description 5 (also referred to herein as J7). This program is suitable for sequential addition of any two liquid components to a cell suspension. One example of a two-component addition would be the addition of a second volume of virus vector and additional transduction media during a two-hit cell transduction method. The program may initiate with the assumption that the cell suspension for component addition is in the device chamber. The user specifies the desired volume of each liquid component to add to the cell suspension. The device first clears the tubing path from the components to the chamber to prevent unwanted contamination. The device then sequentially adds the specified volume of each component to the device chamber and gently mixes the contents.

At various stages during the described methods, it may be helpful or necessary to culture the targeted cells. For example, as the nucleic acid introduction process may be stressful, resulting gene-modified target cells may undergo cell culture procedures to allow them to re-gain health and/or begin proliferation before purification and formulations. Moreover, in particular embodiments, the target cells may undergo culturing prior to the nucleic acid introduction process, e.g. to bolster their health before the process. Accordingly, method 100 may also include culturing of the target cell product at block 124.

In particular embodiments, culturing the cell product at block 124 may include determining one or more gas parameters corresponding to at least one gas to expose to the cell product. For example, the system may include one or more gas cylinders connected to the treatment chamber and for which individual partial pressures may be independently regulated via one or more gas regulators (e.g. illustrated in FIG. 7A). Accordingly, in particular embodiments, the gas regulator(s) may selectively control a first partial pressure of a first gas up through an N-th partial pressure of an N-th gas. In particular embodiments, a partial pressure corresponding to each of nitrogen gas ($N_2$), carbon dioxide gas ($CO_2$), and oxygen gas ($O_2$) may be regulated during the culturing of the cell product at block 124. Moreover, in particular embodiments, culturing the cell product may include determining an optimal treatment chamber temperature at block 704. One of skill in the art will realize that both the optimal gas parameters and the optimal temperature for culturing will vary depending on the type of cell product and stage of the process. In particular embodiments, the treatment chamber may be maintained at the optimal temperature at block 706. Any suitable technique for maintaining the treatment temperature, whether now known or subsequently developed, may be used.

At block 708, one or more gases may be mixed according to the determining gas parameters at block 702. In particular embodiments, the gases may be mixed within the treatment chamber, e.g. each gas is individually introduced into the treatment chamber. In particular embodiments, the gases may be mixed external to the treatment chamber. It may be preferable to mix the gases external to the treatment chamber in a separate mixing device in order to more accurately obtain respective partial pressures for each gas. At block 710, the gas mixture may be periodically exchanged during the culturing of the cell product. For example, in particular embodiments the gas mixture is completely exchanged at regular intervals, e.g. 15 minutes, for one or more of a predetermined time period or until a user terminates the cell culturing at block 124. Exemplary description of computer-executable instructions are denoted herein as SW8 and are described as follows in Table 6:

TABLE 6

Exemplary description of computer-executable cell culture instructions.

SW8 Description 1. This program is suitable for culture of any cell product.
SW8 Description 2. This program is suitable for culture of any cell product in the device chamber. The program initiates with the assumption that the cells to be cultured are already formulated for culture and are present in the device chamber. The program can define the gas parameters of $N_2$, $CO_2$ and $O_2$, as well as the chamber temperature or can define subsets of these parameters based on user input. The device maintains the chamber to the desired temperature and creates the appropriate gas formulation for the chamber.
SW8 Description 3. This program is suitable for culture of any cell product in the device chamber. The program initiates with the assumption that the cells to be cultured are already formulated for culture and are present in the device chamber. The program allows the user to define the gas parameters of $N_2$, $CO_2$ and $O_2$, as well as the chamber temperature. The program also gives the user the option to have the cell suspension gently mixed during the incubation period. The device heats the chamber to the desired temperature and mixes the appropriate gas formulation for the chamber. The cultured cell suspension remains in the device chamber upon program termination.
SW8 Description 4. This program is suitable for culture of any cell product in the device chamber. The program can define or allows the user to define the gas parameters of $N_2$, $CO_2$ and $O_2$, as well as the chamber temperature. The program also gives the user the option to have the cell suspension gently mixed during the incubation period. The device heats the chamber to the desired temperature and mixes the appropriate gas formulation for the chamber. The cultured cell suspension remains in the device chamber upon program termination.
SW8 Description 5 (also referred to herein as J8). This program is suitable for culture of any cell product in the device chamber. The program initiates with the assumption that the cells to be cultured are already formulated for culture and are present in the device chamber. The program allows the user to define the gas parameters of $N_2$, $CO_2$ and $O_2$, as well as the chamber temperature. The program also gives the user the option to have the cell suspension gently mixed once every 30 minutes during the incubation period. The device heats the chamber to the desired temperature and mixes the appropriate gas formulation for injection into the chamber. Once the appropriate gas formulation is achieved, the gas mix is injected into the chamber. The device continues the incubation at temperature with a complete gas exchange of the chamber every 15 minutes and mixing as specified until the user terminates the program. The cultured cell suspension remains in the device chamber upon program termination.

Figure 7B:
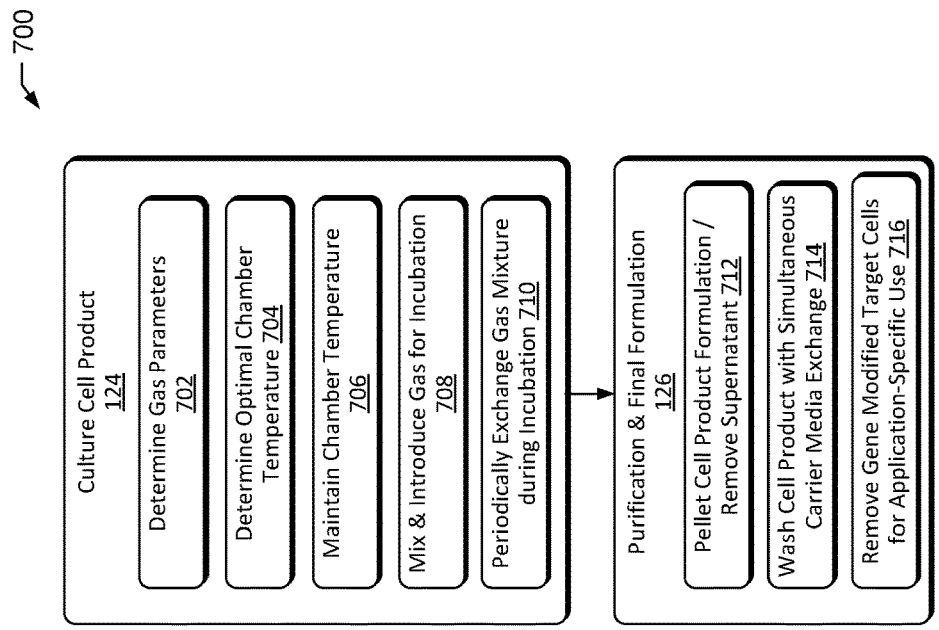
FIG. 7B is a flow chart of an exemplary method for culturing, purifying, and formulating the gene-modified cells using the exemplary system of FIG. 7A.
Figure 7A:
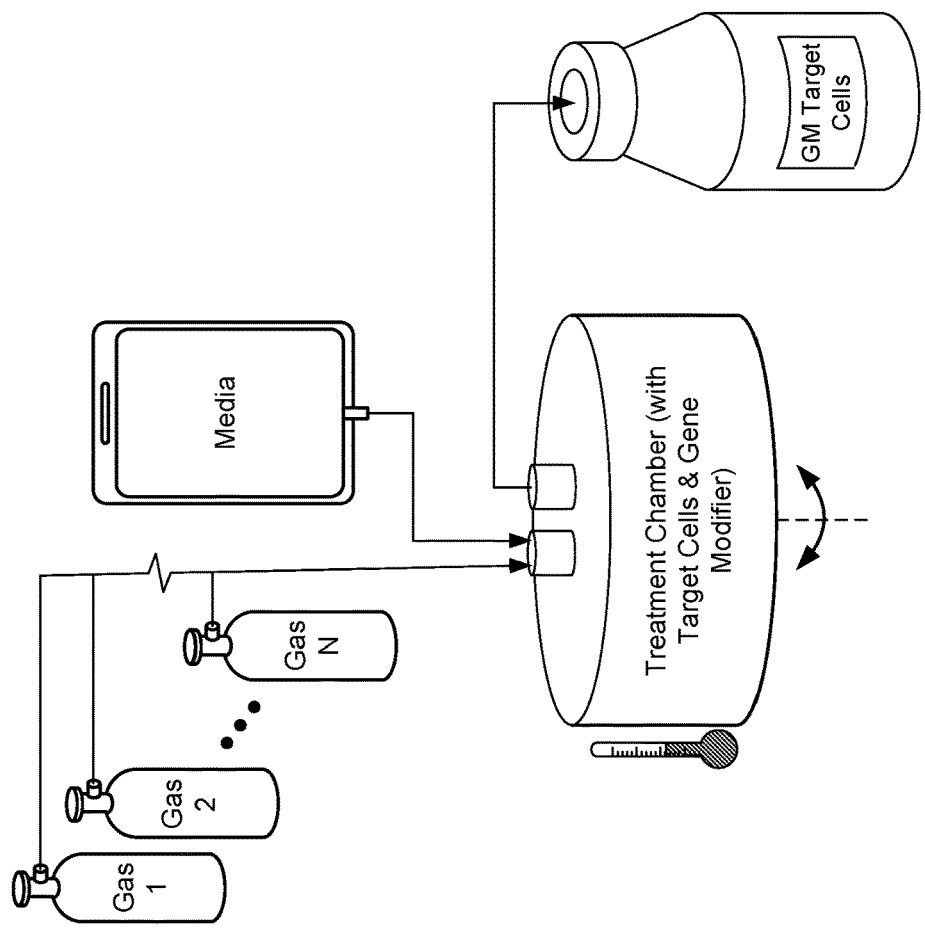
FIG. 7A shows a schematic diagram of an exemplary system for culturing, purifying, and formulating gene-modified cells for application-specific use, e.g. administering the gene-modified cells to a subject.

Corresponding to blocks 124 and 126, FIG. 7A shows a schematic diagram of an exemplary system for culturing, purifying, and formulating gene-modified cells for application-specific use, e.g. administering the gene-modified cells to a subject. FIG. 7B is a flow chart of an exemplary method for culturing, purifying, and formulating the gene-modified cells using the exemplary system of FIG. 7A.

In particular embodiments, the purification and final formulation of the cell product at block 126 may include removing unwanted media components from the final formulation. For example, cells and genetically-modified target cells can be purified and formulated for administration to a subject within the POCD. A formulation refers to a cell or modified cell prepared with a pharmaceutically acceptable carrier for administration to a subject. Exemplary carriers and modes of administration of cells are described at pages 14-15 of U.S. Patent Publication No. 2010/0183564. Additional pharmaceutical carriers are described in Remington: The Science and Practice of Pharmacy, 21st Edition, David B. Troy, ed., Lippicott Williams & Wilkins (2005).

In particular embodiments, purification and final formulation at block 126 includes pelleting the cell product and removing the resulting supernatant. Removal of the resulting supernatant may be beneficial as it may remove any remaining nucleic acid carrier and/or nucleic acid carrier, e.g. viral vectors which could inadvertently be administered to a patient. It should be appreciated that an appropriate media for culturing purposes may be different than an appropriate media for administration purposes. Accordingly, in particular embodiments, genetically-modified cells can be purified from a culture medium, and washed and concentrated into a carrier in a therapeutically-effective amount at block 714. Exemplary carriers include saline, buffered saline, physiological saline, water, Hanks' solution, Ringer's solution, Nonnosol-R (Abbott Labs), Plasma-Lyte A® (Baxter Laboratories, Inc., Morton Grove, Ill.), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, formulations can include a local anesthetic such as lidocaine to ease pain at a site of injection.

Therapeutically effective amounts of cells within formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml.

The formulations disclosed herein can be prepared for administration by, for example, injection, infusion, perfusion, or lavage.

At block 716, the formulated gene modified product may be removed from the treatment chamber for application specific use. For example, the gene modified product may be transferred to a vial from which a syringe may be loaded for subject administration. The compositions and formulations disclosed herein can be prepared for administration by, for example, injection, infusion, perfusion, or lavage. Exemplary description of computer-executable instructions are denoted herein as SW9 and are described as follows in Table 7:

TABLE 7

Exemplary description of computer-executable purification (e.g., harvest) and formulation instructions SW9 Description 1. This program is suitable for harvest and/or final formulation of any cell product in the chamber of the device.
SW9 Description 2. This program is suitable for harvest and final formulation of any cell product in the chamber of the device. The program initiates with the assumption that the cell suspension to be harvested and formulated is in the device chamber. The program removes unwanted media components from the final formulation. First, the cell suspension in the chamber is centrifuged in a step-wise manner to pellet cells. Once pelleted, supernatant is removed. After initial supernatant removal, washes with media exchange are accomplished. Following the final wash/media exchange, additional supernatant is removed. The formulated cell product is transferred from the device chamber for removal.
SW9 Description 3. This program is suitable for harvest and final formulation of any cell product in the chamber of the device. The program initiates with the assumption that the cell suspension to be harvested and formulated is in the device chamber. The volume of the initial cell suspension supernatant for transfer to sufficiently remove unwanted media components from the final formulation is identified. First, the cell suspension in the chamber is centrifuged in a step-wise manner to pellet cells. Once pelleted, the identified supernatant volume is removed. After initial supernatant removal, washes with media exchange are accomplished as follows: first, the pelleted cell suspension is diluted with final formulation media, then cell suspension is centrifuged in a step-wise manner to pellet cells. Once pelleted, a supernatant volume is removed. Following the final wash/media exchange, additional supernatant is removed to bring the final cell product formulation to a total volume. The formulated cell product is transferred from the device chamber to the Target Cell Bag attached to the device for removal and application-specific use.
SW9 Description 4. This program is suitable for harvest and final formulation of any cell product in the chamber of the device. The program initiates with the assumption that the cell suspension to be harvested and formulated is in the device chamber. The user specifies the volume of the initial cell suspension supernatant for transfer to sufficiently remove unwanted media components from the final formulation. First, the cell suspension in the chamber is centrifuged to pellet cells. Once pelleted, the specified supernatant volume is removed. After initial supernatant removal, washes with simultaneous TABLE 7-continued Exemplary description of computer-executable purification (e.g., harvest) and formulation instructions media exchange are accomplished as follows: first, the pelleted cell suspension is diluted to a volume with final formulation media, then cell suspension is centrifuged in a step-wise manner to pellet cells. Once pelleted, a preset supernatant volume is removed. Following the final wash/media exchange, additional supernatant is removed to bring the final cell product formulation to a total volume. The formulated cell product is transferred from the device chamber to the Target Cell Bag attached to the device for removal and application-specific use.
SW9 Description 5 (also referred to herein as J9). This program is suitable for harvest and final formulation of any cell product in the chamber of the device. The program initiates with the assumption that the cell suspension to be harvested and formulated is in the device chamber. The user specifies the volume of the initial cell suspension supernatant for transfer to sufficiently remove unwanted media components from the final formulation. First, the cell suspension in the chamber is centrifuged in a step-wise manner to pellet cells. Once pelleted, the specified supernatant volume is removed. After initial supernatant removal, three washes with simultaneous media exchange are accomplished as follows: first, the pelleted cell suspension is diluted to the maximum chamber volume with final formulation media, then cell suspension is centrifuged in a step-wise manner to pellet cells. Once pelleted, a preset supernatant volume is removed. Following the final wash/media exchange, additional supernatant is removed to bring the final cell product formulation to a total volume of 45 mL. The formulated cell product is transferred from the device chamber to the Target Cell Bag attached to the device for removal and application-specific use.

Referring back now to FIG. 2A, it should be appreciated that any of the exemplary systems and/or devices disclosed herein may be in communication with a platform controller 264 which may control any of the operations of methods 100, 200, 300, 400, 500, 600, and/or 700, or any subset thereof. The platform controller 264 may include one or more processor(s) 266 and/or one or more computer readable media 268. The computer readable media 268 may include volatile storage (e.g., random-access memory) and/or non-volatile memory (e.g., a hard disk or another type of non-volatile memory). The computer readable media 268 may be used to store software instructions 270, such as device drivers, an operating system, and/or software applications that are executable by the processors 266 to perform various functions.

In particular embodiments, the computer readable media 268 may include a valve controller 272 to selectively toggle one or more valves (denoted by valve symbol ⋈) for opening and/or closing one or more fluid paths. In particular embodiments, the computer readable media 268 may include a pump controller 274 to selectively operate one or more pumps (denoted by pump symbol ⊖) for forcibly perusing a sample or portion thereof through one or more fluid paths. Although the valve symbols and pump symbols are shown on but a few of the many flow paths illustrated in the figures, it should be appreciated that it is within the scope of the present disclosure that a valve and/or pump be included on any one of the flow paths and/or sections of tubing used to create the flow paths. More detail regarding appropriate types of valves and pumps used in particular embodiments may be found in U.S. patents: U.S. Pat. Nos. 5,691,208; 6,468,432; and 8,727,132.

In particular embodiments, the computer readable media 268 may include a treatment chamber controller 276 to control one or more functionalities of the treatment chamber. For example, in particular embodiments wherein the treatment chamber is configured to perform centrifugation, the treatment chamber controller 276 may be configured to control one or more of centrifugation speed (e.g. RPMs), an agitation schedule (e.g. duration and intensity of agitation), and/or one or more internal valves for removing supernatant. In particular embodiments, the treatment chamber controller 276 may be configured to control one or more heating and/or cooling elements used to maintain one or more incubation environments within the treatment chamber.

In particular embodiments, the computer readable media 268 may include a target cell selector and/or combination cell selector & nucleic acid introducer (TCS/CCS-NAI) controller 278. The TCS/CCS-NAI controller 278 may be configured to control performance of one more functionalities disclosed herein with relation to the target cell selector of FIG. 4A (e.g. a MACS or FACS based cell selector) and/or the CCS-NAI 800 and/or the cell separator and/or electroporator 1100. For example, the TCS/CCS-NAI controller 278 may be configured to control the CCS-NAI 800 during sequential performance of a MACS protocol followed by an electroporation protocol of selected cells maintained within the CCS-NAI 800.

Methods disclosed herein include producing cells for and/or treating subjects (humans, veterinary animals (dogs, cats, reptiles, birds, etc.), livestock (horses, cattle, goats, pigs, chickens, etc.), and research animals (monkeys, rats, mice, fish, etc.) with genetically-modified cells disclosed herein. Treating subjects includes delivering therapeutically effective amounts. Therapeutically effective amounts include those that provide effective amounts, prophylactic treatments, and/or therapeutic treatments.

An "effective amount" is the number of cells necessary to result in a desired physiological change in a subject. Effective amounts are often administered for research purposes.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition.

A "therapeutic treatment" includes a treatment administered to a subject who displays symptoms or signs of a condition and is administered to the subject for the purpose of reducing the severity or progression of the condition.

The actual dose amount administered to a particular subject can be determined by a physician, veterinarian, or researcher taking into account parameters such as physical and physiological factors including target; body weight; type of condition; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$. In particular embodiments, a minimum dose is $2 \times 10^6$ cells/kg subject body weight.

As indicated, the compositions and formulations disclosed herein can be administered by, for example, injection, infusion, perfusion, or lavage and can more particularly include administration through one or more bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous infusions and/or bolus injections.

Any nucleic acid including a therapeutic gene can be introduced into target cells disclosed herein. The term "gene" refers to a nucleic acid sequence (used interchangeably with polynucleotide or nucleotide sequence) that encodes one or more therapeutic proteins as described herein. This definition includes various sequence polymorphisms, mutations, and/or sequence variants wherein such alterations do not substantially affect the function of the encoded one or more therapeutic proteins. The term "gene" may include not only coding sequences but also regulatory regions such as promoters, enhancers, and termination regions. The term further can include all introns and other DNA sequences spliced from the mRNA transcript, along with variants resulting from alternative splice sites. Gene sequences encoding the molecule can be DNA or RNA that directs the expression of the one or more therapeutic proteins. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type.

A gene sequence encoding one or more therapeutic proteins can be readily prepared by synthetic or recombinant methods from the relevant amino acid sequence. In particular embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In particular embodiments, the gene sequence encoding the sequences can be codon optimized for expression in mammalian cells.

As one example, a gene can be selected to provide a therapeutically effective response against a condition that, in particular embodiments, is inherited. In particular embodiments, the condition can be Grave's Disease, rheumatoid arthritis, pernicious anemia, Multiple Sclerosis (MS), inflammatory bowel disease, systemic lupus erythematosus (SLE), adenosine deaminase deficiency (ADA-SCID) or severe combined immunodeficiency disease (SCID), Wiskott-Aldrich syndrome (WAS), chronic granulomatous disease (CGD), Fanconi anemia (FA), Battens disease, adrenoleukodystrophy (ALD) or metachromatic leukodystrophy (MLD), muscular dystrophy, pulmonary aveolar proteinosis (PAP), pyruvate kinase deficiency, Shwachmann-Diamond-Blackfan anemia, dyskeratosis congenita, cystic fibrosis, Parkinson's disease, Alzheimer's disease, or amyotrophic lateral sclerosis (Lou Gehrig's disease). In particular embodiments, depending on the condition, the therapeutic gene may be a gene that encodes a protein and/or a gene whose function has been interrupted. Exemplary therapeutic gene and gene products include: soluble CD40; CTLA; Fas L; antibodies to CD4, CD5, CD7, CD52, etc.; antibodies to IL1, IL2, IL6; an antibody to TCR specifically present on autoreactive T cells; IL4; IL10; IL12; IL13; IL1Ra, sIL1RI, sIL1RII; sTNFRI; sTNFRII; antibodies to TNF; P53, PTPN22, and DRB1*1501/DQB1*0602; globin family genes; WAS; phox; FANC family genes; dystrophin; pyruvate kinase; CLN3; ABCD1; arylsulfatase A; SFTPB; SFTPC; NLX2.1; ABCA3; GATA1; ribosomal protein genes; TERT; TERC; DKC1; TINF2; CFTR; LRRK2;

PARK2; PARK7; PINK1; SNCA; PSEN1; PSEN2; APP; SOD1; TDP43; FUS; ubiquilin 2; and/or C9ORF72. Therapeutically effective amounts may provide function to immune and other blood cells and/or microglial cells or may alternatively—depending on the treated condition—inhibit lymphocyte activation, induce apoptosis in lymphocytes, eliminate various subsets of lymphocytes, inhibit T cell activation, eliminate or inhibit autoreactive T cells, inhibit Th-2 or Th-1 lymphocyte activity, antagonize IL1 or TNF, reduce inflammation, induce selective tolerance to an inciting agent, reduce or eliminate an immune-mediated condition; and/or reduce or eliminate a symptom of the immune-mediated condition. Therapeutic effective amounts may also provide functional DNA repair mechanisms; surfactant protein expression; telomere maintenance; lysosomal function; breakdown of lipids or other proteins such as amyloids; permit ribosomal function; and/or permit development of mature blood cell lineages which would otherwise not develop such as macrophages other white blood cell types.

As another example, a gene can be selected to provide a therapeutically effective response against diseases related to red blood cells and clotting. In particular embodiments, the disease is a hemoglobinopathy like thalassemia, or a sickle cell disease/trait. The therapeutic gene may be, for example, a gene that induces or increases production of hemoglobin; induces or increases production of beta-globin, or alpha-globin; or increases the availability of oxygen to cells in the body. The therapeutic gene may be, for example, HBB or CYB5R3. Exemplary effective treatments may, for example, increase blood cell counts, improve blood cell function, or increase oxygenation of cells in patients. In another particular embodiment, the disease is hemophilia. The therapeutic gene may be, for example, a gene that increases the production of coagulation/clotting factor VIII or coagulation/clotting factor IX, causes the production of normal versions of coagulation factor VIII or coagulation factor IX, a gene that reduces the production of antibodies to coagulation/clotting factor VIII or coagulation/clotting factor IX, or a gene that causes the proper formation of blood clots. Exemplary therapeutic genes include F8 and F9. Exemplary effective treatments may, for example, increase or induce the production of coagulation/clotting factors VIII and IX; improve the functioning of coagulation/clotting factors VIII and IX, or reduce clotting time in subjects.

As another example, a gene can be selected to provide a therapeutically effective response against a lysosomal storage disorder. In particular embodiments, the lysosomal storage disorder is mucopolysaccharidosis (MPS), type I; MPS II or Hunter Syndrome; MPS III or Sanfilippo syndrome; MPS IV or Morquio syndrome; MPS V; MPS VI or Maroteaux-Lamy syndrome; MPS VII or sly syndrome; alpha-mannsidosis; beta-mannosidosis; glycogen storage disease type I, also known as GSDI, von Gierke disease, or Tay Sachs; Pompe disease; Gaucher disease; Fabry disease. The therapeutic gene may be, for example a gene encoding or inducing production of an enzyme, or that otherwise causes the degradation of mucopolysaccharides in lysosomes. Exemplary therapeutic genes include IDUA or iduronidase, IDS, GNS, HGSNAT, SGSH, NAGLU, GUSB, GALNS, GLB1, ARSB, and HYAL1. Exemplary effective genetic therapies for lysosomal storage disorders may, for example, encode or induce the production of enzymes responsible for the degradation of various substances in lysosomes; reduce, eliminate, prevent, or delay the swelling in various organs, including the head (exp. Macrosephaly), the liver, spleen, tongue, or vocal cords; reduce fluid in the brain; reduce heart valve abnormalities; prevent or dilate narrowing airways and prevent related upper respiratory conditions like infections and sleep apnea; reduce, eliminate, prevent, or delay the destruction of neurons, and/or the associated symptoms.

As another example, a gene can be selected to provide a therapeutically effective response against a hyperproliferative disease. In particular embodiments, the hyperproliferative disease is cancer. The therapeutic gene may be, for example, a tumor suppressor gene, a gene that induces apoptosis, a gene encoding an enzyme, a gene encoding an antibody, or a gene encoding a hormone. Exemplary therapeutic genes and gene products include 101F6, 123F2 (RASSF1), 53BP2, abl, ABLI, ADP, aFGF, APC, ApoAI, ApoAIV, ApoE, ATM, BAI-1, BDNF, Beta*(BLU), bFGF, BLC1, BLC6, BRCA1, BRCA2, CBFA1, CBL, C-CAM, CFTR, CNTF, COX-1, CSFIR, CTS-1, cytosine deaminase, DBCCR-1, DCC, Dp, DPC-4, E1A, E2F, EBRB2, erb, ERBA, ERBB, ETS1, ETS2, ETV6, Fab, FCC, FGF, FGR, FHIT, fms, FOX, FUS 1, FUS1, FYN, G-CSF, GDAIF, Gene 21 (NPRL2), Gene 26 (CACNA2D2), GM-CSF, GMF, gsp, HCR, HIC-1, HRAS, hst, IGF, IL-1, IL-2, IL-3, IL-4, IL-5, IL-6, IL-7, IL-8, IL-9, IL-10, IL-11 IL-12, ING1, interferon α, interferon β, interferon γ, IRF-1, JUN, KRAS, LCK, LUCA-1 (HYAL1), LUCA-2 (HYAL2), LYN, MADH4, MADR2, MCC, mda7, MDM2, MEN-I, MEN-II, MLL, MMAC1, MYB, MYC, MYCL1, MYCN, neu, NF-1, NF-2, NGF, NOEY1, NOEY2, NRAS, NT3, NT5, OVCA1, p16, p21, p27, p53, p57, p73, p300, PGS, PIM1, PL6, PML, PTEN, raf, Rap1A, ras, Rb, RB1, RET, rks-3, ScFv, scFV ras, SEM A3, SRC, TALI, TCL3, TFPI, thrombospondin, thymidine kinase, TNF, TP53, trk, T-VEC, VEGF, VHL, WT1, WT-1, YES, and zac1. Exemplary effective genetic therapies may suppress or eliminate tumors, result in a decreased number of cancer cells, reduced tumor size, slow or eliminate tumor growth, or alleviate symptoms caused by tumors.

As another example, a gene can be selected to provide a therapeutically effective response against an infectious disease. In particular embodiments, the infectious disease is human immunodeficiency virus (HIV). The therapeutic gene may be, for example, a gene rendering immune cells resistant to HIV infection, or which enables immune cells to effectively neutralize the virus via immune reconstruction, polymorphisms of genes encoding proteins expressed by immune cells, genes advantageous for fighting infection that are not expressed in the patient, genes encoding an infectious agent, receptor or coreceptor; a gene encoding ligands for receptors or coreceptors; viral and cellular genes essential for viral replication including; a gene encoding ribozymes, antisense RNA, small interfering RNA (siRNA) or decoy RNA to block the actions of certain transcription factors; a gene encoding dominant negative viral proteins, intracellular antibodies, intrakines and suicide genes. Exemplary therapeutic genes and gene products include α2β1; αvβ3; αvβ5; αvβ63; BOB/GPR15; Bonzo/STRL-33/TYM-STR; CCR2; CCR3; CCR5; CCR8; CD4; CD46; CD55; CXCR4; aminopeptidase-N; HHV-7; ICAM; ICAM-1; PRR2/HveB; HveA; α-dystroglycan; LDLR/α2MR/LRP; PVR; PRR1/HveC; and laminin receptor. A therapeutically effective amount for the treatment of HIV, for example, may increase the immunity of a subject against HIV, ameliorate a symptom associated with AIDS or HIV, or induce an innate or adaptive immune response in a subject against HIV. An immune response against HIV may include antibody production and result in the prevention of AIDS and/or ameliorate a symptom of AIDS or HIV infection of the subject, or decrease or eliminate HIV infectivity and/or virulence.

Bacteria are also encompassed in the term infectious agent. Other infectious agents include, for example, parasites such as members of the *Plasmodium* genus, the agent that causes malaria. Exemplary therapeutic genes affecting the infectivity of parasites include erythrocyte skeletal protein 4.1, glycophorin, p55, and the Duffy allele, which encodes a chemokine receptor. Therapeutically effective amounts will, for example, reduce or eliminate the infectious disease or agent. They may also reduce or eliminate a symptom of the infectious disease or agent.

The genetically-modified cell can be any cell type capable of ex vivo isolation, modification and formulation as described herein. Exemplary cell types include HSPC positive for one or more of CD34, CD43, CD45RO, CD45RA, CD59, CD90, CD109, CD117, CD133, CD166, HLA D or negative for Lin or CD38; T cells (e.g., αβ T cells, γδ Tcells, mature T cells (e.g., CD3+), activated T cells (e.g., 4-1BB+ (CD137+)), helper T cells (e.g., CD4+), cytotoxic T-cells (e.g., CD8+), central memory T-cells ($T_{CM}$, e.g., CD62L+ CD25+, CD127+, or CCR7+ and CD45RO+/CD45RA- as compared to naive cells), effector memory T cells ($T_{EM}$, e.g., CD62L-, CD45RA- as compared to a naive cell), regulatory T cells ($T_{REG}$, e.g., CD25+, CTLA-4+, GITR+, GARP+ and LAP+), naive T-cells (e.g., non-antigen experienced T cell that expresses CD62L and CD45RA, and does not express CD45RO as compared to central or effector memory cells), natural killer cells (also known as NK cells, K cells, and killer cells, e.g., CD8+, CD16+, CD56+, CD3-, macrophages, monocytes, B cells, among others.

Exemplary Kits: Also disclosed herein are kits including one or more containers including materials necessary or helpful to practice the platforms disclosed herein. Associated with such container(s) can be a notice in the form prescribed by a governmental agency regulating the manufacture, use, or sale of pharmaceuticals or biological products, which notice reflects approval by the agency of manufacture, use, or sale for human administration.

Optionally, the kits described herein further include instructions for using the kit in the technologies disclosed herein. In various embodiments, the kit may include instructions regarding sample processing; software program use; user interface guidelines; administration of the genetically-modified and formulated cells; appropriate reference levels to interpret results associated when using the kit; proper disposal of the related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website.

Particular embodiments of kits include one or more of: one or more sterile tubing sets; saline solution for intravenous infusion (e.g., Plasmalyte A); 25% human serum albumin (HSA); 6% hetastarch in saline (HES); buffer (e.g., PBS/EDTA); biotinylated anti-CD34 antibody (clone 12.8) (also referred to as 12.8 antibody); CD34 microbeads or other direct-conjugate antibody-magnetic bead complex; GAMMAGARD (IVIg) or other blocking agent (e.g., autologous serum); streptavidin-coated microbeads; funneled cryobag(s); needle-less spike adapter(s); syringe(s) (e.g., 60 mL, 30 mL); complete transduction media; concentrated lentivirus; medical gloves; gown and/or face mask.

The particular complete transduction media used within a kit or method is specified by the cell type and nucleic acid carrier (e.g., virus vector) to be used in transduction for the desired clinical application. The transduction media includes (1) a base medium with or without the addition of, (2) various cyto- and/or chemokines, and (3) small molecules or additional agents to promote cell survival and gene transfer. An example of a complete transduction media for hematopoietic stem cell culture and transduction could include the following: a commercially available base media such as StemSpan SFEM or ACF media (both from Stem Cell Technologies) or XVivo media types (Lonza). Cyto/chemokines added to this base media could include recombinant human granulocyte colony stimulating factor (G-CSF), stem cell factor (SCF), thrombopoietin (TPO), flightless 3 ligand (flt3 or flt3L), and interleukins such as interleukin 3 (IL3), interleukin 6 (IL6). Other cyto/chemokines can also be added at various concentrations to effect performance. Small molecules which can be added could include aryl-hydrocarbon receptor antagonists (e.g., Stem Regenin1 (e.g., Phenol, 4-[2-[[2-benzo[b]thien-3-yl-9-(1-methylethyl)-9H-purin-6-yl]amino]ethyl]); GNF351 (e.g., N-(2-(3H-Indol-3-yl)ethyl)-9-isopropyl-2-(5-methyl-3-pyridyl)-7H-purin-6-amine, N-(2-(1H-Indol-3-yl)ethyl)-9-isopropyl-2-(5-methylpyridin-3-yl)-9H-purin-6-amine); CH223191 (e.g., 1-Methyl-N-[2-methyl-4-[2-(2-methylphenyl)diazenyl]phenyl-1H-pyrazole-5-carboxamide), pyrimidoindole derivatives (e.g., UM171 (e.g., (1r,4r)-N1-(2-benzyl-7-(2-methyl-2H-tetrazol-5-yl)-9H-pyrimido[4,5-b]indol-4-yl)cyclohexane-1,4-diamine); UM729 (Methyl 4-((3-(piperidin-1-yl)propyl)amino)-9H-pyrimido[4,5-b]indole-7-carboxylate); UM118428 (e.g., Tranylcypromine HCl, (trans-2-Phenylcyclopropylamine hydrochloride)), glucocorticoid receptor antagonists (mifepristone (e.g., RU-486), RU-43044, Miconazole, 11-oxa cortisol, 11-oxa prednisolone, Dexamethasone mesylate) or combinations thereof. Additional agents which could be added include protamine sulfate, rapamycin, polybrene, fibronectin fragment, prostaglandins or nonsteroidal anti-inflammatory drugs (e.g., celecoxib, diclofenac, diflunisal, etodolac, ibuprofen, indomethacin, ketoprofen, nabumetone, naproxen, oxaprozin, piroxicam, salsalate, sulindac, tolmetin).

In particular embodiments, the particular concentrated lentivirus reagent used within a kit or method is similarly specific to the cell type and clinical application, which are the targets for gene transfer. The reagent includes engineered virus particles including a pseudotype glycoprotein enveloping a lentiviral RNA molecule engineered to encode therapeutic transgene(s) or gene editing elements specific to the clinical application of interest, suspended in a medium formulation suited to the cell type to be transduced. Examples of envelope glycoproteins include vesicular stomatitis virus glycoprotein (VSVG), cocal virus glycoprotein (cocal) or modified foamy virus glycoprotein (mFoamy). Examples of lentiviral RNA molecules include HIV-1-derived, self-inactivating lentivirus backbones encoding whole or partial human or viral promoter elements, any number of disease-specific therapeutic transgenes, guide or microRNAs, promoter elements, selection cassettes, enhancer elements, insulator elements, regulatory elements and possibly elements to enhance transcription and translation of encoded therapeutic transgenes, such as partial woodchuck hepatitis virus post-transcriptional regulatory elements, 2A viral fusion elements or internal ribosomal entry site (IRES) sequences. Examples of media formulations for concentrated lentivirus preparations include Iscove's Modified Dulbecco's Medium or Opti-Pro medium, but other formulations can be used.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments
1. A method of isolating, genetically-modifying, and formulating target cells obtained from a subject sample, the method including the steps of:
   (i) loading the subject sample into a point-of-care and/or portable device including:
      a circuit for processing the subject sample, the circuit including a sample input, a buffer input, and a treatment chamber;
      a plurality of valves for selectively closing one or more flow paths of the circuit;
      one or more target cell selector(s) for separating the target cells of the subject sample from non-target cells of the subject sample;
      at least one pump to perfuse the subject sample through at least a portion of the circuit;
      memory storing instructions executable by one or more processors to control operation of the treatment chamber, the plurality of valves, the target cell selector(s), and the pump; and
   (ii) initiating execution of the instructions by the one or more processors to cause at least one of the plurality of valves, the one or more target cell selectors, or the at least one pump to perform acts including:
      transferring the subject sample from the treatment chamber to the target cell selector(s);
      separating the target cells from the non-target cells via operation of the target cell selector(s) simultaneously or in tandem if more than one selector is used;
      transferring the target cells back into to the treatment chamber;
      introducing a genetic modifier to the target cells within the treatment chamber and/or the target cell selector(s) to generate genetically-modified target cells; and formulating the genetically-modified target cells into a formulation for administration to a subject.
2. A method of embodiment 1 wherein the initiating execution includes initiating execution of one or more of SW1, SW2, SW3, SW4, SW6, SW7, SW8 and/or SW9.
3. A method of embodiment 1 wherein the initiating execution includes initiating execution of one or more of SW1, Descriptions 1, 2, 3 or 4; SW2, Descriptions 1, 2, 3, or 4; SW3, Descriptions 1, 2, 3, or 4; SW4, Descriptions 1, 2, 3, 4, or 5; SW6, Descriptions 1, 2, 3, 4, or 5; SW7, Descriptions 1, 2, 3, 4, or 5; SW8, Descriptions 1, 2, 3, 4, or 5; and/or SW9, Descriptions 1, 2, 3, 4, or 5.
4. A method of embodiment 1 wherein the initiating execution includes initiating execution of one more of J1, J2, J3, J4, J6, J7, J8 and/or J9.
5. A method of any of embodiments 1-4 further including determining an initial volume of the subject sample.
6. A method of any of embodiments 1-5 further including determining a hematocrit level of the subject sample before the loading.
7. A method of any of embodiments 1-6 further including adding a volume of buffer to the subject sample to reduce the hematocrit level to at least 25%.
8. A method of embodiment 7 wherein the volume of buffer to add to the subject sample is calculated according to the following formula:

$$\left(\frac{\text{starting product volume (mL)} \times \text{obtained hematocrit value (\%)}}{25\% \text{ desired hematocrit value}}\right) - \text{starting product volume (mL)}$$

9. A method of embodiment 7 or 8 further including determining the hematocrit level of the subject sample following the addition of the buffer.
10. A method of any of embodiments 7-9 further including determining the volume of the diluted subject sample.
11. A method of any of embodiments 1-10 further including entering a hematocrit level of 25% into a user interface on the device.
12. A method of any of embodiments 1-11 including performing release testing to verify compliance with Current Good Manufacturing Practices.
13. A method of embodiment 12 wherein the release testing includes

| Test | Required Result |
| --- | --- |
| Gram Stain | Negative |
| 3 Day Sterility | Negative |
| 14 Day Sterility | Negative |
| Mycoplasma | Negative |
| Endotoxin | ≤0.5 EU/ml |
| Cell Viability by Trypan Blue Dye Exclusion | ≥70% |

14. A method of any of embodiments 1-13 wherein the introducing of the genetic modifier inserts or alters a gene to treat an immune-mediated condition, an inherited genetic defect, a blood disorder, a lysosomal storage disorder, a hyperproliferative disease, or an infectious disease.
15. A method of embodiment 14 wherein the immune-mediated condition is Grave's Disease, rheumatoid arthritis, pernicious anemia, Multiple Sclerosis (MS), inflammatory bowel disease, systemic lupus erythematosus (SLE), severe combined immunodeficiency disease (SCID), adenosine deaminase deficient SCID (ADA-SCID), or Wiskott-Aldrich syndrome (WAS).
16. A method of embodiment 14 wherein the inherited genetic disorder is chronic granulomatous disease (CGD), Fanconi anemia (FA), Shwachmann-Diamond-Blackfan anemia (DBA), dyskeratosis congenita (DKC), pyruvate kinase deficiency (PKD), cystic fibrosis (CF), pulmonary alveolar proteinosis (PAP), Batten's disease, adrenoleukodystrophy (ALD), metachromatic leukodystrophy (MLD), muscular dystrophy (MD), Parkinson's disease, Alzheimer's disease, or amyotrophic lateral sclerosis (ALS; Lou Gehrig's disease).
17. A method of embodiment 14 wherein the blood disorder is hemoglobinopathy like thalassemia, or sickle cell anemia.
18. A method of embodiment 14 wherein the lysosomal storage disorder is mucopolysaccharidosis (MPS) type I, MPS II, MPS III, MPS IV, MPS V, MPS VI, MPS VII, alpha-mannsidosis, beta-mannosidosis, Tay Sachs, Pompe disease, Gaucher's disease, or Fabry disease.
19. A method of embodiment 14 wherein the hyperproliferative disease is cancer.
20. A method of embodiment 14 wherein the infectious disease is caused by infection with HIV, measles, coronavirus, aminopeptidase-N, LCMV/lassa fever virus, bacteria, and/or parasites.

21. A method of any of embodiments 1-20 wherein the isolated, genetically-modified, and formulated cells are hematopoietic stem cells (HSC), hematopoietic progenitor cells (HPC), hematopoietic stem and progenitor cells (HSPC), T cells, natural killer cells, B cells, macrophages, monocytes, mesenchymal stem cells (MSC), white blood cells (WBC), mononuclear cells (MNC), endothelial cells (EC), stromal cells, and/or bone marrow fibroblasts.

22. A method of any of embodiments 1-21 wherein the isolated, genetically-modified, and formulated cells are CD34+ HSPC.

23. A method of any of embodiments 14-22 wherein the gene is one or more of ABCD1, ABCA3, ABLI, ADA, AKT1, APC, APP, ARSA, ARSB, BCL11A, BLC1, BLC6, BRCA1, BRCA2, BRIP1, C9ORF72, C46 or other C peptide, CAR, CAS9, C-CAM, CBFAI, CBL, CCR5, CD4, CD19, CD40, CDA, CFTR, CLN3, C-MYC, CRE, CSCR4, CSFIR, CTLA, CTS-I, CYB5R3, DCC, DHFR, DKC1, DLL1, DMD, EGFR, ERBA, ERBB, EBRB2, ETSI, ETS2, ETV6, F8, F9, FANCA, FANCB, FANCC, FANCD2, FANCE, FANCF, FANCG, FANCI, FANCL, FANCM, FasL, FCC, FGR, FOX, FUS, FUSI, FYN, GALNS, GATA1, GLB1, GNS, GUSB, HBB, HBD, HBE1, HBG1, HBG2, HCR, HGSNAT, HOXB4, HRAS, HYAL1, ICAM-1, iCaspase, IDUA, IDS, JUN, KLF4, KRAS, LCK, LRRK2, LYN, MCC, MDM2, MGMT, MLL, MMACI, MYB, MEN-I, MEN-II, MYC, NAGLU, NANOG, NF-1, NF-2, NKX2.1, NOTCH, OCT4, p16, p2I, p27, p53, p57, p73, PALB2, PARK2, PARK7, phox, PINK1, PK, PSEN1, PSEN2, PTPN22, RAD51C, ras, RPL3 through RPL40, RPLP0, RPLP1, RPLP2, RPS2 through RPS30, RPSA, SFTPB, SFTPC, SGSH, SLX4, SNCA, SOD1, SOX2, TERC, TERT, TDP43, TINF2, TK, ubiquilin 2, VHL, WAS and WT-I.

24. A method of any of embodiments 1-23 further including administering a therapeutically effective amount of the isolated, genetically-modified, and formulated cells to a subject in need thereof.

25. A method of embodiment 24 wherein the therapeutically effective amount of the isolated, genetically-modified, and formulated cells is ≥2.5E+05/kg subject body weight.

26. A method of embodiment 24 wherein the therapeutically effective amount of the isolated, genetically-modified, and formulated cells is $2 \times 10^6$ cells/kg subject body weight.

27. A method of embodiment 14 wherein the genetic modifier includes a non-integrating vector.

28. A method of embodiment 14 or 27 wherein the genetic modifier includes a viral vector.

29. A method of embodiment 14, 27, or 28 wherein the genetic modifier includes a lentiviral vector.

30. A method of embodiment 29 wherein the lentiviral vector includes a pseudotype envelope glycoprotein and a lentiviral RNA molecule.

31. A method of embodiment 30 wherein the pseudotype envelope glycoprotein includes vesicular stomatitis virus glycoprotein (VSVG), cocal virus glycoprotein (cocal), the feline endogenous virus glycoprotein (RD114), or modified foamy virus glycoprotein (mFoamy).

32. A method of embodiment 30 or 31 wherein the lentiviral RNA molecule includes a HIV-1-derived, self-inactivating lentivirus backbone.

33. A method of embodiment 30 or 31 wherein the lentiviral RNA molecule includes a HIV-1-derived, self-inactivating lentivirus backbone which is integration deficient.

34. A method of embodiment 14, 27, or 28 wherein the genetic modifier includes a gammaretroviral vector.

35. A method of embodiment 34 wherein the gammaretroviral vector includes a pseudotype envelope glycoprotein and a gammaretroviral RNA molecule.

36. A method of embodiment 35 wherein the pseudotype envelope glycoprotein includes gibbon ape leukemia virus glycoprotein (GALV), or the feline endogenous virus envelope (RD114).

37. A method of embodiment 35 or 36 wherein the gammaretroviral RNA molecule includes a self-inactivating gammaretrovirus backbone.

38. A method of embodiment 35 or 36 wherein the gammaretroviral RNA molecule includes a self-inactivating gammaretrovirus backbone which is integration deficient.

39. A method of embodiment 14, 27, or 28 wherein the genetic modifier includes a foamy viral vector.

40. A method of embodiment 39 wherein the foamy viral vector includes a pseudotype envelope glycoprotein and a foamy viral RNA molecule.

41. A method of embodiment 40 wherein the pseudotype envelope glycoprotein includes foamy viral envelope protein (Foamy), or modified foamy viral envelope protein (mFoamy).

42. A method of embodiment 40 or 41 wherein the foamy viral RNA molecule includes a self-inactivating foamy virus backbone.

43. A method of embodiment 40 or 41 wherein the foamy viral RNA molecule includes a self-inactivating foamy virus backbone which is integration deficient.

44. A method of embodiment 14, 27, or 28 wherein the genetic modifier includes an alpharetroviral vector.

45. A method of embodiment 44 wherein the alpharetroviral vector includes a pseudotype envelope glycoprotein and an alpharetroviral RNA molecule.

46. A method of embodiment 45 wherein the pseudotype envelope glycoprotein includes the vesicular stomatitis virus glycoprotein (VSVG), cocal virus glycoprotein (cocal), the feline endogenous virus glycoprotein (RD114), or modified foamy virus glycoprotein (mFoamy).

47. A method of embodiment 45 or 46 wherein the alpharetroviral RNA molecule includes a self-inactivating alpharetrovirus backbone.

48. A method of any of embodiments 14-47 wherein the genetic modifier includes a lentiviral, gammaretroviral, foamy viral or alpharetorviral vector further including one or more promoter elements, selection cassettes, enhancer elements, insulator elements, regulatory elements, and transcription/translation enhancer elements.

49. A method of embodiment 48 wherein the transcription/translation enhancer elements include partial woodchuck hepatitis virus post-transcriptional regulatory elements, 2A viral fusion elements or internal ribosomal entry site (IRES) sequences.

50. A method of embodiment 14 wherein the genetic modifier includes naked DNA, naked mRNA, an adenoviral vector, or an adeno-associated vector, guide RNA, zinc fingers, meganucleases, TALENs, meganuclease-TALEN fusions (megaTALs), and/or genes flanked by regions of homology.

51. A method of any of embodiments 1-50 including sterile welding one or more funneled cryobags to a tubing set attached to the device.

52. A method of any of embodiments 1-51 including selecting a bag volume appropriate for an anticipated volume of sedimentation.

53. A method of any of embodiments 1-52 including entering a number of stages required to load the subject sample into the tubing set for sedimentation wherein the required number of stages is obtained by dividing the diluted sample volume in mL by 300 mL per stage and rounding up to the next whole number.
54. A method of any of embodiments 1-53 including indicating to the device sedimentation is complete and RBC removal may begin.
55. A method of any of embodiments 1-54 including entering an initial volume (mL) to remove from a RBC sediment layer.
56. A method of any of embodiments 1-55 including loading beads or antibodies that selectively bind CD3, CD4, CD8, CD13, CD14, CD15, CD16, CD19, CD20, CD34, CD45, CD45RA, CD45RO, CD49f, CD50, CD56, CD71, CD90, or CD133 into the device
57. A method of any of embodiments 1-56 including loading microbeads and IVIg into the device.
58. A method of any of embodiments 1-57 including sealing a tubing set above a luer connection of a Target Cell Bag containing target cells.
59. A method of any of embodiments 1-58 including loading transduction media into the device.
60. A method of embodiment 59 wherein the transduction media includes a base medium, cyto- and/or chemokines, and agents to promote cell survival and gene transfer.
61. A method of embodiment 60 wherein the cyto/chemokines include recombinant human granulocyte colony stimulating factor (G-CSF), stem cell factor (SCF), thrombopoietin (TPO), flightless 3 ligand (flt3 or flt3L), and interleukins.
62. A method of embodiment 61 wherein the interleukins include interleukin 3 (IL-3) and/or interleukin 6 (IL-6).
63. A method of any of embodiments 60-62 wherein the agents include aryl-hydrocarbon receptor antagonists, pyrimidoindole derivatives, glucocorticoid receptor antagonists, protamine sulfate, rapamycin, polybrene, fibronectin fragment, prostaglandins, antioxidants and/or nonsteroidal anti-inflammatory drugs.
64. A method any of embodiments 60-63 wherein the aryl-hydrocarbon receptor antagonists include StemRegenin1; GNF351; and/or CH223191.
65. A method of any of embodiments 60-64 wherein the pyrimidoindole derivatives include UM171, and/or UM118428.
66. A method of any of embodiments 60-65 wherein the glucocorticoid receptor antagonists include mifepristone, RU-43044, Miconazole, 11-oxa cortisol, 11-oxa prednisolone, and/or dexamethasone mesylate.
67. A method of any of embodiments 60-66 wherein prostaglandins include prostaglandin E2.
68. A method of any of embodiments 60-67 wherein the nonsteroidal anti-inflammatory drugs include celecoxib, diclofenac, diflunisal, etodolac, ibuprofen, indomethacin, ketoprofen, nabumetone, naproxen, oxaprozin, piroxicam, salsalate, sulindac, and/or tolmetin.
69. A method of any of embodiments 1-68 including drawing a volume of Concentrated Lentivirus, gammaretrovirus, foamy virus or alpharetrovirus into an appropriately sized syringe and connecting the syringe to a luer fitting.
70. A method of any of embodiments 1-69 including drawing a second volume of Concentrated Lentivirus, gammaretrovirus, foamy virus or alpharetrovirus into an appropriately sized syringe and connecting the syringe to a luer fitting.
71. A method any of embodiments 1-70 including spiking a needle-free spike adapter into a bag of formulation buffer.
72. A method of any of embodiments 1-71 including replacing a Target Cell Bag with a bag of formulation buffer.
73. A method of any of embodiments 1-72 including manually opening a valve pathway from a cryobag to a waste bag to allow formulation buffer to drain through a tubing set.
74. A kit for isolating, genetically-modifying, and formulating target cells obtained from a subject, the kit including a genetic modifier and instructions regarding sample processing; software program use; and/or user interface guidelines for use with a point-of-care and/or portable device.
75. A kit of embodiment 74 including instructions for use of one or more of SW1, Descriptions 1, 2, 3 or 4; SW2, Descriptions 1, 2, 3, or 4; SW3, Descriptions 1, 2, 3, or 4; SW4, Descriptions 1, 2, 3, 4, or 5; SW6, Descriptions 1, 2, 3, 4, or 5; SW7, Descriptions 1, 2, 3, 4, or 5; SW8, Descriptions 1, 2, 3, 4, or 5; and/or SW9, Descriptions 1, 2, 3, 4, or 5.
76. A kit of embodiment 74 including instructions for use of one or more of J1, J2, J3, J4, J6, J7, J8 or J9.
77. A kit of any of embodiments 74-76 wherein the instructions direct determining the starting volume of the subject sample.
78. A kit of any of embodiments 74-77 wherein the instructions direct determining a hematocrit level of the subject sample before the introducing.
79. A kit of any of embodiments 74-78 wherein the instructions direct adding a volume of buffer to the subject sample to reduce the hematocrit level to 25%.
80. A kit of any of embodiment 79 wherein the instructions direct that the volume of buffer to add to the subject sample is calculated according to the following formula:

$$\left(\frac{\text{starting product volume (mL)} \times \text{obtained hematocrit value (\%)}}{25\% \text{ desired hematocrit value}}\right) - \text{starting product volume (mL)}$$

81. A kit of any of embodiments 74-80 wherein the instructions direct determining the hematocrit level of the subject sample following the addition of the buffer.
82. A kit of any of embodiments 74-81 wherein the instructions direct determining the volume of a diluted sample.
83. A kit of any of embodiments 74-82 wherein the instructions direct entering a hematocrit level of 25% into a user interface on the device.
84. A kit of any of embodiments 74-83 wherein the instructions direct sterile welding one or more funneled cryobags to a tubing set attached to the device.
85. A kit of any of embodiments 74-84 wherein the instructions direct selecting a bag volume appropriate for an anticipated volume of sedimentation.
86. A kit of any of embodiments 74-85 wherein the instructions direct entering a number of stages required to load the subject sample into the tubing set for sedimentation wherein the required number of stages is obtained by dividing the diluted sample volume in mL by 300 mL per stage and rounding up to the next whole number.
87. A kit of any of embodiments 74-87 wherein the instructions direct indicating to the device sedimentation is complete and RBC removal may begin.
88. A kit of any of embodiments 74-87 wherein the instructions direct entering an initial volume (mL) to remove from a RBC sediment layer.
89. A kit of any of embodiments 74-88 wherein the instructions direct isolation, genetically-modification, and formulation of cells selected hematopoietic stem cells (HSC), hematopoietic progenitor cells (HPC), hematopoietic stem and progenitor cells (HSPC), T cells, natural killer cells, B cells, macrophages, monocytes, mesenchymal stem cells (MSC), white blood cells (WBC), mononuclear cells (MNC), endothelial cells (EC), stromal cells, and/or bone marrow fibroblasts.
90. A kit of any of embodiments 74-89 wherein the instructions direct isolation, genetically-modification, and formulation of CD34+ HSPC.
91. A kit of any of embodiments 74-90 wherein the instructions direct loading beads or antibodies that selectively bind CD3, CD4, CD8, CD13, CD14, CD15, CD16, CD19, CD20, CD34, CD45, CD45RA, CD45RO, CD49f, CD50, CD56, CD71, CD90, or CD133 into the device.
92. A kit of any of embodiments 74-91 wherein the instructions direct loading microbeads and IVIg into the device.
93. A kit of any of embodiments 74-92 wherein the instructions direct sealing a tubing set above a luer connection of a Target Cell Bag containing target cells.
94. A kit of any of embodiments 74-93 wherein the instructions direct loading transduction media into the device.
95. A kit of any of embodiments 74-94 wherein the instructions direct drawing a volume of Concentrated Lentivirus, gammaretrovirus, foamy virus or alpharetrovirus into an appropriately sized syringe and connecting the syringe to a luer fitting.
96. A kit of any of embodiments 74-95 wherein the instructions direct drawing a second volume of Concentrated Lentivirus, gammaretrovirus, foamy virus or alpharetrovirus into an appropriately sized syringe and connecting the syringe to a luer fitting.
97. A kit of any of embodiments 74-96 wherein the instructions direct spiking a needle-free spike adapter into a bag of formulation buffer.
98. A kit of any of embodiments 74-97 wherein the instructions direct replacing a Target Cell Bag with a bag of formulation buffer.
99. A kit of any of embodiments 74-98 wherein the instructions direct manually opening a valve pathway from a cryobag to a waste bag to allow formulation buffer to drain through a tubing set.
100. A kit of any of embodiments 74-99 wherein the instructions direct performing release testing to verify compliance with Current Good Manufacturing Practices.
101. A kit of embodiment 100 wherein the release testing includes

| Test | Required Result |
| --- | --- |
| Gram Stain | Negative |
| 3 Day Sterility | Negative |
| 14 Day Sterility | Negative |
| Mycoplasma | Negative |
| Endotoxin | ≤0.5 EU/ml |
| Cell Viability by Trypan Blue Dye Exclusion | ≥70% |

102. A kit of any of embodiments 74-101 wherein the instructions direct administering a therapeutically effective amount of the isolated, genetically-modified, and formulated cells to a subject in need thereof.
103. A kit of embodiment 102 wherein the therapeutically effective amount of the isolated, genetically-modified, and formulated cells is ≥2.5+F05/kg subject body weight.
104. A kit of embodiment 102 wherein the therapeutically effective amount of the isolated, genetically-modified, and formulated cells is $2 \times 10^6$ cells/kg subject body weight.

105. A kit of any of embodiments 74-104 including a genetic modifier to introduce or alter a gene to treat an immune-mediated condition, an inherited genetic defect, a blood disorder, a lysosomal storage disorder, a hyperproliferative disease, or an infectious disease.
106. A kit of embodiment 105 wherein the immune-mediated condition is Grave's Disease, rheumatoid arthritis, pernicious anemia, Multiple Sclerosis (MS), inflammatory bowel disease, systemic lupus erythematosus (SLE), severe combined immunodeficiency disease (SCID), adenosine deaminase deficient SCID (ADA-SCID), or Wiskott-Aldrich syndrome (WAS).
107. A kit of embodiment 105 wherein the inherited genetic disorder is chronic granulomatous disease (CGD), Fanconi anemia (FA), Shwachmann-Diamond-Blackfan anemia (DBA), dyskeratosis congenita (DKC), pyruvate kinase deficiency (PKD), cystic fibrosis (CF), pulmonary alveolar proteinosis (PAP), Batten's disease, adrenoleukodystrophy (ALD), metachromatic leukodystrophy (MLD), muscular dystrophy (MD), Parkinson's disease, Alzheimer's disease, or amyotrophic lateral sclerosis (ALS; Lou Gehrig's disease).
108. A kit of embodiment 105 wherein the blood disorder is hemoglobinopathy like thalassemia, or sickle cell anemia.
109. A kit of embodiment 105 wherein the lysosomal storage disorder is mucopolysaccharidosis (MPS) type I, MPS II, MPS III, MPS IV, MPS V, MPS VI, MPS VII, alpha-mannsidosis, beta-mannosidosis, Tay Sachs, Pompe disease, Gaucher's disease, or Fabry disease.
110. A kit of embodiment 105 wherein the hyperproliferative disease is cancer.
111. A kit of embodiment 105 wherein the infectious disease is caused by infection with HIV, measles, coronavirus, aminopeptidase-N, LCMV/lassa fever virus, bacteria, and/or parasites.
112. A kit of e any of embodiments 105-111 wherein the gene is one or more of ABCD1, ABCA3, ABLI, ADA, AKT1, APC, APP, ARSA, ARSB, BCL11A, BLC1, BLC6, BRCA1, BRCA2, BRIP1, C9ORF72, C46 or other C peptide, CAR, CAS9, C-CAM, CBFAI, CBL, CCR5, CD4, CD19, CD40, CDA, CFTR, CLN3, C-MYC, CRE, CSCR4, CSFIR, CTLA, CTS-I, CYB5R3, DCC, DHFR, DKC1, DLL1, DMD, EGFR, ERBA, ERBB, EBRB2, ETSI, ETS2, ETV6, F8, F9, FANCA, FANCB, FANCC, FANCD2, FANCE, FANCF, FANCG, FANCI, FANCL, FANCM, FasL, FCC, FGR, FOX, FUS, FUSI, FYN, GALNS, GATA1, GLB1, GNS, GUSB, HBB, HBD, HBE1, HBG1, HBG2, HCR, HGSNAT, HOXB4, HRAS, HYAL1, ICAM-1, iCaspase, IDUA, IDS, JUN, KLF4, KRAS, LCK, LRRK2, LYN, MCC, MDM2, MGMT, MLL, MMACI, MYB, MEN-I, MEN-II, MYC, NAGLU, NANOG, NF-1, NF-2, NKX2.1, NOTCH, OCT4, p16, p2I, p27, p53, p57, p73, PALB2, PARK2, PARK7, phox, PINK1, PK, PSEN1, PSEN2, PTPN22, RAD51C, ras, RPL3 through RPL40, RPLP0, RPLP1, RPLP2, RPS2 through RPS30, RPSA, SFTPB, SFTPC, SGSH, SLX4, SNCA, SOD1, SOX2, TERC, TERT, TDP43, TINF2, TK, ubiquilin 2, VHL, WAS and WT-I.
113. A kit of any of embodiments 105-112 wherein the genetic modifier includes a viral vector.
114. A kit of any of embodiments 105-113 wherein the genetic modifier includes a non-integrating vector.
115. A kit of any of embodiments 105-114 wherein the genetic modifier includes a lentiviral vector.
116. A kit of embodiment 115 wherein the lentiviral vector includes a pseudotype envelope glycoprotein and a lentiviral RNA molecule.

117. A kit of embodiment 116 wherein the pseudotype envelope glycoprotein includes vesicular stomatitis virus glycoprotein (VSVG), cocal virus glycoprotein (cocal), the feline endogenous virus glycoprotein (RD114), or modified foamy virus glycoprotein (mFoamy).

118. A kit of embodiment 116 or 117 wherein the lentiviral RNA molecule includes a HIV-1-derived, self-inactivating lentivirus backbone.

119. A kit of embodiment 116 or 117 wherein the lentiviral RNA molecule includes a HIV-1-derived, self-inactivating lentivirus backbone which is integration deficient.

120. A kit of any of embodiments 105-114 wherein the genetic modifier includes a gammaretroviral vector.

121. A kit of embodiment 120 wherein the gammaretroviral vector includes a pseudotype envelope glycoprotein and a gammaretroviral RNA molecule.

122. A kit of embodiment 121 wherein the pseudotype envelope glycoprotein includes gibbon ape leukemia virus glycoprotein (GALV), or the feline endogenous virus envelope (RD114).

123. A kit of embodiment 121 or 122 wherein the gammaretroviral RNA molecule includes a self-inactivating gammaretrovirus backbone.

124. A kit of embodiment 121 or 122 wherein the gammaretroviral RNA molecule includes a self-inactivating gammaretrovirus backbone which is integration deficient.

125. A kit of any of embodiments 105-114 wherein the genetic modifier includes a foamy viral vector.

126. A kit of embodiment 125 wherein the foamy viral vector includes a pseudotype envelope glycoprotein and a foamy viral RNA molecule.

127. A kit of embodiment 126 wherein the pseudotype envelope glycoprotein includes foamy viral envelope protein (Foamy), or modified foamy viral envelope protein (mFoamy).

128. A kit of embodiment 126 or 127 wherein the foamy viral RNA molecule includes a self-inactivating foamy virus backbone.

129. A kit of embodiment 126 or 127 wherein the foamy viral RNA molecule includes a self-inactivating foamy virus backbone which is integration deficient.

130. A kit of any of embodiments 105-114 wherein the genetic modifier includes an alpharetroviral vector.

131. A kit of embodiment 130 wherein the alpharetroviral vector includes a pseudotype envelope glycoprotein and an alpharetroviral RNA molecule.

132. A kit of embodiment 131 wherein the pseudotype envelope glycoprotein includes the vesicular stomatitis virus glycoprotein (VSVG), cocal virus glycoprotein (cocal), the feline endogenous virus glycoprotein (RD114), or modified foamy virus glycoprotein (mFoamy).

133. A kit of embodiment 131 or 132 wherein the alpharetroviral RNA molecule includes a self-inactivating alpharetrovirus backbone.

134. A kit of any of embodiments 105-133 wherein the genetic modifier includes a lentiviral, gammaretroviral, foamy viral or alpharetorviral vector further including one or more promoter elements, selection cassettes, enhancer elements, insulator elements, regulatory elements, and transcription/translation enhancer elements.

135. A kit of embodiment 134 wherein the transcription/translation enhancer elements include partial woodchuck hepatitis virus post-transcriptional regulatory elements, 2A viral fusion elements or internal ribosomal entry site (IRES) sequences.

136. A kit of embodiment 105 wherein the genetic modifier includes naked DNA, naked mRNA, an adenoviral vector, or an adeno-associated vector, guide RNA, zinc fingers, meganucleases, TALENs, meganuclease-TALEN fusions (megaTALs), and/or genes flanked by regions of homology.

137. A kit of any of embodiments 74-136 further including transduction media.

138. A kit of embodiment 137 wherein the transduction media includes a base medium, cyto- and/or chemokines, and agents to promote cell survival and gene transfer.

139. A kit of embodiment 138 wherein the cyto/chemokines include recombinant human granulocyte colony stimulating factor (G-CSF), stem cell factor (SCF), thrombopoietin (TPO), flightless 3 ligand (flt3 or flt3L), and interleukins.

140. A kit of embodiment 139 wherein the interleukins include interleukin 3 (IL-3) and/or interleukin 6 (IL-6).

141. A kit of any of embodiments 138-140 wherein the agents include aryl-hydrocarbon receptor antagonists, pyrimidoindole derivatives, glucocorticoid receptor antagonists, protamine sulfate, rapamycin, polybrene, fibronectin fragment, prostaglandins, antioxidants or nonsteroidal anti-inflammatory drugs.

142. A kit of any of embodiments 138-141 wherein the aryl-hydrocarbon receptor antagonists include StemRegenin1; GNF351; and/or CH223191.

143. A kit of any of embodiments 138-142 wherein the pyrimidoindole derivatives include UM171, and/or UM118428.

144. A kit of any of embodiments 138-143 wherein the glucocorticoid receptor antagonists include mifepristone, RU-43044, Miconazole, 11-oxa cortisol, 11-oxa prednisolone, and/or dexamethasone mesylate.

145. A kit of any of embodiments 138-144 wherein prostaglandins include prostaglandin E2.

146. A kit of any of embodiments 138-145 wherein the nonsteroidal anti-inflammatory drugs include celecoxib, diclofenac, diflunisal, etodolac, ibuprofen, indomethacin, ketoprofen, nabumetone, naproxen, oxaprozin, piroxicam, salsalate, sulindac, and/or tolmetin.

147. A kit of any of embodiments 74-146 further including a sterile tubing set.

148. A kit of any of embodiments 74-147 further including a pharmaceutically acceptable.

149. A kit of embodiment 148 wherein the pharmaceutically acceptable includes a saline solution for intravenous infusion.

150. A kit of any of embodiments 74-149 including human serum albumin.

151. A kit of any of embodiments 74-150 further including hetastarch in saline.

152. A kit of any of embodiments 74-151 further including a buffer.

153. A kit of embodiment 152 wherein the buffer is PBS/EDTA.

154. A kit of any of embodiments 74-153 further including beads or antibodies that selectively bind CD3, CD4, CD8, CD13, CD14, CD15, CD16, CD19, CD20, CD34, CD45, CD45RA, CD45RO, CD49f, CD50, CD56, CD71, CD90, or CD133.

155. A kit of any of embodiments 74-154 further including a biotinylated anti-CD34 antibody.

156. A kit of embodiment 155 wherein the biotinylated anti-CD34 antibody is clone 12.8.

157. A kit of any of embodiments 74-156 further including CD34 microbeads.

158. A kit of any of embodiments 74-157 further including a blocking agent.

159. A kit of embodiment 158 wherein the blocking agent is autologous serum.
160. A kit of any of embodiments 74-159 further including streptavidin-coated microbeads.
161. A kit of any of embodiments 74-160 further including funneled cryobag(s).
162. A kit of any of embodiments 74-161 further including needle-less spike adapter(s).
163. A kit of any of embodiments 74-162 further including syringe(s).
164. A kit of embodiment 163 wherein the syringes are 60 mL and/or 30 mL syringes.
165. A flow-through electroporation apparatus including:
    a housing including a sample inlet and a sample outlet, the housing being impermeable to a sample;
    a first electrode and a second electrode disposed within the housing, wherein at least a portion of the first electrode is positioned at a fixed distance apart from at least a portion of the second electrode to define at least one electrode gap,
    wherein at least a portion of the electrode gap forms a subject sample pathway to enable the subject sample to flow from the subject sample inlet to the subject sample outlet.
166. An electroporation apparatus of embodiment 165 wherein at least one of the first electrode or the second electrode are magnetically susceptible.
167. An electroporation apparatus of embodiment 165 or 166 further including a first terminal corresponding to the first electrode and a second terminal corresponding to the second electrode, wherein each of the first electrode and the second electrode protrude from the housing.
168. An electroporation apparatus of any of embodiments 165-167 wherein the at least one electrode gap is maintained by one or more insulators disposed between the first electrode and the second electrode.
169. An electroporation apparatus of any of embodiments 165-168 wherein the first electrode includes a first plurality of protrusions and the second electrode includes a second plurality of protrusions, and wherein at least some of the first plurality of protrusions are disposed between at least some of the second plurality of protrusions such that the at least one electrode gap includes at least two electrode gaps.
170. An electroporation device of any of embodiments 165-169 wherein at least a portion of the subject sample pathway is formed by a first plurality of pores, corresponding to the first plurality of protrusions, and a second plurality of pores, corresponding to the second plurality of protrusions.
171. An electroporation device of any of embodiments 165-170 further including a magnetically susceptible material (MSM) disposed between at least a portion of the first electrode and at least a portion of the second electrode.
172. An electroporation device of embodiment 171 wherein the MSM includes at wires, metal coated fibers, steel wool, and/or metallic spheres.
173. An electroporation device of embodiment 171 or 172 wherein the MSM is coated with an electrical insulator, and wherein the MSM maintains the fixed distance.
174. An electroporation device of any of embodiments 171-173 wherein the first electrode and/or the second electrode is aluminum and wherein the MSM is ferromagnetic.
175. An electroporation device of any of embodiments 165-174 wherein the fixed distance is greater than or equal to 0.1 cm and less than or equal to 0.4 cm.
176. A device to isolate, genetically-modify, and formulate a target cell from a sample having target cells and non-target cells including:
    a circuit for processing the subject sample, the circuit including a sample input, a buffer input, and a treatment chamber;
    a plurality of valves for selectively closing one or more flow paths of the circuit;
    one or more the target cell selector(s) for separating target cells of the subject sample from non-target cells of the subject sample;
    a pump to perfuse the subject sample through at least a portion of the circuit;
    one or more processors to control operation of the treatment chamber, the plurality of valves, the target cell selector(s), and the pump; and
    memory storing instructions that, when executed by the one or more processors, cause one or more hardware components of the point-of-care and/or portable device to perform acts including:
        perfusing the subject sample from the treatment chamber to the target cell selector(s);
        separating the target cells from the non-target cells via operation of the target cell selector(s) either simultaneously or in tandem if multiple selectors are used in concert;
        transferring the target cells back into to the treatment chamber;
        introducing a genetic modifier to the target cells within the treatment chamber and/or the target cell selector(s) to generate genetically-modify target cells; and
        formulating the genetically-modified target cells into a formulation for administration to a subject
    wherein the device is point-of-care and/or portable.
177. A device of embodiment 176 wherein the treatment chamber forms the interior chamber of a centrifuge.
178. A device of embodiment 176 or 177 wherein the target cell selector(s) include a magnetic cell selector and/or a flow cytometer and/or a flow-based cell sorter.
179. A device of any of embodiments 176-178 wherein the target cell selector(s) include a flow-based cell sorter that utilizes forward, back, and side light scatter properties, fluorochrome absorbance and emission spectra to separate target cells from non-target cells.
180. A device of any of embodiments 176-179 wherein the target cell selector(s) include a flow-through electroporation apparatus including:
    a housing having a sample inlet and a sample outlet, the housing being impermeable to a sample;
    a first electrode and a second electrode disposed within the housing, wherein at least a portion of the first electrode is positioned at a fixed distance apart from at least a portion of the second electrode to define at least one electrode gap,
    wherein at least a portion of the electrode gap forms a sample pathway to enable the subject sample to flow from the subject sample inlet to the subject sample outlet.
181. A device of any of embodiments 176-180 further including a gas regulator coupled to the treatment chamber.
182. A device of embodiment 181 wherein the gas regulator is configured to selectively control a first partial pressure corresponding to nitrogen gas (N2), a second partial pressure corresponding to carbon dioxide gas (CO2), and a third partial pressure corresponding to oxygen gas (O2).

183. A device of any of embodiments 176-182 wherein the memory storing instructions that, when executed by the one or more processors, cause one or more hardware components of the point-of-care and/or portable device to create and maintain an incubation environment within the treatment chamber.

184. A device of embodiment 183 wherein the created and maintained incubation environment includes a specified temperature range or gas mix.

185. A device of any of embodiments 176-184 wherein the memory storing instructions further cause the one or more hardware components to perform an act including: prior to the perfusing, combining the subject sample with a target cell primary labeling agent to create a labeling suspension within the treatment chamber.

186. A device of any of embodiments 176-185 wherein the memory storing instructions further cause the one or more hardware components to perform an act including: maintaining an incubation environment within the treatment chamber to facilitate binding of the target cell primary labeling agent with the target cells.

187. A device of any of embodiments 176-186 wherein the memory storing instructions further cause the one or more hardware components to perform an act including: agitating, within the treatment chamber, the labeling suspension to induce the binding of the target cell primary labeling agent with the target cells.

188. A device of embodiment 187 wherein the agitating includes at least partially rotating the treatment chamber by operation of a centrifuge motor.

189. A device of embodiment 187 or 188 wherein the agitating includes ultrasonic agitation of the labeling suspension.

190. A device of any of embodiments 187-189 wherein the memory storing instructions further cause the one or more hardware components to perform an act including: subsequent to the agitating, removing a non-bound excess amount of the target cell primary labeling agent.

191. A device of any of embodiments 185-190 wherein the primary labeling agent includes immunomagnetic beads or antibodies, and wherein the labeling suspension further includes a first buffer solution.

192. A device of any of embodiments 176-191 wherein the memory storing instructions further cause the one or more hardware components to perform acts including:
[a] introducing transduction media to the target cells within the treatment chamber;
[b] pelleting the target cells within the treatment chamber through centrifugation;
[c] removing a supernatant volume formed during the pelleting; and
performing at least one repeat cycle of steps [a] through [c] prior to the introducing the genetic modifier to the treatment chamber.

193. A device of any of embodiments 176-192 wherein the memory storing instructions further cause the one or more hardware components to perform an act including:
determining a hematocrit level of the subject sample; and
based on a determination that the hematocrit level is above a predetermined hematocrit level threshold, performing a red blood cell (RBC) depletion protocol on the blood sample.

194. A device of embodiment 193 wherein the determining the hematocrit level of the subject sample includes centrifuging the subject sample within the treatment chamber to separate the subject sample into a red blood cell layer.

195. A device of embodiment 193 or 194 wherein the determining the hematocrit level of the subject sample includes measuring one or more optical properties of the subject sample through one or both of forward light scattering or backward light scattering.

196. A device of any of embodiments 193-195 wherein the RBC depletion protocol includes:
combining the subject sample and a first buffer, wherein the subject sample includes bone marrow and/or peripheral blood;
initiating, by centrifugation within the treatment chamber, rouleau of a plurality of RBCs of the subject sample;
perfusing the subject sample from the treatment chamber to a sedimentation receptacle;
performing stepwise removal of a RBC-rich fraction of the subject sample from the sedimentation receptacle; and
removing the first buffer from the subject sample through supernatant washing in a second buffer.

197. A device of any of embodiments 193-196 wherein the predetermined hematocrit level threshold is 25%, the first buffer is a hetastarch-based media, and the second buffer includes phosphate buffered saline (PBS) and ethylenediaminetetraacetic acid (EDTA).

198. A device of embodiment 196 or 197 wherein the removing the first buffer from the subject sample is initiated in response to receiving a user-input to confirm completion of the performing stepwise removal of a RBC-rich fraction of the subject sample from the sedimentation receptacle.

199. A device of any of embodiments 196-198 wherein the RBC depletion protocol further includes:
subsequent to the removing the first buffer from the subject sample, concentrating the subject sample through centrifugation and aspiration of the subject sample within the treatment chamber.

200. A device of any of embodiments 176-199 wherein the isolated, genetically-modified, and formulated cells meet Current Good Manufacturing Practices.

201. A device of embodiment 200 wherein conformance with Current Good Manufacturing Practices is verified with release testing including

| Test | Required Result |
|---|---|
| Gram Stain | Negative |
| 3 Day Sterility | Negative |
| 14 Day Sterility | Negative |
| Mycoplasma | Negative |
| Endotoxin | ≤0.5 EU/ml |
| Cell Viability by Trypan Blue Dye Exclusion | ≥70% |

EXAMPLES

The tremendous potential for hematopoietic stem and progenitor (CD34+) cell gene therapy has been demonstrated in the last decade for many different diseases [reviewed in (Ghosh, et al., Gene therapy for monogenic disorders of the bone marrow. Br J Haematol, (2015))]. As the field closes in on disorders of large global burden, such as HIV and hemoglobinopathies which are demographically skewed towards resource-limited countries, the lack of a portable technology for efficient gene transfer limits adoption of this powerful therapeutic approach. Ex vivo lentivirus (LV)-mediated gene transfer into CD34+ cells is the most clinically applied method for CD34+ stem cell gene therapy demonstrating efficacy to date. This approach allows for subsequent production of all blood cell types harboring the therapeutic gene for the lifetime of the patient. The isolation and genetic modification of CD34+ cells ex vivo provides two major benefits: elimination of gene transfer to non-target cells and reduced LV particle requirement, which in turn reduces costs associated with vector production.

This process involves some generalized steps including (1) immunomagnetic bead-based isolation of target CD34+ cells, (2) supportive culture conditions for resulting CD34+ cells with (3) exposure to defined concentrations of LV vector encoding the therapeutic gene of interest, and finally, (4) purification of CD34+ cells from residual virus containing media for preparation and testing of the final cellular product prior to infusion. However, the source of CD34+ cells (i.e. cord blood [CB], bone marrow [BM] or growth factor mobilized leukapheresis [APH]), and the therapeutic gene(s) encoded in the vector for gene transfer vary depending on the target patient population. To manufacture these products within current regulatory guidelines requires complex centralized facilities adhering to current Good Manufacturing Practices (cGMP). Thus, a point-of-care and/or portable strategy to achieve gene transfer into hematopoietic stem cells would represent a major advance in reducing global disease burdens such as HIV.

The simplest strategy proposed to distribute gene therapy on a global scale involves direct in vivo gene modification. Efforts to achieve CD34+ cell gene transfer in vivo in small and large animal models are underway (Burtner, et al., *Blood* 123, 3578-3584 (2014); Kay, et al., *Science* 262, 117-119 (1993); Ponder, et al., *Proc Natl Acad Sci USA* 99, 13102-13107 (2002); Ting-De Ravin, et al., *Blood* 107, 3091-3097 (2006); Frecha, et al., *Blood* 119, 1139-1150 (2012)), but it will likely be some time before this approach meets current safety and efficacy standards to permit clinical testing in patients. Major hurdles in this field include stringent evaluation of gene transfer to non-target cells balanced with achieving sufficient therapeutic CD34+ gene transfer levels. Alternatively, the development of a transferable and modifiable platform for rapid ex vivo gene transfer into CD34+ cells would have immediate applicability, but until recently this was not technologically feasible.

Efficient ex vivo lentivirus gene transfer into CD34+ cells can be achieved in less than 36 hours as part of a program to develop gene therapy for Fanconi anemia (FA) (Becker, et al., *Gene Ther* 17, 1244-1252 (2010)). FA CD34+ cells are rare, sensitive to prolonged manipulation, and respond poorly to mobilization (Kelly, et al., *Mol Ther* 15, 211-219 (2007)). Thus a phase I trial utilizing bone marrow (BM) as the source of CD34+ cells was initiated [National Clinical Trials registry ID: NCT01331018]. However, to successfully isolate CD34+ cells from whole BM products, unwanted red blood cells (RBC) must be depleted. RBC depletion is commonly accomplished by density centrifugation in polysaccharide media; however, for FA more gentle sedimentation in hetastarch (HES)-based media without centrifugation is preferable (Gonzalez-Murillo, et al., *Hum Gene Ther* 21, 623-630 (2010)). The challenge faced with sedimentation was how to deplete RBC from >1L of starting BM product in a very small amount of time, as the first patient enrolled weighed 70 kg and target collection volume was 15 mL BM for every 1 kg of body weight (i.e. >1L of starting BM volume).

To accomplish this, a HES sedimentation method for up to 1.8L of bone marrow was developed using novel, customized programming for the CliniMACS Prodigy™ device (Miltenyi Biotec GmbH). This device was developed to permit automated pre-processing, immunomagnetic labeling and separation of target cells, including CD34+ cells and T cells, from human APH products (Kaiser, et al., *Cancer Gene Ther* 22, 72-78 (2015); Spohn, et al., Automated CD34+ cell isolation of peripheral blood stem cell apheresis product. *Cytotherapy*, (2015)), and has already been shown to be capable of large scale, automated Ficoll-based RBC depletion from bone marrow (Sorg, et al., *Transfusion* 55, 1275-1282 (2015)). The custom program permitted >91% depletion of RBC with retention of ≥57% of the starting CD34+ cell population for human bone marrow products, as well as automated immunomagnetic bead labeling of CD34+ cells over a period of <6 hours total in a closed system (Table 8).

TABLE 8

Cell counts before and after automated processing to deplete human bone marrow RBCs from healthy adult donors.

| Sample | Species | Initial Vol. (mL) | Initial RBC ($10^{11}$) | Initial TNC ($10^8$) | Initial CD34+ ($10^6$) | Depleted Vol. (mL) | Depleted RBC ($10^{10}$) | Depleted TNC ($10^8$) | Depleted CD34+ ($10^6$) | % RBC Depleted | % Yield CD34+ |
|---|---|---|---|---|---|---|---|---|---|---|---|
| 1 | Human | 163 | 6.6 | 33.5 | 107.8 | 90 | 5.6 | 22.0 | 61.6 | 91.5 | 57.0 |
| 2 | (Healthy | 96 | 4.9 | 22.5 | 15.6 | 70 | ND | 14.6 | 15.0 | ND | 96.2 |
| 3 | Donor) | 93 | 4.8 | 44.6 | 52.3 | 71 | ND | 70.4 | 73.3 | ND | 140.2 |
| 4 | | 95 | 4.6 | 54.0 | 84.2 | 87 | 2.8 | 51.0 | 110.0 | 93.9 | 131.4 |

Based on this data, the first approval of a custom, mostly-automated program for this device under an investigator-held investigational new drug application with the United States Food and Drug Administration (FDA) was obtained (BB-IND-14675).

With this promising starting point, it was hypothesized that a patient-localized point-of-care and/or portable strategy for CD34+ cell gene transfer could be designed on this device, eliminating the need for local cGMP facility infrastructure (FIG. 1). The overall goal of these studies was rapid, mostly-automated production of ex vivo LV gene-modified patient-specific cell products suitable for human infusion which maintained hematopoietic repopulation potential. Here, the first proof-of-principle is demonstrated that a point-of-care and/or portable manufacturing process for ex vivo lentivirus-mediated gene modification of CD34+ stem cells is possible with this device, requires minimal user interface and other laboratory equipment, and results in viable gene-modified cellular products that meet current regulatory standards for infusion.

Materials and Methods. Approved Protocols and Subjects. All studies were conducted under protocols approved by the Institutional Animal Care and Use Committee (IACUC) and Institutional Review Board (IRB) in accordance with the Declaration of Helsinki. Cell products were purchased from commercial source (bone marrows; HemaCare Corporation) or obtained through institutional shared resources (mobilized apheresis products).

Lentiviral Vectors. The vector used in nonhuman primate transplantation (pRSC-SFFV.P140K.PGK.eGFP-sW) is a SIN lentiviral vector produced with a third-generation split packaging system and pseudotyped by the vesicular stomatitis virus G protein (VSV.G). Vector for these studies was produced by the institutional Vector Production Core (P. I. Hans-Peter Kiem) as part of the Core Center of Excellence in Hematology using a validated process. Infectious titers were determined by flow cytometric evaluation of eGFP expression following titrated transduction of HT1080 human fibrosarcoma-derived cells with research grade vector preparations. The clinical-grade anti-HIV vector used in gene transfer to human cell products (pRSC-H1.shCCR5.UbiC.C46.sEf1a.P140K-sW) is also a SIN lentiviral vector pseudotyped by the VSV.G protein. Clinical grade vector was produced by the Indiana University Vector Production Facility (IUVPF; Indiana, USA) using a large-scale validated process. The vectors were produced following Good Manufacturing Practice (GMP) guidelines under an approved Drug Master File held by IUVPF. Briefly, the anti-HIV LV was produced by means of transient four-plasmid transfection of 293T cells. Unconcentrated vector supernatant was concentrated 200-fold by tangential flow-based purification. The purified vector preparation was stored in 4.5 mL aliquots at −80° C. A complete description of vector characterization is included in Table 9. Infectious titer was measured through transduction of HT1080 cells with serial dilutions of vector and calculation of the copies of integrated vector per cell by quantitative (Taqman™) PCR.

Nonhuman Primate Transplantation Procedures. Pigtailed macaques (*Macaca nemestrina*) were housed at the Washington National Primate Research Center under conditions approved by the American Association for Accreditation of Laboratory Animal Care. Two juvenile macaques (Z13083 and Z13105) were primed with G-CSF (100 μg/kg) and SCF (50 μg/kg) by subcutaneous injection daily for 5 days, prior to bone marrow harvest. Bone marrow was collected in acid citrate dextrose and heparin under general anesthesia from both humeri and femora. Autologous CD34+ cells were isolated using biotinylated anti-CD34 (12.8) antibody and streptavidin-conjugated microbeads (Miltenyi Biotec) in a two-stage immunomagnetic separation performed on the Prodigy CliniMACS device following Program 2 and transduced twice with the sGbG lentiviral vector (LV) at a final multiplicity of infection (MOI) of 40 (20×2) following Programs 3-6. Following a fractionated dose of 1020 cGy total body irradiation (TBI) on day −2 and day −1, autologous gene modified CD34+ cells were infused back into the animals. Twenty-four hours following infusion of gene modified cells, animals received intravenous G-CSF (100 μg/kg/day) until stable neutrophil engraftment (ANC>0.5× $10^9$/L (500/μL)) was attained. Standard supportive care including sample transfusions, fluid and electrolyte management and antibiotics were administered as needed. Hematopoietic recovery was monitored by daily blood counts. Animals also received oral tacrolimus beginning at 3 mg/kg/day to achieve 10-15 ng/μL in serum as an immu-

TABLE 9

Characteristics of clinical grade anti-HIV LV vector.

| TEST | METHOD | RESULTS |
|---|---|---|
| Identity | | |
| Vector Function | Infection potential and chemoselection of TZM-bl and MAGI-CCR5 indicator cell lines | >2.5-fold inhibition of infection with HIV BaL >2-fold selection after O6BG/BCNU treatment |
| Vector Insert | Southern Blot Analysis | Vector size consistent with predicted fragment size and one additional band that is smaller than the predicted vector size* |
| Potency | | |
| Physical Titer | P24 ELISA | $6.9 \times 10^7$ pg/mL |
| Infectious Titer | Serial dilution on HT1080 cells assessed by qPCR | $7.7 \times 10^8$ IU/mL |
| Purity | | |
| Sterility | Aerobic and anaerobic culture for bacteria and fungus | No growth within 14 days |
| Mycoplasma | Culture and Vero indicator cells | Negative |
| In vitro viral assay | Assay on MRC-5, Vero and A549 cells | No CPE or hemadsorption |
| Replication competent lentivirus (RCL) testing | Co-culture of end production cells with C8166 cells with amplification and indicator phases | No evidence of RCL |
| | Supernatant testing on C8166 cells with amplification and indicator phases | No evidence of RCL |
| Endotoxin | Limulus amebocyte lysate | >2.4 and <3.6 EU/mL |
| Residual Total DNA | Quantitaive PCR | $1.91 \times 10^7$ fg/μL |
| Residual benzonase | ELISA | <0.195 ng/mL at 1:1.11 and 1:10 dilutions |
| Transfer of Residual E1A | Quantitative PCR | Negative |
| Transfer of Residual SV40 | Quantitative PCR | Negative |

*Smaller fragment size corresponds with intronic splicing within the UbiC promoter element (Cooper, et al., *Nucleic Acids Res* 43, 682-690 (2015)).

nosuppressant to minimize rejection of eGFP-expressing cells. Tacrolimus taper was initiated within 6-months to 1-year after transplant once stable gene marking was observed in peripheral blood.

Immunodeficient Mouse Transplantation Procedures. NOD.Cg-Prkdc scid Il2ry tm1 Wj/Szj (NOD/SCID/ IL2rγnull, NSG) mice between 8-12 weeks old received 270 cGy total body irradiation. Four hours after TBI, mice received an injection of $1 \times 10^6$ gene modified CD34+ cells resuspended in PBS containing 1% heparin (APP Pharmaceuticals, Schaumburg, Ill.) via tail vein infusion. Blood samples were collected by retro-orbital puncture at weeks 6, 10, and 12 weeks post infusion. At 12 weeks the mice were sacrificed and the spleen and bone marrow were harvested for analysis. Organ samples were filtered through a 70 mm filter (BD Biosciences) and washed with PBS. Blood and tissue samples were stained with appropriate FACS antibodies for 15 minutes at room temperature. RBC were removed by incubation in BD FACS Lysing Solution (BD Bioscience), which was diluted out using PBS prior to analysis by flow. Stained cells were acquired on a FACS Canto II (BD Bioscience) and analyzed using FlowJo software v10.0.8 (Tree Star Inc., Ashland, Oreg.). Analysis was performed on up to 20,000 cells in the viable cell population, and gates were established using full minus one (FMO) stained controls. Samples were stained at a 1:20 dilution using anti human CD45-PerCP (clone 2D1), CD3-FITC (clone UCHT1) CD4-V450 (clone RPA-T4), CD20-PE (clone 2H7), and CD14-APC (clone M5E2). Bone marrow was also stained with anti-human CD34-APC (clone 581). All antibodies were purchased from Beckton Dickinson.

Procedures for Semi-Automated, Mostly Closed Processing of Samples. For all products, initial blood cell counts and differential analyses were obtained using either a KX-21N (Sysmex) or AcTdiff2 (Coulter) automated hematology analyzer. For BM products, desired % hematocrit (HCT) for automated processing is ≤25%. Products with initial HCT >25% were manually diluted with PlasmaLyte A (Baxter) via sterile tubing prior to semi-automated processing. Complete blood cell counts and differential analyses were repeated following dilution to confirm target HCT content. A total of nine programs were developed for semi-automated processing (Numbered SW1-SW9 with subprograms designated J1-J9 respectively), which are described in detail in Table 10.

TABLE 10

Complete Description of Custom, Flexible Program Inventory

| Program Number | Tubing Set |
|---|---|
| J1 | TS100 |
| J2 | TS100 |
| J3 | TS100 |
| J4 | TS100 |
| J5 | TS100 |
| J6 | TS730 |
| J7 | TS730 |
| J8 | TS730 |
| J9 | TS730 |

A tubing set combining the functionality of TS100 and TS730 can also be used, in particular embodiments, eliminating the need for a mid-process tubing set change. Various combinations of these programs were used for processing of each product type. These are briefly described below. For all products, the initial tubing set used (TS100; Miltenyi Biotec) was pre-installed onto the device as part of the initial program setup (either Program 1 or Program 5) and an automated tubing set integrity test was performed by the device prior to product entering the tubing set for processing. Prior to installation, diluted product, Buffer (e.g. PBS/EDTA) (Miltenyi Biotec), HES (Hospira) and diluted cell product were sterile-docked onto the pre-fabricated tubing set. For CD34+ cell enrichment from human products, CliniMACS CD34 reagent (Miltenyi Biotec) was used. Intravenous immunoglobulin (10% IVIg; Baxter) was used as a blocking agent in all labeling programs. CD34 reagent and IVIg were pre-loaded into separate syringes which were sterile-docked onto the pre-fabricated tubing set when prompted by the device programming for labeling. Complete transduction media for all experiments consisted of StemSpan animal component-free media (Stem Cell Technologies) containing 100 ng/mL each recombinant human growth factors SCF (Miltenyi Biotec), TPO (PeproTech) and FLt3L (Miltenyi Biotec) and 500 nM UM 729 (kindly provided by Dr. Guy Sauvageau; Université de Montréal).

For monkey products, which consisted of G-CSF and SCF primed BM collected in ACD-A and heparin, the program combination used was as follows: 1, 3, 4, 6, 7, 8 and 9. Briefly, diluted products were first RBC depleted via HES sedimentation, then washed and concentrated in preparation for CD34 cell labeling using Program 1. A two-step labeling protocol was then performed since the anti-CD34 antibody used (12.8) is not directly conjugated to a magnetic bead using Program 3. Each labeling step included 30-minute incubation at 4° C. with slow rotation in the device chamber. Following labeling, product was washed and concentrated in preparation for immunomagnetic column selection. Magnetic column-based selections were then accomplished with Program 4. Resulting products were divided into a Negative Fraction Bag and a Target Cell Bag included in the pre-fabricated tubing set. The TS100 tubing set was then removed and Program 6 was initiated. This program includes pre-installation and tubing set integrity testing for the TS730 tubing set (Miltenyi Biotec). Following installation, the Target Cell Bag from the original TS100 was sterile-docked onto the same position of the TS730 tubing set. Complete transduction media and concentrated LV vector were pre-loaded into separate positions on the tubing set via sterile-docking. Program 6 encodes to a media exchange to remove selection buffer and replace with complete transduction media. Following exchange, a pre-determined LV vector volume was added to the cell suspension to begin transduction in the device chamber. Program 8 was then used to culture the cells in the device chamber under 5% $CO_2$ and 37° C. with a gentle mix of the cell suspension every 30 minutes for an overnight incubation. Twelve hours later, Program 7 was used to add a second vector dose, as well as additional media to the chamber to maintain a cell suspension of $1 \times 10^6$ cells per mL. Program 8 was then resumed to continue culture for a period of at least 4 hours. Finally, Program 9 was initiated to terminate transduction by washing the cell suspension to remove media and LV vector. This program includes final formulation of the product for infusion into Plasma Lyte A containing 5% human serum albumin (Baxter) in a 200 mL transfer pack pre-labeled with the autologous subject ID. This product bag was sterile-welded on the device to remove it for final product sampling and transport to infusion.

For human BM products, which were harvested into ACD-A and heparin, the program combination used included programs 1, 2, 4, 6, 7, 8 and 9. Semi-automated processing was identical to that performed for monkey BM products with the exception that single-step labeling of CD34+ cells was accomplished with Program 2 as there is a directly-conjugated anti-human CD34 magnetic bead available from Miltenyi Biotec. MOI for human BM CD34+ cells was 20 IU/cell (10×2).

For human mobilized APH products, no RBC depletion was required. Thus, fewer programs were needed for complete processing. The program combination used for APH products included programs 5, 6, 7, 8, and 9. Program 5 includes initial washing of the product to remove platelets. The program then continues to labeling and selection of CD34+ cells with final products transferred to Negative Fraction and Target Cell Bags on the pre-fabricated TS100 tubing set. Programs 6-9 were run as described for both monkey and human BM products. MOI for human mobilized APH CD34+ cells was 20 IU/cell (10×2).

Colony-forming cell (CFC) assays and LV-specific PCR assessment for transduction. Transduced and mock-transduced (exposed to the same media and culture conditions as transduced cells, but without the addition of LV vector) cells were cultured at 1,000-3,000 cells per 35 mm dish in 1.2 mL Methocult 4234 (Stem Cell Technologies) containing 100 ng/mL each of the recombinant human growth factors SCF (Amgen), G-CSF (Amgen), erythropoietin (EPO), TPO, granulocyte macrophage (GM)-CSF (Miltenyi Biotec), interleukin (IL) 3 and IL-6 (both from PeproTech). Culture conditions were 37° C., 85% relative humidity and 5% $CO_2$ for 14 days. After culture, colonies were counted to determine the number of colony-forming cells (CFC) per 100,000 cells plated. At least 80 individual colonies were picked for each experiment by manual pipetting into sterile tubes containing molecular grade water (HyClone) and protease K (Sigma). Genomic DNA was isolated by incubating tubes at 95° C. for 2 hours on a thermal cycler. Crude DNA preparations were then subjected to PCR using LV-specific primers [Fwd: 5'-AGAGATGGGTGCGAGAGCGTCA-3' (SEQ ID NO: 1) and Rev: 5'-TGCCTTGGTGGGTGCTACTC-CTAA-3' (SEQ ID NO: 2)] and, in a separate reaction, actin-specific primers which were designed for each species [monkey Fwd: 5'-TCCTGTGGCACTCACGAAACT-3' (SEQ ID NO: 3) and Rev: 5'-GAAGCATTTGCGGTGGAC-GAT-3' (SEQ ID NO: 4) and human Fwd: 5'-TCCTGT GGCATCGACGAAACT-3' (SEQ ID NO: 5) and Rev: 5'-GAAGCATTTGCGGTGGACGAT-3' (SEQ ID NO: 6)]. Colonies containing expected bands for both LV and actin were scored as transduced. Reactions which did not yield actin products were considered non-evaluable.

Liquid culture assays. Transduced and mock-transduced cells were sub-cultured in Iscove's Modified Dulbecco's Medium (IMDM; Life Technologies) containing 10% heat-inactivated fetal bovine serum (Life Technologies), 1% penicillin-streptomycin (Life Technologies) and 100 ng/mL of each of the following recombinant human growth factors: SCF, G-CSF, Flt3L, TPO, IL-3 and IL-6. Culture conditions were 37° C., 85% relative humidity and 5% $CO_2$ for up to 11 days. At two time points after sub-culture, typically 5 and 10 days, cells were collected, washed in sterile D-PBS (Life Technologies) and subjected to analysis of gene marking.

Analysis of gene marking. Leukocytes were isolated from transduction cultures or from heparinized peripheral blood or BM by ammonium chloride lysis at multiple time points after transplantation. For monkey cells transduced with the eGFP-expressing SIN LV, gene marking levels were determined by flow cytometry on a Canto or LSRII cell analysis machine (both from Beckton Dickinson). Flow cytometric data were analyzed by FlowJo version 10.0.7 (Tree Star Inc.) or CELLQuest Pro version 5.1 software (Beckton Dickinson). Transgenic eGFP protein expression in total leukocytes, granulocytes, monocytes and/or lymphocyte populations was determined by gating to exclude fewer than 0.1% of control cells in the relevant region based on forward and right-angle (side) light scatter characteristics or 2-color flow cytometry when cells were stained with antibodies to human CD3 (clone UCHT1), CD4 (clone RPA-T4), CD8 (clone), CD20 (clone 2H7) or CD34 (clone 563). All antibodies were purchased from Beckton Dickinson. For human cells transduced with the clinical anti-HIV LV vector, gene marking was analyzed by TaqMan 5' nucelase quantitative real-time PCR assay. Genomic DNA was extracted from isolated leukocytes using either the Blood DNA Mini kit or the Gentra Puregene Blood kit (both from Qiagen) according to the manufacturer's instructions. Sample DNA was analyzed in at least duplicate with a LV-specific primer/probe combination [Fwd: 5'-TGAAAGCGAAAGGGAAACCA-3' (SEQ ID NO: 7), Rev: 5'-CCG TGC GCG CTT CAG-3 (SEQ ID NO: 8), Probe: 5'-AGCTCTCTCGACGCAG-GACTCGGC-3' (SEQ ID NO: 9)]. In a separate reaction, a β-globin-specific primer/probe combination was used to adjust for equal loading of genomic DNA per reaction [Fwd: 5'-CCTATCAGAAAGTGGTGGCTGG-3' (SEQ ID NO: 10), Rev: 5'-TTGGACAGCAAGAAAGTGAGCTT-3'(SEQ ID NO: 11), Probe: 5'-TGGCTAATGCCCTGGCCCA-CAAGTA-3' (SEQ ID NO: 12)]. Standards consisted of dilutions of DNA extracted from a clonal cell line transduced with a single copy of LV provirus and DNA from the same parental cell line without gene modification. Reactions contained genomic DNA, appropriate primer/probe combination, ABI Master Mix (Applied Biosystems) and were run on the ABI Prism 7500 Sequence Detection System (Applied Biosystems) under the following thermal cycling conditions: 50° C. for 2 minutes and 95° C. for 10 minutes, then 40 cycles of 95° C. for 15 seconds and 60° C. for 1 minute.

Lentivirus insertion site analysis. Genomic DNA isolated from bulk leukocytes was subjected to LV-specific amplification of provirus-genome junctions by modified genomic sequencing (MGS)-PCR as described (Beard, et al., *Methods Mol Biol* 1185, 321-344 (2014)). The Vector Integration Site Analysis Server (https://visa.pharmacy.wsu.edu/bioinformatics) was used to process and map vector-genome junctions to either the Genome Reference Consortium build Grhg38 of the human genome or the Beijing Genomics Institute build rheMac3 of the rhesus genome (24). Sequences that could not be confidently localized to the appropriate genome were removed from the dataset prior to analysis. Clonality was assessed by ranking each unique insertion site by sequence abundance and normalizing to the total non-unique, localized number of insertion site sequence reads recovered for each sample.

Results. All experiments were performed in a non-cGMP laboratory with a benchtop CliniMACS Prodigy™ device. Additional equipment included a biosafety cabinet, refrigerator and freezer, automated blood cell counter, sterile tubing welder, general laboratory equipment (e.g. pipets, balance), and personal protective equipment intended to simulate anticipated conditions in clinical facilities of underdeveloped countries. As a proof-of-principle CD34+ cells from granulocyte colony stimulating factor (G-CSF) mobilized APH products collected from healthy human donors were first isolated and gene modified. This starting cell product was chosen because it is the most common source of CD34+ cells in adult gene therapy patients, and because the existing device software was designed for automated preparation and CD34+ cell isolation from APH products. Here RBC reduction was not required and initial programming included washing to remove platelets prior to CD34+ labeling (Table 10). The complete process required a total of four custom programs for manufacturing, and took 25 hours from receipt of the starting APH product to preparation of the final infusion product (APH Donor 1 and APH Donor 2) (Table 11).

TABLE 11

Total time and hands-on operator time required for each semi-automated process.

| Source Product | Start Time (Day-1) | End Time (Day 0) | Total Process Time (Hrs) | Mean Total Process Time (Hrs) | Total Hands-on Time Required (Hrs:Mins) | Mean Hands-on Time Required (Hrs:Mins) |
|---|---|---|---|---|---|---|
| Hu APH Donor 1 | 11:19 | 11:50 | 25 | 25 | 2:10 | 3:25 |
| Hu APH Donor 2 | 11:10 | 11:50 | 25 | | 4:39 | |
| Hu BM Donor 1 | 07:15 | 10:04 | 27 | 27.5 | 2:56 | 2:59 |
| Hu BM Donor 2 | 08:00 | 13:38 | 28 | | 3:01 | |
| NHP BM (Z13105) | 07:58 | 15:50 | 32 | 30 | 4:45 | 3:44 |
| NHP BM (Z13083) | 09:30 | 13:26 | 28 | | 2:43 | |

Two different pre-fabricated device tubing sets were needed for this process to access all required device components needed during processing (see Materials and Methods and Table 10). CD34+ cell enrichment from APH products resulted in highly pure populations with ≥96% of enriched cells expressing CD34, with enrichment efficiency of 42% and 87% for the two donors (Table 12).

TABLE 12

Cell counts before and after automated processing of healthy human G-CSF mobilized leukapheresis products.

| Sample Parameter | Hu APH Donor 1 | Hu APH Donor 2 |
|---|---|---|
| Initial APH volume (mL) | 223 | 227 |
| Initial RBC ($10^{11}$) | 0.86 | 0.50 |
| Initial % Granulocytes | 30.7 | ND |
| Initial TNC ($10^8$) | 563.7 | 455.0 |
| Initial CD34+ (%) | 0.6 | 0.9 |
| Initial CD34+ ($10^6$) | 338.2 | 413.9 |
| Enriched CD34+ ($10^6$) | 141.7 | 359.7 |
| Enriched CD34+ Purity (%) | 98.7 | 96.0 |
| CD34+ Yield (% of Initial) | 42.0 | 86.9 |

ND: Not determined; value too low for automated blood cell counter to report.

These values are within the expected range for APH products selected on the first generation CliniMACS™ device. Absolute yields were $1.4 \times 10^8$ and $3.6 \times 10^8$ CD34+ cells for APH Donors 1 and 2, respectively.

Figure 12A:
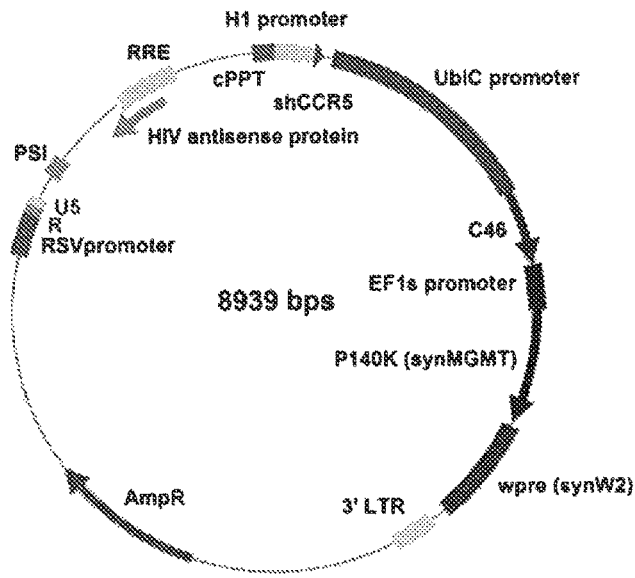
FIGS. 12A-B. Both vectors are third-generation self-inactivating lentiviruses derived from the same HIV-1 backbone.

Gene transfer was then performed with an anti-HIV LV vector currently being tested in a phase I clinical trial for patients with AIDS-related lymphoma at the Fred Hutchinson Cancer Research Center [NCT02343666]. The LV vector used in these studies was a self-inactivating (SIN) HIV-1 derived backbone currently used for most clinical trials of HSC gene therapy worldwide. The engineered LV encoded three separate therapeutic transgenes: two anti-HIV transgenes and a P140K mutant methylguanine methyltransferase (MGMT) transgene (Beard, et al., J Clin Invest 120, 2345-2354 (2010)) to allow for in vivo selection of gene modified cells if low levels of engraftment are observed (FIG. 12A). The anti-HIV transgenes included a short hairpin RNA analgous to the CCR5 transcript and the C peptide, C46. The CCR5 short hairpin activates RNA interference pathways in the cell in which it is expressed, resulting in degradation of CCR5 transcripts and loss of functional CCR5 proteins on the cell surface. Since CCR5 is a common co-receptor for HIV entry into target cells, lack of CCR5 expression can inhibit HIV infection. The C46 peptide is a 46 amino acid fragment of gp41 which, when expressed on target cells, prevents fusion of HIV particles with the cell membrane, inhibiting HIV entry, regardless of which co-receptor is used. The multiplicity of infection (MOI) was 20 infectious units (IU) per cell, as this vector:cell ratio is currently approved by the FDA for manufacturing. The length of vector exposure in these experiments was 12-14 hours and no pre-culture to stimulate cell division was performed (see Materials and Methods). Most notably, the culture chamber on the device was not pre-coated with recombinant human fibronectin fragment (retronectin), which is commonly used to enhance LV transduction, as this would prevent cell removal from the device chamber during final harvest. Additionally, the pyrimidoindole derivative, UM 729, was included in transduction cultures for these experiments as this molecule is reported to expand primitive hematopoietic cells ex vivo (Fares, et al., Science 345, 1509-1512 (2014)).

Figure 13A:
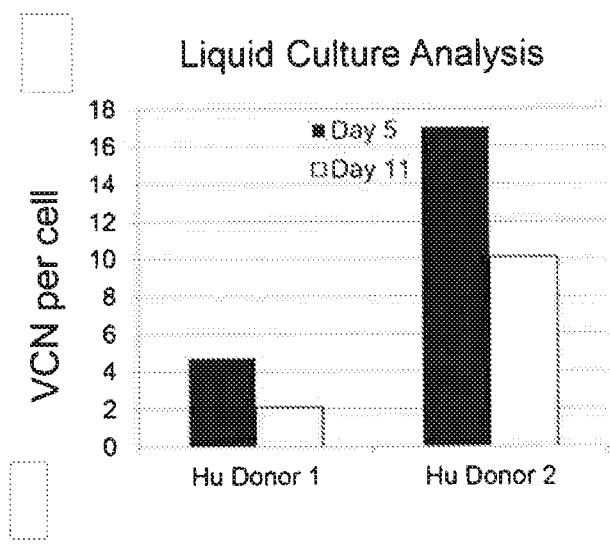
FIGS. 13A-B. Gene marking in growth factor mobilized peripheral blood CD34+ leukocytes following automated transduction. Following semi-automated transduction and harvest, aliquots of the final cell product were cultured in liquid media including recombinant human growth factors GCSF, SCF, TPO, Flt3-L, IL-3 and IL-6 for subsequent real-time PCR to determine VCN (FIG. 13A), or in methylcellulose media containing the same recombinant human growth factors for colony forming assay (FIG. 13B) for subsequent real-time PCR to determine VCN.
Figure 13B:
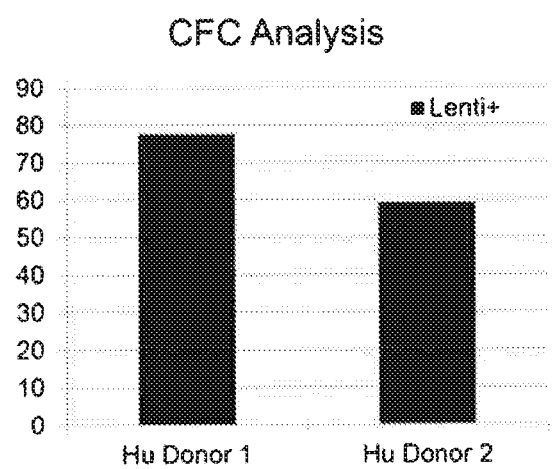
Figure 14:
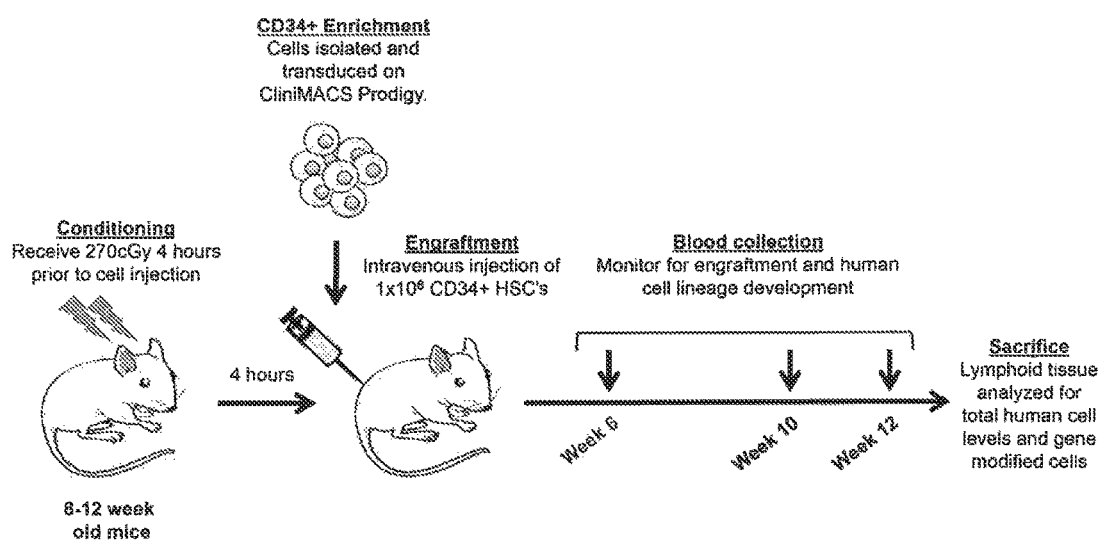
FIG. 14. Adult NSG mice ranging between 8-12 weeks of age received a sub-lethal dose (270 cGy) of radiation 4 hours prior to intravenous injection of $1 \times 10^6$ human CD34+ cells isolated from mobilized apheresis donors on the CliniMACS Prodigy device. Mice were then followed for 12 weeks with blood collection samples taken at weeks 6, 10, and 12 post-transplant. At 12 weeks, the animals were sacrificed and lymphoid tissues were analyzed for both total human cell levels as well as frequency of gene modification.

A large donor-to-donor variation was observed in mean vector copy number (VCN) per cell from bulk liquid cultures maintained for 10 days (2.1 and 10.1 vector copies per cell, respectively) (FIG. 13). Colony forming cell (CFC) gene transfer efficiencies were 77.7% and 59.3%, respectively (FIG. 13). A marked decrease in the CFC content of the product was observed with higher VCN in liquid cultures (Hu APH Donor 2; 0.9%) compared to the other donor (Hu APH Donor 1; 26.2%). To assess product fitness, release testing and xenotransplantation of resulting cell products were performed into immunodeficient (non-obese diabetic (NOD)/severe combined immunodeficiency (SCID) gamma−/−, NSG) mice following sub-lethal total body irradiation (TBI) (FIG. 2). Both products met all cGMP immediate release criteria for infusion (Table 13).

TABLE 13

Regulatory safety testing results of products manufactured by semi-automated process.

| | | Measured Result | | |
|---|---|---|---|---|
| Test | Required Result | APH Donor 1 | APH Donor 2 | BM Donor 2 |
| Gram Stain | Negative | Negative | Negative | Negative |
| 3 Day Sterility† | Negative | Negative | Negative | Negative |
| 14 Day Sterility† | Negative | Negative | Negative | Negative |
| Mycoplasma | Negative | Negative | Negative | Negative |
| Endotoxin‡ | ≤0.5 EU/mL | ≤0.5 EU/mL | ≤0.5 EU/mL | ≤0.5 EU/mL |
| Cell Viability by Trypan Blue Dye Exclusion | ≥70% | 82.5% | 91.5% | 71.0% |

APH: apheresis; BM: bone marrow; EU: endotoxin units.
†Final release sterility testing performed by LABS ™ includes bacterial, fungal and yeast testing over 14-day incubation under USP<71> guidelines in controlled cleanrooms.
‡Endotoxin levels determined by kinetic turbidimetric method utilizing limulus amebocyte lysate (LAL) reagent.

Figure 15A:
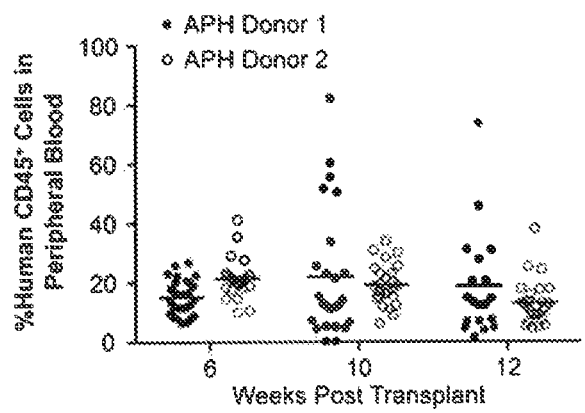
FIGS. 15A-C.
Figure 15B:
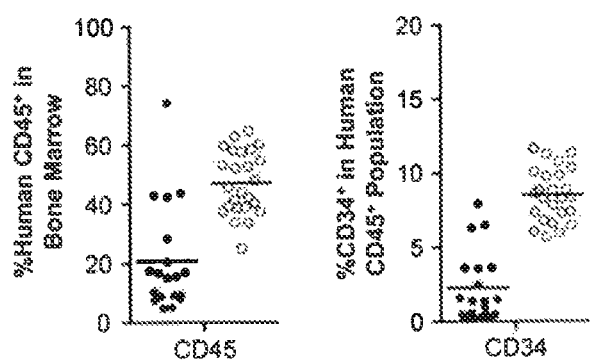
Figure 15C:
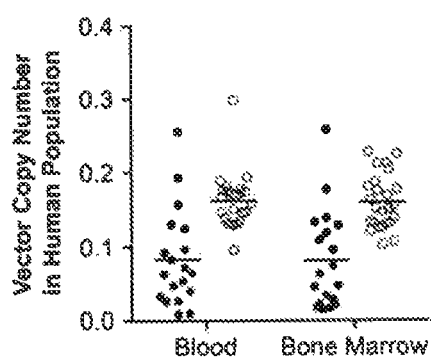

Moreover, robust engraftment of human CD45+ cells from both products was observed in the peripheral blood and bone marrow of xenotransplanted mice over 12 weeks following infusion (FIG. 15). At 12 weeks after infusion, all mice were euthanized and gene modified cell engraftment in blood and BM was determined. A mean VCN per cell in blood of 0.083 and 1.7 for APH Donor 1 and APH Donor 2, respectively (FIG. 15C) was observed. Mean VCN per cell was equivalent between blood and BM for each animal cohort, and was higher in mice receiving cells from APH Donor 2, consistent with the higher VCN observed in liquid cultures. These data indicate that isolation and LV transduction of CD34+ cells is possible from mobilized APH products in an overnight method with this automated, closed-system platform.

This automated process was next expanded for BM products. BM is the source of CD34+ cells for gene therapy in very young patients and other patients for whom mobilization is contraindicated, such as FA. However, less published data is available on the isolation of CD34+ cells from BM products. BM from three healthy adult donors was collected and modified programming for immunomagnetic bead-based separation of CD34+ cells following HES sedimentation of RBC. This lengthened the total manufacturing time by a few hours, but maintained the reduced total hands-on operator time required (Table 11). Between 42% and 57% yield of the starting CD34+ cell population at >72% purity following HES sedimentation and CD34 enrichment from each of three different donor products was achieved, which was similar to CD34+ cell yields observed in APH products, although at the lower end of the range observed (Table 14).

TABLE 14

Cell counts before and after automated processing of healthy human bone marrow products.

| Sample Parameter | Hu BM Donor 1 | Hu BM Donor 2 | Hu BM Donor 3 |
|---|---|---|---|
| Initial BM volume (mL) | 96 | 93 | 95 |
| Initial RBC ($10^{11}$) | 4.9 | 4.7 | 4.6 |
| Initial TNC ($10^8$) | 22.5 | 44.6 | 54.0 |
| Initial CD34$^+$ (%) | 0.7 | 1.2 | 1.6 |
| Initial CD34$^+$ ($10^6$) | 15.6 | 52.3 | 84.2 |
| Depleted RBC ($10^{10}$) | ND | ND | 2.8 |
| Depleted TNC ($10^8$) | 14.6 | 70.4‡ | 51.0 |
| Depleted CD34$^+$ (%) | 1.0 | 1.0 | 2.2 |
| Depleted CD34$^+$ ($10^6$) | 15.0 | 73.3‡ | 110.0‡ |
| Enriched CD34$^+$ ($10^6$) | 8.87 | 21.8 | 43.4 |
| Enriched CD34$^+$ Purity (%) | 86.1 | 72.7 | 95.3 |
| CD34$^+$ Yield (% of Initial) | 56.8 | 42.0 | 51.5 |

ND: Not determined, cells were counted using a Coulter Counter which does not report RBC content.
‡Values recorded are higher than the initial product. Counts were repeated a total of three times and values were consistent for all three determinations. Reported value is the average of three determinations.

Due to clinical grade vector quantities available, LV mediated gene transfer in two of these three products (Hu BM Donor 1 and Hu BM Donor 2) was performed.

Figure 16A:
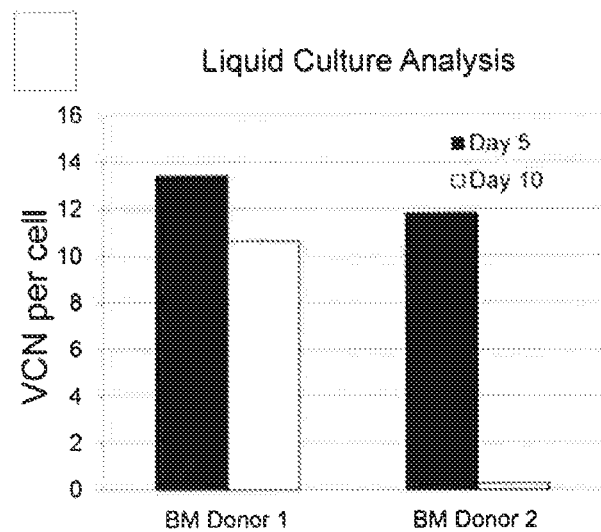
FIGS. 16A-B. Gene marking in human bone marrow CD34+ cells following automated transduction. Following semi-automated transduction and harvest, aliquots of the final cell product were cultured in liquid media including recombinant human growth factors G-CSF, SCF, TPO, Flt3-L, IL-3 and IL-6 for subsequent real-time PCR to determine VCN (FIG. 16A), or in methylcellulose media containing the same recombinant human growth factors for colony forming assay (FIG. 16B) for subsequent real-time PCR to determine VCN.
Figure 16B:
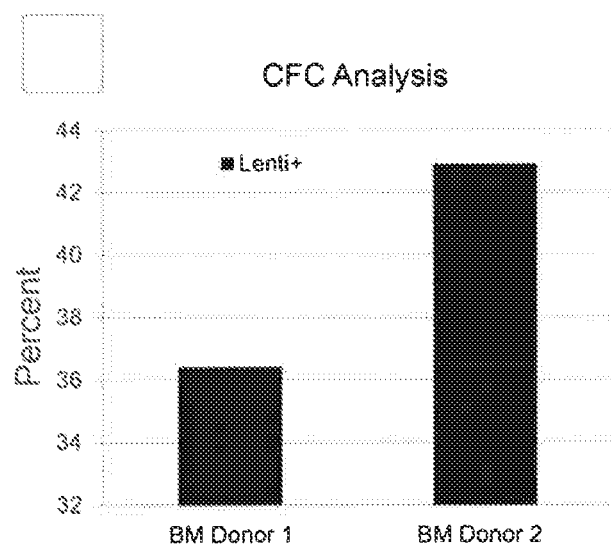

For gene transfer the same anti-HIV LV vector applied in the transduction of APH products was performed under identical transduction conditions. For the first donor (Hu BM Donor 1), a total of $8 \times 10^6$ cells were obtained after CD34+ enrichment. Due to minimum volume restrictions within the culture chamber on the device, cell density during transduction culture was sub-optimal ($2.0 \times 10^5$ cells/mL). Additionally, low gas exchange within the chamber during the culture period was observed visualized as dark pink media coloration. Not surprisingly, a significant loss in cell viability (from 86% to 40%) occurred after transduction, despite an overall increase in viable cell number (from $8 \times 10^6$ to $12 \times 10^6$ total cells). Mean VCN in liquid cultures expanded ex vivo for 10 days was 10.6 copies per cell (FIG. 16A). A low colony forming cell (CFC) content (1.5%) for this product was observed, with only 36.4% of CFCs transduced (FIG. 16B). While these data indicate that human BM CD34+ cell enrichment and transduction are possible in this automated, semi-closed system, conditions were sub-optimal relative to current clinical trial experience.

Figure 17A:
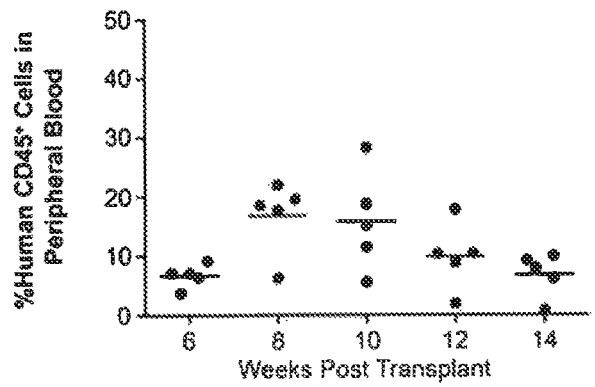
FIGS. 17A, 17B and 17C. Human steady state BM CD34$^+$ cells produced using point-of-care and/or portable manufacturing engraft into immunodeficient mice. (A) Human CD45$^+$ blood cell engraftment levels in individual adult NSG mice receiving LV transduced BM-derived CD34$^+$ cells at various time points post injection. All animals were sacrificed at 14 weeks following transplant and BM was analyzed for human CD45$^+$ and CD34$^+$ blood cell content (B), as well as LV gene marking (C).
Figure 17B:
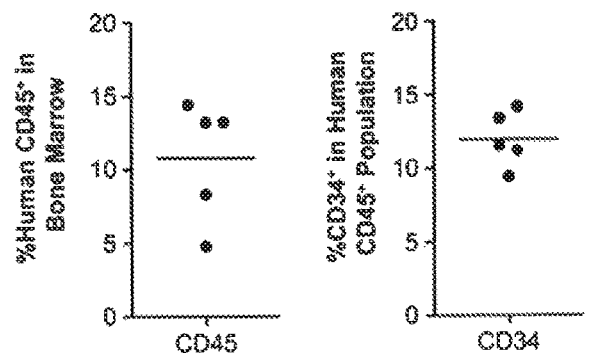
Figure 17C:
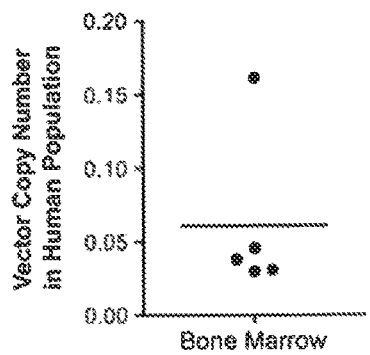

To rule out whether observed results were donor-specific, this process was repeated with BM from a second individual (Hu BM Donor 2). While similar overall CD34 enrichment efficiency (42%) and purity (73%) were observed compared to Hu BM Donor 1 (Table 14), a larger starting CD34+ cell population resulted in 3-fold more total CD34+ cells ($21.8 \times 10^6$) permitting optimal cell density during culture and transduction ($0.5-1 \times 10^6$ cells/mL). Transduction efficiency in 10-day bulk cultures following semi-automated processing was 0.3 vector copies per cell by PCR analysis (FIG. 16A). Here, CFC content was 3.0%, and a modest increase in the number of LV+ CFC for this donor (43%) was observed compared to Hu BM Donor 1 (36%) (FIG. 16B). Release testing was performed and all criteria were within current trial specifications deemed safe for infusion into patients (Table 13). Xenotransplantation of these cells was performed into NSG mice following the same transplantation procedures described for APH products. Stable engraftment of blood cells expressing human CD45 were observed in these animals up to 14 weeks after infusion (FIG. 17). At 14 weeks significant engraftment of human CD45+ and CD34+ white blood cells was observed in BM of recipient animals ranging from 5% to 15% (FIG. 17B). Up to 16% of BM cells were LV gene modified in these animals (FIG. 17C). These data indicated that BM products could also be manufactured using the point-of-care and/or portable platform, but further optimization of enrichment and culture for consistency should be performed.

Having established the proof-of-principle that point-of-care and/or portable manufacturing of LV gene modified CD34+ cells is possible, it was sought to establish that autologous cell products produced in this way were able to reconstitute hematopoiesis long term in a myeloablative setting. To test this the pigtailed macaque (*Macaca nemestrina*) transplantation model [reviewed in (Trobridge, et al., Gene Ther 17, 939-948 (2010))] was chosen. This model permits use of the same growth factors and media used in human cell product manufacture. However, available directly-conjugated reagents for CD34+ immunomagnetic selection of human samples are not cross-reactive with macaque cells. Therefore a modified two-step labeling program was created to allow indirect bead labeling by biotin-streptavidin affinity. Additionally, this model is susceptible to simian/human immunodeficiency virus (SHIV) infection, providing a clinically relevant system in which to test anti-HIV gene therapy.

Autologous lentivirus gene-modified nonhuman primate (NHP) CD34+ cell products were manufactured using this semi-automated platform and transplanted these into two animals (Z13105 and Z13083) following myeloablative TBI (1020 cGy). The total time required for manufacturing each NHP BM product from receipt to infusion averaged 30 hours with <4 hours of direct operator hands-on time which primarily included preparation of the initial product and in sampling following final formulation (Table 11). Not unexpectedly given a two-step labeling and enrichment process, lower efficiency of CD34+ cell enrichment from NHP BM products was observed (Table 15) compared to directly-conjugated bead 1-step labeling and enrichment of human cell products; however these cell yields were still sufficient for transduction and transplantation of juvenile monkeys weighing <4 kg.

TABLE 15

Cell counts before and after automated processing of NHP growth factor primed bone marrow.

| Sample Parameter | Z13105 | Z13083 |
|---|---|---|
| Initial BM volume (mL) | 27.0 | 35.0 |
| Initial RBC ($10^{11}$) | 1.74 | 1.92 |
| Initial TNC ($10^8$) | 37.0 | 73.0 |
| Initial CD34+ (%) | 8.02 | 4.7 |
| Initial CD34+ ($10^6$) | 296.7 | 343.1 |
| Depleted RBC ($10^{10}$) | 2.75 | 2.66 |
| Depleted TNC ($10^8$) | 30.2 | 60.6 |
| Depleted CD34+ (%) | 7.3 | 4.7 |
| Depleted CD34+ ($10^6$) | 220.5 | 286.0 |
| Enriched CD34+ ($10^6$) | 72.3 | 30.2 |
| Enriched CD34+ Purity (%) | 98.2 | 83.6 |
| CD34+ Yield (% of Initial) | 24.4 | 8.8 |

Figure 12B:
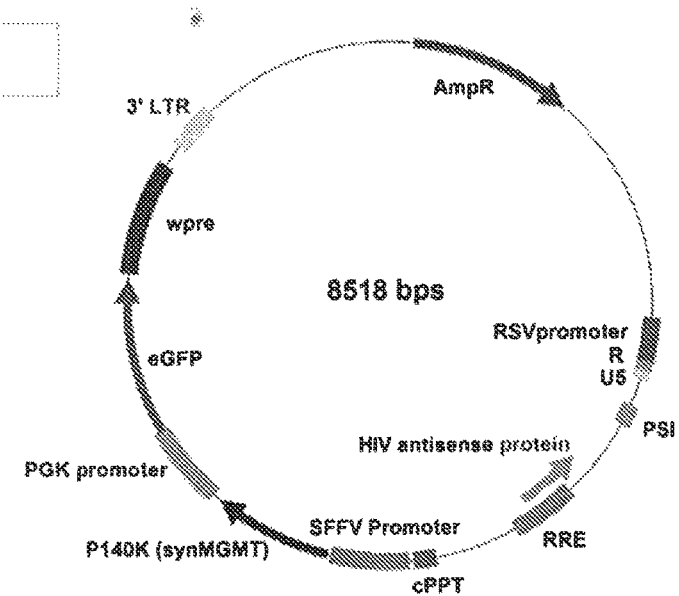

The LV vector used in these studies was the same vector backbone used for human product manufacture, but encoding an enhanced green fluorescent protein (eGFP) transgene to facilitate in vivo tracking of transplanted cells along with the P140K mutant MGMT transgene (FIG. 12B). To ensure a sufficient level of gene transfer, a multiplicity of infection (MOI) of 40 infectious units (IU) per cell was used during a two-hit transduction method (20 IU/cell×2). Total cell doses achieved were 27×$10^6$ and 5.4×$10^6$ CD34+ cells/kg body weight, respectively, reflecting a gain in the absolute number of cells after transduction in animal Z13105 (from 7.2×$10^7$ to 8.2×$10^7$ total cells), and a loss in the absolute number of cells after transduction for animal Z13083 (from 3.0×$10^7$ to 1.9×$10^7$ total cells). Transduction efficiency in colony-forming units was 23% and 39%, respectively, and 27.6% and 11.9% of cells kept in bulk culture expressed GFP at 11 days after transduction, respectively (FIG. 18). Engraftment, defined as a sustained absolute neutrophil count >500/mm3 and platelet count >20,000/mm$^3$, was observed within +23 days from transplant for both animals (FIG. 19 and Table 16).

TABLE 16

Summary of nonhuman primate transplant cell counts and engraftment.

| | Total CD34+ cell dose infused (cell dose/kg) | Total CFCs infused† (dose/kg) | Total gene modified CFCs infused€ (dose/kg) | Days to ANC >500 | Days to Platelets >20,000 |
|---|---|---|---|---|---|
| Z13105 | 81 × $10^6$ (30 × $10^6$) | 2.15 × $10^6$ (7.98 × $10^5$) | 5.8 × $10^5$ (2.1 × $10^5$) | 8 | 23 |
| Z13083 | 19 × $10^6$ (5.14 × $10^6$) | 1.52 × $10^5$ (4.1 × $10^4$) | 5.6 × $10^4$ (1.5 × $10^4$) | 12 | 14 |

†Number of cells in the infusion product with potential to generate colonies in a standard CFC assay. Value is extrapolated from the percentage of colonies generated from 3000 cells plated in a single assay.
€Number of gene modified cells in the infusion product with potential to generate colonies in a standard CFC assay. Value is extrapolated from the percentage of gene modified colonies generated from 3000 cells seeded in a single assay.

Notably, neither animal required unanticipated supportive care nor displayed evidence for increased toxicity, including potential contamination, resulting from the bench top production of genetically modified infused cell products.

Figure 19A:
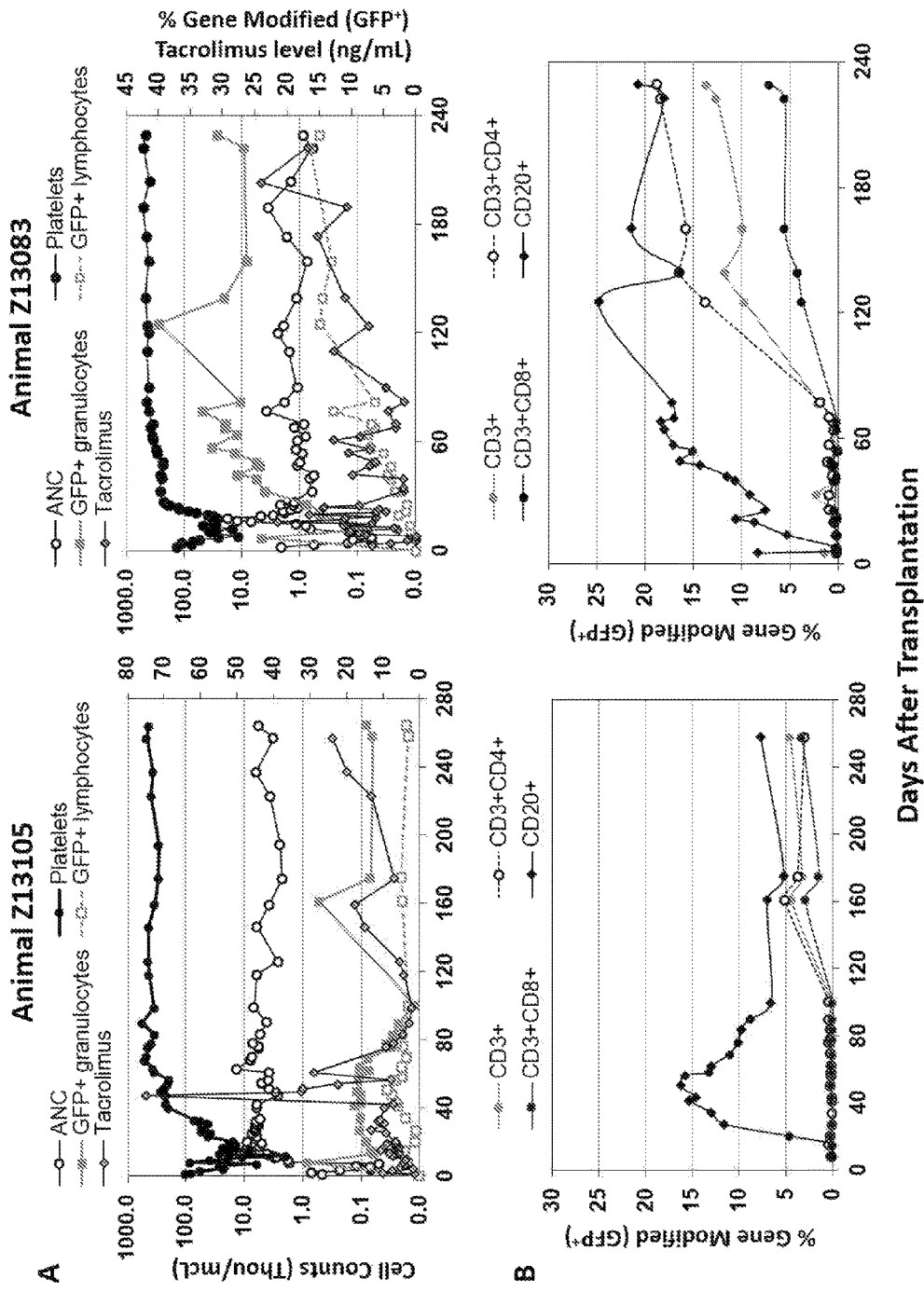
Figure 21:
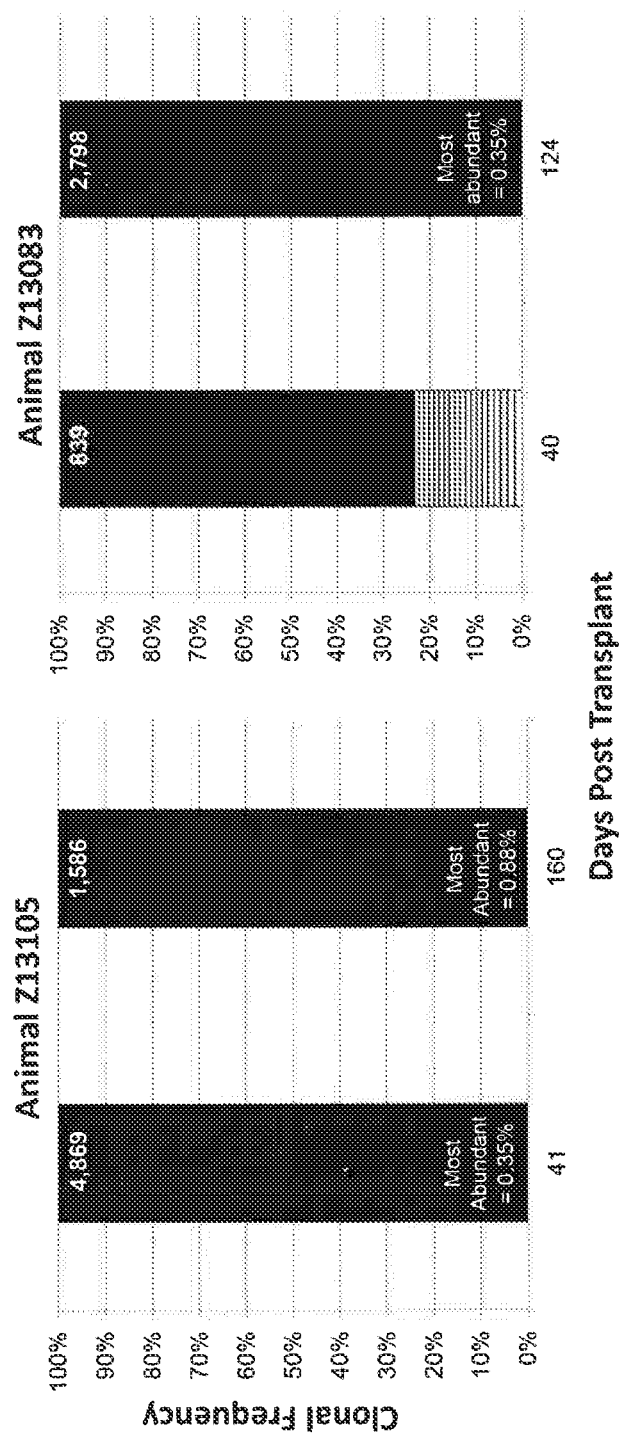
FIG. 21. Highly polyclonal engraftment of LV gene modified nonhuman primate CD34+ cells following point-of-care and/or portable production and transplant. Bar graphs represent the clonal diversity of lentivirus gene modified peripheral blood leukocytes collected at day +40 after transplant into autologous recipients as determined by genomic locus of lentivirus integration. Clonal integration site sequences which constituted ≥1% of all sequences captured are indicated by boxes in ascending order of frequency. Colored boxes indicate clones identified across time points. Total number of clones identified in each sample by this method are listed at the top of each bar. A total of 79 and 24 shared clones between the two time points evaluated for animals Z13105 and Z13083 was observed, respectively across all clones sequenced.

Stable, persistent gene marking was observed in peripheral blood leukocytes by eGFP expression within 1 month after infusion in both animals, reaching levels of 12% (FIG. 19A). At 6 months after transplant, up to 1.7% GFP+ RBC and 1.4% GFP+ platelets in these two animals (FIG. 20) was observed. As successful anti-HIV gene therapy will require gene-modified lymphocytes, reconstitution of this compartment after transplant (FIG. 19C) was tracked. Early after transplant (<100 days), nearly all eGFP+ lymphocytes were CD20+ B cells in both animals. However, beginning +100 days after transplant, increasing contributions of eGFP-expressing CD3+, CD4+ and CD8+ lymphocytes were observed. An unexpected reduction in the percent of eGFP+ granulocytes in animal Z13105 beginning at +76 days after transplant was observed, which reached a nadir of 1% eGFP+ granulocytes at +100 days after transplant, and corresponded to below-target tacrolimus (administered to prevent immune response against eGFP) dosing during this time (FIG. 19A). Upon re-targeting of tacrolimus dosing, eGFP+ granulocytes rebounded to 27%. To evaluate the clonal diversity of GFP+ cells, high-throughput LV integration site analysis was performed by modified genomic sequencing PCR (Beard, et al., *Methods Mol Biol* 1185, 321-344 (2014)). Highly polyclonal distribution of gene modified peripheral blood leukocytes were observed in each animal, without skewing toward dominant clones and without the need for chemotherapy-induced selection of gene modified cells in vivo (FIG. 21). Together these data demonstrate the safety and feasibility of point-of-care and/or portable manufacturing of LV gene modified CD34+ stem cells in a clinically relevant large animal model.

Discussion. Overnight manufacturing of LV gene-modified CD34+ repopulating cells in a small, self-contained benchtop platform suitable for point-of-care and/or portable implementation is demonstrated. Human BM and mobilized APH products can be processed in this way and meet current regulatory requirements for infusion in gene therapy clinical trials. Human products manufactured on this platform are capable of in vivo repopulation in an immunodeficient mouse model of xenotransplantation. Importantly, two myeloablated monkeys were successfully reconstituted for an extended period of time with autologous LV gene modified CD34+ cells produced using this system, without any adverse events related to the manufacturing methods used.

The range of blood stem cell gene therapy applications is expanding rapidly, especially for inherited diseases, HIV/AIDS and cancer [reviewed in (Ghosh, et al., Gene therapy for monogenic disorders of the bone marrow. *Br J Haematol*, (2015), Adair, et al., *J Clin Invest* 124, 4082-4092 (2014))]. Given that most of these studies were conducted at single institutions, and were limited to one dozen manufacturing facilities in seven countries (U.S., Spain, France, U.K, Italy, Germany and Australia), distribution of this approach is a major barrier to efficient translation of gene therapy into clinical practice. The flexibility and small footprint of this technology provides a major advantage to current state-of-the-art cell manufacturing. This platform and process could be implemented in clinic sites to vastly increase the availability of LV-mediated CD34+ cell gene therapy to greater numbers of patients for whom this treatment strategy has demonstrated success in early trials. Moreover, the same platform can be used to isolate and manufacture other types of gene-modified blood cell products, such as T cells, or to expand cord blood CD34+ cells, two treatment approaches which also have demonstrated increasing clinical utility [(Frantz, et al., *Nat Biotechnol* 29, 853-855 (2011)) and reviewed in (Thompson, et al., *Bone Marrow Transplant* 50 Suppl 2, S55-62 (2015))].

Nearly all LV blood stem cell gene therapy clinical trials have demonstrated the need for conditioning prior to infusion to achieve therapeutic levels of gene-modified cell engraftment. However, to confidently reconstitute hematopoiesis after conditioning, including non-myeloablative regimens, a minimum cell dose of $2 \times 10^6$ autologous CD34+ cells per kg of patient body weight would be required at the time of transplant. While extrapolated cell doses from human APH products manufactured in this study would easily achieve this threshold, CD34+ cell numbers from BM products would only be clinically useful for newborns weighing ≤10 kg. Thus, enrichment efficiency and purity will need to be further optimized for adult patient populations for whom BM is the desired source of CD34+ cells.

Figure 22A:
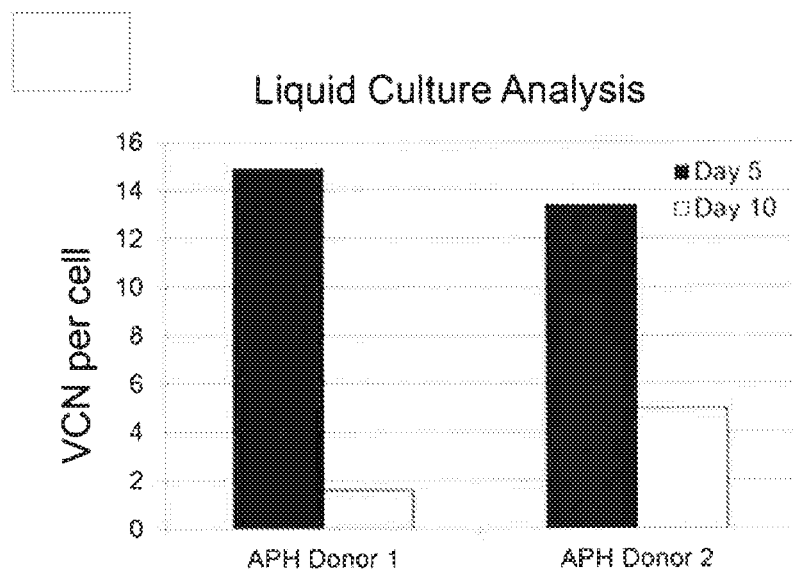
FIGS. 22A-B. Removal of UM729 from transduction conditions reduces vector copy number, but also colony-forming cell transduction efficiency. Following non-automated transduction of mobilized APH CD34+ cell products from Donors 1 and 2 in the absence of the pyrimidoindole derivative UM729, aliquots of the final cell product were cultured in liquid media including recombinant human growth factors GCSF, SCF, TPO, Flt3-L, IL-3 and IL-6 for subsequent real-time PCR to determine VCN (FIG. 22A), or in methylcellulose media containing the same recombinant human growth factors for colony forming assay (FIG. 22B) for subsequent real-time PCR to determine VCN.
Figure 22B:
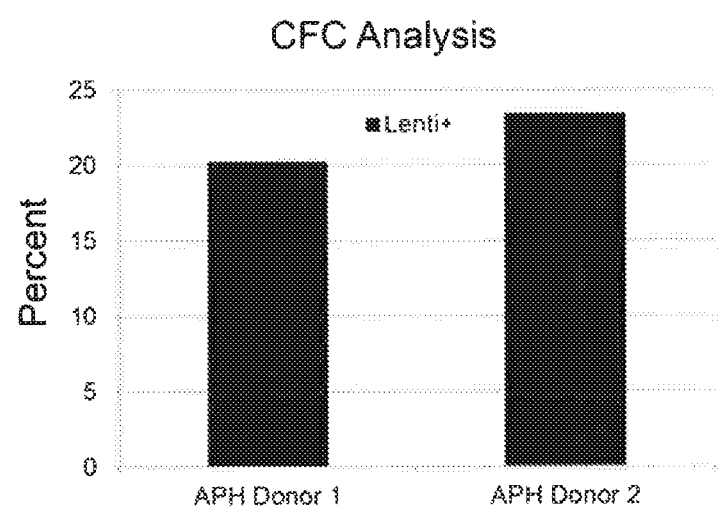

For widespread clinical implementation, the system must demonstrate reproducible production which meets the safety, quality, and sterility specifications ensured by cGMP principles to establish a consistent and well-controlled manufacturing process. Given the wide range of VCN per cell observed in the described studies, consistent transduction efficiency between donors will need to be addressed prior to clinical implementation. Importantly, targeting optimal levels of vector integration is a somewhat easier task than obtaining detectable gene transfer when it is either non-existent or sub-therapeutic. Indeed, the ability to lower VCN per cell when the pyrimidoindole derivative UM 729 is removed from transduction cultures (FIG. 22) has been determined in vitro. Further refinements to media components and culture and transduction conditions are easily implemented in this manufacturing process and will be systematically evaluated in future studies with larger numbers of donors to establish statistical significance.

To efficiently translate this system into clinical practice worldwide will also require further process streamlining. Logistically, the four to seven different custom programs required for complete manufacturing of the products described herein should be condensed into a single, modular program for this device. Finally, the need for trained staff is reduced, as the device interfacing during RBC depletion and media exchanges requires subjective input. A more optimal system will require the device, a single program with minimal requirement for user interface and a single-use kit including the tubing set and all required components for isolation, transduction, culture and harvest of autologous patient cells with minimal staff. Additionally, the regulatory challenge of classifying the medicinal product, autologous gene modified blood cells, which currently differs between the U.S. and the E.U., will need to be addressed.

Despite these challenges, the existing platform already provides a major advantage in terms of cost. In addition to the vastly lower cost associated with purchase of the parent device ($149,500 U.S.) compared to the cost of constructing a cGMP manufacturing facility (millions of dollars, U.S.), the actual direct cost of manufacturing autologous gene modified CD34+ cells using this point-of-care and/or portable platform averaged $26,000 (Table 17).

TABLE 17

Direct cost of point-of-care and/or portable manufacturing of LV gene modified CD34+ cells.

| Resource | Description | Costs (U.S. $) Automated BM Process | Costs (U.S. $) Automated APH Process |
|---|---|---|---|
| Materials and Supplies | Media and supplements | 1,645 | 1,645 |
| | Concentrated LV vector | 2,500 | 5,831 |
| | Laboratory Consumables | 100 | 100 |
| | Initial Cell Product | 5,997 | 6,600 |
| | Reagents and Accessories for CD34 Isolation | 7,077* | 7,008 |
| | GMP-grade Cytokines | 3,072 | 3,072 |
| | Garments | 27 | 27 |
| Personnel | Production personnel** | 832 | 832 |
| Utilities | Electricity, water and medical-grade gases | 250 | 250 |
| Quality Management | Batch release testing*** | 2,537 | 2,537 |
| Total Direct Costs | | 24,037 | 27,902 |

*Includes HES sedimentation prior to CD34 enrichment.
**Based on 4 hours of hands-on operator time for two personnel.
***Includes tests for sterility, mycoplasma, endotoxin, gram stain, viability and transduction efficiency.

This is significantly lower than estimates of direct costs for the same process under GMP infrastructure ($38,813 U.S) (Abou-El-Enein, et al., *Cytotherapy* 15, 362-383 (2013)). Beyond the cost of obtaining initial cell products, the CD34+ cell selection reagents, concentrated LV vector and recombinant human growth factors are the most expensive components in this process, regardless of manufacturing infrastructure. Still, a benefit-to-cost ratio should be considered for each gene therapy candidate disease. For HIV+ patients, whose lifetime cost of care is estimated to be $600,000 U.S. (Schackman, et al., *Med Care* 44, 990-997 (2006)), a cell-based curative therapy would greatly reduce this economic burden; however, the majority of HIV+ patients do not reside in countries with established cGMP manufacturing facilities.

In summary, this study establishes the proof-of-principle for small footprint, semi-automated, mostly closed manufacturing of LV gene-modified CD34+ cells for therapeutic use with the CliniMACS Prodigy™ device. The point-of-care and/or portable delivery, safety and engraftment of these cells in a preclinical xenotransplantation model as well as a clinically relevant large animal model is demonstrated. This work represents the first significant advance in global distribution of LV-mediated hematopoietic stem cell gene therapy.

Example 2

Exemplary Protocol/Semi-Automated. Benchtop Manufacturing of Lentivirus Gene Modified Nonhuman Primate Bone Marrow-Derived CD34+ Hematopoietic Stem and Progenitor Cells Using the Prodigy CliniMACS Closed System Cell Processing Device Reagents and Materials. TS100 CliniMACS Prodigy tubing set; TS730 CliniMACS Prodigy tubing set; Plasmalyte A or other saline solution for intravenous infusion; 25% Human Serum Albumin (HSA); 6% Hetastarch in saline (HES); CliniMACS Buffer (e.g. PBS/EDTA) or other buffer; Biotinylated Anti-CD34 antibody (clone 12.8) (herein referred to as 12.8 antibody); Streptavidin-coated microbeads; Autologous serum or other blocking agent; Funneled cryobag; Needle-less spike adapter; 60 mL syringe; 30 mL syringe; Complete Transduction Media; and Concentrated Lentivirus.

Equipment. Prodigy CliniMACS device (Miltenyi Biotec); in this Example referred to as "the device". The device must be equipped with software programs disclosed herein, and $CO_2$ and compressed air regulated connections per manufacturer specifications. Biosafety cabinet equipped with laminar air flow; sterile tubing welder; automated blood cell analyzer and refrigerator (2-8° C.) and freezer (−20° C.).

Protocol. Device-based processing is divided into a total of seven custom programs outlined elsewhere herein.

Step/Note. Bone marrow should be harvested in an operating/procedure room per veterinary standard practice guidelines at the resident institution.
  Sub-Step/Note. Harvested marrow should be passed through a filter set and diluted in ACD and heparin to prevent coagulation.
  Sub-Step/Note. If transport is required, transfer bone marrow product at room temperature in a controlled temperature container labeled as a biohazard and exempt human specimen.
Step/Note. Note the starting volume of the bone marrow product to be processed.
Step/Note. Collect a sample of the starting marrow product for in-process testing.
Step/Note. Perform a complete blood cell count and differential on the starting bone marrow product.
Step/Note. For red blood cell (RBC) removal, dilute the starting bone marrow product with Plasmalyte A to a total hematocrit (HCT) of 25%.
  Sub-Step/Note. Add Plasmalyte A to the bone marrow product bag in a biosafety cabinet and mix well.
  Sub-Step/Note. Note the volume of diluted bone marrow product.
Step/Note. Prepare a 3L of CliniMACS PBS/EDTA buffer by adding 60 mL of 25% HSA in a biosafety cabinet and mix well.
Step/Note. Open the TS100 tubing set packaging and locate tubing labeled "V5" and "V7" for valves 5 and 7, respectively.
Step/Note. Sterile weld a funneled cryobag to the tubing set at V5.
  Sub-Step/Note. Choose a bag volume appropriate for the volume of sedimentation.
  Sub-Step/Note. Remove tubing clamp during sterile weld.
  Sub-Step/Note. Be sure to leave sufficient tubing between the weld and the junction to prevent the weld from being pinched in V5.
Step/Note. Sterilize the female end of the needle-less spike adapter and attach to tubing set at V7 using available luer connection.
Step/Note. Insert needle-less spike adapter at V7 into a sterile port on the bag of HES. Step/Note. Attach diluted bone marrow product to the product application bag on the tubing set.
  Sub-Step/Note. For diluted bone marrow volumes 60 mL, use a 60 mL syringe to inject diluted bone marrow product into product application bag via luer connector.
  Sub-Step/Note. For diluted bone marrow volumes >60 mL, sterile weld or spike bone marrow product bag into upper port on product application bag.
Step/Note. Power on the Prodigy CliniMACS device.
Step/Note. Select "User Programs" and choose the program J1.
Step/Note. Run the program to begin installing the TS100 tubing set per device instructions.
  Sub-Step/Note. Follow prompts to install a new TS100 tubing set.
Step/Note. Manually enter the volume of diluted bone marrow product when prompted by the device.
Step/Note. Manually enter the % HCT value of 25%.
Step/Note. Manually enter the number of stages required to load the product into the tubing set for sedimentation.
  Sub-Step/Note. To determine the number of stages required divide the diluted bone marrow volume in mL by 300 mL per stage and round up to the next whole number.
Step/Note. When prompted by the device to ensure appropriate tubing set connections for HES and CliniMACS PBS/EDTA Buffer, verify connections and answer "yes".
Step/Note. When prompted by the device to ensure appropriate tubing set connections for sedimentation bags, verify connections and answer "yes".
  Sub-Step/Note. Device will automatically begin the processing program for RBC sedimentation.
Step/Note. Once the device has started the automated part of the program, there is no user manipulation required until the end of the 30-minute sedimentation period.
  Sub-Step/Note. When prompted by the device whether ready to begin RBC removal, answer "Yes" to begin RBC removal if sedimentation is complete. Answer "No" and restart the sedimentation wait period, if additional sedimentation is required.
  Sub-Step/Note. Wait an additional 10-30 minutes for sedimentation to complete.
  Sub-Step/Note. At the desired sedimentation time, press "OK".
  Sub-Step/Note. Answer "Yes" to continue to RBC removal.
Step/Note. Enter an initial volume (mL) to remove from the RBC sediment layer. The target removal volume should not disturb the white blood cell pellet on top of the RBC layer but should retain 30 mL RBC sediment volume.
  Sub-Step/Note. Any number of volumes can be removed to achieve this goal provided the initial volume of RBC sediment removed does not exceed the available volume in the sedimentation bag.
  Sub-Step/Note. To remove additional volumes of RBC sediment, answer "yes" when prompted by the device to continue with RBC removal and then enter the desired volume (mL) to remove.
Step/Note. Once a satisfactory level of RBC removal has been achieved, answer "no" when prompted by the device to continue with RBC removal.
Step/Note. Answer "yes" when prompted by the device whether you are sure you are done with RBC removal and want to continue with the program.
Step/Note. The device will continue the program until completion and will automatically stop and save the program details once completed.
  Sub-Step/Note. The RBC depleted fraction will be in the device chamber at the end of the program.
Step/Note. Select and run the "Chamber Out" program found on the Tools menu.

Sub-Step/Note. Attach a female-female luer coupler to each of the two tubes connected to the chamber on the tubing set.

Sub-Step/Note. Use the luer caps from the fitting to cap the chamber ports prior to removal.

Sub-Step/Note. Transfer the capped chamber to the biosafety cabinet.

Step/Note. In a biosafety cabinet, attach a 60 mL syringe to the top port of the chamber.

Step/Note. Gently tilt the chamber to pool RBC depleted cell suspension over the aspiration ports and withdraw the syringe plunger slowly to transfer all of the RBC depleted cell suspension into the syringe.

Step/Note. Note the volume of the RBC depleted cell suspension.

Step/Note. Withdraw a sample for yield testing and perform a complete blood cell count with differential.

Step/Note. Calculate the required volumes of 12.8 antibody and streptavidin microbeads necessary to efficiently label the RBC depleted cell fraction.

Step/Note. Transfer the calculated volume of 12.8 antibody and autologous serum to a final volume of 1 mL into a 10 mL syringe and withdraw the plunger to add 9 mL of air to the syringe. Label the syringe.

Step/Note. Transfer the calculated volume of streptavidin-coated microbeads to a separate 10 mL syringe and withdraw the plunger to add air up to a 10 mL final volume.

Step/Note. Sterile cap and label both syringes for transfer to the device.

Step/Note. At the device, under User Programs select the program J3.
  Sub-Step/Note. Sterile connect the syringes containing 12.8 antibody/autoserum and streptavidin microbeads where prompted.
  Sub-Step/Note. When prompted to verify tubing connections by the device, verify connections are correct and press "yes".
  Sub-Step/Note. Device will automatically begin program.
  Sub-Step/Note. Total program run time is 45 minutes.

Step/Note. The device will continue the program until completion and will automatically stop and save the program details once completed.
  Sub-Step/Note. The CD34 labeled fraction will be in the device chamber at the end of the program.

Step/Note. At the device, under User Programs select the program J4.
  Sub-Step/Note. Run program per device instructions.
  Sub-Step/Note. Device will automatically begin program.
  Sub-Step/Note. Total program run time is 45 minutes.

Step/Note. The device will continue the program until completion and will automatically stop and save the program details once completed.
  Sub-Step/Note. The CD34 enriched cell fraction will be in the "Target Cell Bag" at the end of the program.
  Sub-Step/Note. The CD34 depleted fraction will be in the bag labeled "Negative Fraction" at the end of the program.

Step/Note. Remove the Target Cell Bag from the device tubing set by heat sealing the tubing immediately above the adjacent luer connection.

Step/Note. Transfer the Target Cell Bag to the biosafety cabinet and remove a 0.5 mL sample for to determine cell yield. The final volume is 45 mL.

Step/Note. Remove the TS100 tubing set from the device by opening the "Tools" menu and selecting the "TS Removal" program.

Sub-Step/Note. Make certain all tubing valves are closed and heat seal any tubing leading to fluid bags prior to program initiation.

Sub-Step/Note. Run the program following device prompts until completion.

Step/Note. Prepare TS730 tubing set by connecting a needle-free spike to luer fitting on tubing at Valve 4 (V4).

Step/Note. Spike V4 tubing into bag containing Complete Transduction Media for hematopoietic stem cells.

*Step/Note. Draw required volume of Concentrated Lentivirus into an appropriately sized syringe and connect to luer fitting on tubing at Valve 5 (V5).

**Step/Note. Remove standard Target Cell Bag from tubing set.

Step/Note. Connect Target Cell Bag from TS100 tubing set containing CD34 enriched cell fraction to tubing set in place of standard Target Cell Bag.

Step/Note. Select the program J6 from the User Programs menu and hit "run".

Step/Note. Follow device prompts to install TS730 tubing set making sure to hang Target Cell Bag containing enriched fraction upside down for draining.

Step/Note. When prompted to verify tubing connections by the device, verify connections are correct and press "yes".
  Sub-Step/Note. Device will automatically begin program.
  Sub-Step/Note. Total program run time is 57 minutes.

Step/Note. The device will continue the program until completion and will automatically stop and save the program details once completed.
  Sub-Step/Note. OPTIONAL: After device adds Concentrated Lentivirus to cells chamber will begin a 30 minute slow speed centrifugation (termed "spinoculation"). Terminate spinoculation by pressing "OK" to stop centrifugation and then "yes" to abort program.
  Sub-Step/Note. The CD34 enriched cell fraction and Lentivirus Vector for transduction will be in the device chamber at the end of the program.

Step/Note. Select the program J8 from the User Programs menu and hit "run".
  Sub-Step/Note. Device will automatically begin program.
  Sub-Step/Note. Total program run time is flexible.

Step/Note. The device will continue the program until the user aborts the program by pressing "OK" and then "yes" to confirm program abort command. The device will then save the program details once completed.

Step/Note. OPTIONAL: In biosafety cabinet draw a second aliquot of required volume of Concentrated Lentivirus into an appropriately sized syringe and connect to luer fitting on tubing at Valve 5 (V5).
  Sub-Step/Note. Select program J7 from the User Programs menu and hit "run".
  Sub-Step/Note. The device will automatically begin the program.
  Sub-Step/Note. Total program run time is 5 minutes.
  Sub-Step/Note. The program will run to completion and will automatically stop and save program details.
  Sub-Step/Note. Re-initiate J8 program per steps *, ** above following completion of J7 program.

Step/Note. In preparation for harvest, spike a needle-free spike adapter into a 1L bag of Plasmalyte A buffer connected to a second 1L bag of Plasmalyte A.

Step/Note. Replace Complete Transduction Media on V4 with Plasmalyte A via needle-free spike luer.

Step/Note. Inject 60 mL of Plasmalyte A into a 400 mL cryobag in a biosafety cabinet.

Step/Note. Replace Target Cell Bag on TS730 with cryobag containing Plasmalyte A.

Step/Note. Manually open valve pathway from cryobag to waste bag to allow Plasmalyte A to drain through tubing.
Step/Note. To harvest the transduced cell product for infusion, select program J9 from the User Programs menu and hit "run".
Step/Note. When prompted to verify tubing connections by the device, verify connections are correct and press "yes".
Sub-Step/Note. Device will automatically begin program.
Sub-Step/Note. Total program run time is 50 minutes.
Step/Note. The device will continue the program until completion and will automatically stop and save the program details once completed.
Step/Note. Final cell product for release testing and infusion will be in cryobag at Valve 22.

Example 3

Exemplary Protocol/Semi-Automated. Benchtop Manufacturing of Lentivirus Gene Modified Human Bone Marrow-Derived CD34+ Hematopoietic Stem and Progenitor Cells Using the Prodigy CliniMACS Closed System Cell Processing Device Reagents and Materials. TS100 CliniMACS Prodigy tubing set; TS730 CliniMACS Prodigy tubing set; Plasmalyte A or other saline solution for intravenous infusion; 25% Human Serum Albumin (HSA); 6% Hetastarch in saline (HES); CliniMACS PBS/EDTA Buffer or other PBS/EDTA buffer; CliniMACS CD34 Microbeads or other direct-conjugate antibody-magnetic bead complex; GAMMAGARD (IVIg) or other blocking agent; Funneled cryobag; Needle-less spike adapter; 60 mL syringe; 30 mL syringe; Complete Transduction Media; and Concentrated Lentivirus.

Equipment. Prodigy CliniMACS device (Miltenyi Biotec); in this Example referred to as "the device". The device must be equipped with $CO_2$ and compressed air regulated connections per manufacturer specifications. Biosafety cabinet equipped with laminar air flow; sterile tubing welder; automated blood cell analyzer.

Protocol. Device-based processing is divided into a total of seven custom programs described elsewhere herein.
Step/Note. Bone marrow should be harvested in an operating room per clinical standard practice guidelines at the resident institution.
Sub-Step/Note. Harvested marrow should be passed through a filter set and diluted in ACD and heparin to prevent coagulation.
Sub-Step/Note. If transport is required, transfer bone marrow product at room temperature in a controlled temperature container labeled as a biohazard and exempt human specimen.
Step/Note. Note the starting volume of the bone marrow product to be processed.
Step/Note. Collect a sample of the starting marrow product for in-process testing.
Step/Note. Perform a complete blood cell count and differential on the starting bone marrow product.
Step/Note. For red blood cell (RBC) removal, dilute the starting bone marrow product with Plasmalyte A to a total hematocrit (HCT) of 25%.
Sub-Step/Note. Add Plasmalyte A to the bone marrow product bag in a biosafety cabinet and mix well.
Sub-Step/Note. Note the volume of diluted bone marrow product.
Step/Note. Prepare a 3L of CliniMACS PBS/EDTA buffer by adding 60 mL of 25% HSA in a biosafety cabinet and mix well.
Step/Note. Open the TS100 tubing set packaging and locate tubing labeled "V5" and "V7" for valves 5 and 7, respectively.
Step/Note. Sterile weld a funneled cryobag to the tubing set at V5.
Sub-Step/Note. Choose a bag volume appropriate for the volume of sedimentation.
Sub-Step/Note. Remove tubing clamp during sterile weld.
Sub-Step/Note. Be sure to leave sufficient tubing between the weld and the junction to prevent the weld from being pinched in V5.
Step/Note. Sterilize the female end of the needle-less spike adapter and attach to tubing set at V7 using available luer connection.
Step/Note. Insert needle-less spike adapter at V7 into a sterile port on the bag of HES.
Step/Note. Attach diluted bone marrow product to the product application bag on the tubing set.
Sub-Step/Note. For diluted bone marrow volumes ≤60 mL, use a 60 mL syringe to inject diluted bone marrow product into product application bag via luer connector.
Sub-Step/Note. For diluted bone marrow volumes >60 mL, sterile weld or spike bone marrow product bag into upper port on product application bag.
Step/Note. Power on the Prodigy CliniMACS device.
Step/Note. Select "User Programs" and choose the program J1.
Step/Note. Run the program to begin installing the TS100 tubing set per device instructions.
Sub-Step/Note. Follow prompts to install a new TS100 tubing set.
Step/Note. Manually enter the volume of diluted bone marrow product when prompted by the device.
Step/Note. Manually enter the % HCT value of 25%.
Step/Note. Manually enter the number of stages required to load the product into the tubing set for sedimentation.
Sub-Step/Note. To determine the number of stages required divide the diluted bone marrow volume in mL by 300 mL per stage and round up to the next whole number.
Step/Note. When prompted by the device to ensure appropriate tubing set connections for HES and CliniMACS PBS/EDTA Buffer, verify connections and answer "yes".
Step/Note. When prompted by the device to ensure appropriate tubing set connections for sedimentation bags, verify connections and answer "yes".
Sub-Step/Note. Device will automatically begin the processing program for RBC sedimentation.
Step/Note. Once the device has started the automated part of the program, there is no user manipulation required until the end of the 30-minute sedimentation period.
Sub-Step/Note. When prompted by the device whether ready to begin RBC removal, answer "Yes" to begin RBC removal if sedimentation is complete. Answer "No" and restart the sedimentation wait period, if additional sedimentation is required.
Sub-Step/Note. Wait an additional 10-30 minutes for sedimentation to complete.
Sub-Step/Note. At the desired sedimentation time, press "OK".
Sub-Step/Note. Answer "Yes" to continue to RBC removal.
Step/Note. Enter an initial volume (mL) to remove from the RBC sediment layer. The target removal volume should not disturb the white blood cell pellet on top of the RBC layer but should retain 30 mL RBC sediment volume.

Sub-Step/Note. Any number of volumes can be removed to achieve this goal provided the initial volume of RBC sediment removed does not exceed the available volume in the sedimentation bag.

Sub-Step/Note. To remove additional volumes of RBC sediment, answer "yes" when prompted by the device to continue with RBC removal and then enter the desired volume (mL) to remove.

Step/Note. Once a satisfactory level of RBC removal has been achieved, answer "no" when prompted by the device to continue with RBC removal.

Step/Note. Answer "yes" when prompted by the device whether you are sure you are done with RBC removal and want to continue with the program.

Step/Note. The device will continue the program until completion and will automatically stop and save the program details once completed.

Sub-Step/Note. The RBC depleted fraction will be in the device chamber at the end of the program.

Step/Note. In a biosafety cabinet, transfer one vial (7.5 mL) of CliniMACS CD34 Microbeads and 3 mL of GAMMAGARD (IVIg) into a 30 mL syringe and withdraw the plunger to add 19.5 mL of air to the syringe.

Step/Note. Sterile cap the syringe for transfer to the device.

Step/Note. At the device, under User Programs select the program named "J2".

Sub-Step/Note. Sterile connect the syringe containing CliniMACS CD34 Microbeads and GAMMAGARD (IVIg) where prompted.

Sub-Step/Note. When prompted to verify tubing connections by the device, verify connections are correct and press "yes".

Sub-Step/Note. Device will automatically begin program.

Sub-Step/Note. Total program run time is 45 minutes.

Step/Note. The device will continue the program until completion and will automatically stop and save the program details once completed.

Sub-Step/Note. The CD34 labeled fraction will be in the device chamber at the end of the program.

Step/Note. At the device, under User Programs select the program J4.

Sub-Step/Note. Run program per device instructions.

Sub-Step/Note. Device will automatically begin program.

Sub-Step/Note. Total program run time is 45 minutes.

Step/Note. The device will continue the program until completion and will automatically stop and save the program details once completed.

Sub-Step/Note. The CD34 enriched cell fraction will be in the "Target Cell Bag" at the end of the program.

Sub-Step/Note. The CD34 depleted fraction will be in the bag labeled "Negative Fraction" at the end of the program.

Step/Note. Remove the Target Cell Bag from the device tubing set by heat sealing the tubing immediately above the adjacent luer connection.

Step/Note. Transfer the Target Cell Bag to the biosafety cabinet and remove a 0.5 mL sample for to determine cell yield. The final volume is 45 mL.

Step/Note. Remove the TS100 tubing set from the device by opening the "Tools" menu and selecting the "TS Removal" program.

Sub-Step/Note. Make certain all tubing valves are closed and heat seal any tubing leading to fluid bags prior to program initiation.

Sub-Step/Note. Run the program following device prompts until completion.

Step/Note. Prepare TS730 tubing set by connecting a needle-free spike to luer fitting on tubing at Valve 4 (V4).

Step/Note. Spike V4 tubing into bag containing Complete Transduction Media for hematopoietic stem cells.

Step/Note. Draw required volume of Concentrated Lentivirus into an appropriately sized syringe and connect to luer fitting on tubing at Valve 5 (V5).

Step/Note. Remove standard Target Cell Bag from tubing set.

Step/Note. Connect Target Cell Bag from TS100 tubing set containing CD34 enriched cell fraction to tubing set in place of standard Target Cell Bag.

Step/Note. Select the program J6 from the User Programs menu and hit "run".

Step/Note. Follow device prompts to install TS730 tubing set making sure to hang Target Cell Bag containing enriched fraction upside down for draining.

Step/Note. When prompted to verify tubing connections by the device, verify connections are correct and press "yes".

Sub-Step/Note. Device will automatically begin program.

Sub-Step/Note. Total program run time is 57 minutes.

Step/Note. The device will continue the program until completion and will automatically stop and save the program details once completed.

Sub-Step/Note. OPTIONAL: After device adds Concentrated Lentivirus to cells chamber will begin a 30 minute slow speed centrifugation (termed "spinoculation"). Terminate spinoculation by pressing "OK" to stop centrifugation and then "yes" to abort program.

Sub-Step/Note. The CD34 enriched cell fraction and Lentivirus Vector for transduction will be in the device chamber at the end of the program.

*Step/Note. Select the program J8 from the User Programs menu and hit "run".

Sub-Step/Note. Device will automatically begin program.

Sub-Step/Note. Total program run time is flexible.

**Step/Note. The device will continue the program until the user aborts the program by pressing "OK" and then "yes" to confirm program abort command. The device will then save the program details once completed.

Step/Note. OPTIONAL: In biosafety cabinet draw a second aliquot of required volume of Concentrated Lentivirus into an appropriately sized syringe and connect to luer fitting on tubing at Valve 5 (V5).

Sub-Step/Note. Select program J7 from the User Programs menu and hit "run".

Sub-Step/Note. The device will automatically begin the program.

Sub-Step/Note. Total program run time is 5 minutes.

Sub-Step/Note. The program will run to completion and will automatically stop and save program details.

Sub-Step/Note. Re-initiate J8 program per *, ** above following completion of J7 program.

Step/Note. In preparation for harvest, spike a needle-free spike adapter into a 1L bag of Plasmalyte A buffer connected to a second 1L bag of Plasmalyte A.

Step/Note. Replace Complete Transduction Media on V4 with Plasmalyte A via needle-free spike luer.

Step/Note. Inject 60 mL of Plasmalyte A into a 400 mL cryobag in a biosafety cabinet.

Step/Note. Replace Target Cell Bag on TS730 with cryobag containing Plasmalyte A.

Step/Note. Manually open valve pathway from cryobag to waste bag to allow Plasmalyte A to drain through tubing.

Step/Note. To harvest the transduced cell product for infusion, select program J9 from the User Programs menu and hit "run".

Step/Note. When prompted to verify tubing connections by the device, verify connections are correct and press "yes".
  Sub-Step/Note. Device will automatically begin program.
  Sub-Step/Note. Total program run time is 50 minutes.
Step/Note. The device will continue the program until completion and will automatically stop and save the program details once completed.
Step/Note. Final cell product for release testing and infusion will be in cryobag at Valve 22.

Example 4

Exemplary Protocol/Semi-Automated. Benchtop Manufacturing of Lentivirus Gene Modified HUMAN Leukapheresis-Derived CD34+ Hematopoietic Stem and Progenitor Cells Using the Prodigy CliniMACS Closed System Cell Processing Device Reagents and Materials. TS100 CliniMACS Prodigy tubing set; TS730 CliniMACS Prodigy tubing set; Plasmalyte A or other saline solution for intravenous infusion; 25% Human Serum Albumin (HSA); CliniMACS PBS/EDTA Buffer or other PBS/EDTA buffer; CliniMACS CD34 Microbeads or other direct-conjugate antibody-magnetic bead complex; GAMMAGARD (IVIg) or other blocking agent; Funneled cryobag; Needle-less spike adapter; 60 mL syringe; 30 mL syringe; Complete Transduction Media; Concentrated Lentivirus.

Equipment. Prodigy CliniMACS device (Miltenyi Biotec); in this Example referred to as "the device". The device must be equipped with $CO_2$ and compressed air regulated connections per manufacturer specifications. Biosafety cabinet equipped with laminar air flow; Sterile tubing welder; automated blood cell analyzer; and bag press (if starting product is >270 mL initial volume).

Protocol. Device-based processing is divided into a total of five custom programs which are described elsewhere herein.

Step/Note. Leukapheresis should be performed per clinical standard practice guidelines at the resident institution.
  Sub-Step/Note. If transport is required, transfer bone marrow product at room temperature in a controlled temperature container labeled as a biohazard and exempt human specimen.
Step/Note. Note the starting volume of the apheresis product to be processed. If the starting product volume is <270 mL, proceed to *** below.
Step/Note. If the starting product volume is ≤270 mL:
  Sub-Step/Note. Dilute the starting bone marrow product with Plasmalyte A to maximum product bag capacity.
  Sub-Step/Note. Centrifuge the product bag with no brake to pellet cells.
  Sub-Step/Note. Use a bag press to reduce total volume of product bag containing cell pellet to ≤200 mL.
***Step/Note. Collect a sample of the starting apheresis product for in-process testing.
Step/Note. Perform a complete blood cell count and differential on the starting apheresis product.
  Sub-Step/Note. Note the hematocrit (HCT) content of the product.
  Sub-Step/Note. If starting HCT content is >25%, add a sufficient volume of Plasmalyte A to reduce HCT content to ≤25%.
  Sub-Step/Note. Add Plasmalyte A to the bone marrow product bag in a biosafety cabinet and mix well.
  Sub-Step/Note. Note the diluted product volume.
    Sub-Step/Note. If diluted product volume is ≥270 mL, go to * above.
    Sub-Step/Note. If diluted product volume is <270 mL proceed to step ** below.
Step/Note. Prepare a 3L of CliniMACS PBS/EDTA buffer by adding 60 mL of 25% HSA in a biosafety cabinet and mix well.
**Step/Note. In a biosafety cabinet, transfer one vial (7.5 mL) of CliniMACS CD34 Microbeads and 3 mL of GAMMAGARD (IVIg) into a 30 mL syringe and withdraw the plunger to add 19.5 mL of air to the syringe.
Step/Note. Open the TS100 tubing set packaging and transfer into the biosafety cabinet.
Step/Note. Attach the CliniMACS PBS/EDTA buffer containing HSA to tubing spike at Valve 4 (V4).
Step/Note. Attach the syringe containing microbeads and IVIg to the tubing set at Valve 5 (V5) via the luer connection provided.
Step/Note. Attach apheresis product to the product application bag at Valve 8 (V8) on the tubing set.
Step/Note. Power on the Prodigy CliniMACS device.
Step/Note. Select "User Programs" and choose the program J5.
Step/Note. Run the program to begin installing the TS100 tubing set per device instructions.
  Sub-Step/Note. Follow prompts to install a new TS100 tubing set.
Step/Note. Manually enter the volume of apheresis product when prompted by the device.
Step/Note. Manually enter the % HCT value of 25%.
Step/Note. When prompted by the device to ensure appropriate tubing set connections, verify connections and answer "yes".
  Sub-Step/Note. Device will automatically begin the processing program for preparation, CD34 labeling and magnetic column selection.
Step/Note. Once the device has started the automated part of the program, there is no user manipulation required. The program run time is 75 minutes.
Step/Note. The device will continue the program until completion and will automatically stop and save the program details once completed.
  Sub-Step/Note. The CD34 enriched cell fraction will be in the "Target Cell Bag" at the end of the program.
  Sub-Step/Note. The CD34 depleted fraction will be in the bag labeled "Negative Fraction" at the end of the program.
Step/Note. Remove the Target Cell Bag from the device tubing set by heat sealing the tubing immediately above the adjacent luer connection.
Step/Note. Transfer the Target Cell Bag to the biosafety cabinet and remove a 0.5 mL sample for to determine cell yield. The final volume is 45 mL.
Step/Note. Remove the TS100 tubing set from the device by opening the "Tools" menu and selecting the "TS Removal" program.
  Make certain all tubing valves are closed and heat seal any tubing leading to fluid bags prior to program initiation.
  Run the program following device prompts until completion.
Step/Note. Prepare TS730 tubing set by connecting a needle-free spike to luer fitting on tubing at Valve 4 (V4).
Step/Note. Spike V4 tubing into bag containing Complete Transduction Media for hematopoietic stem cells.
Step/Note. Draw required volume of Concentrated Lentivirus into an appropriately sized syringe and connect to luer fitting on tubing at Valve 5 (V5).

Step/Note. Remove standard Target Cell Bag from tubing set.
Step/Note. Connect Target Cell Bag from TS100 tubing set containing CD34 enriched cell fraction to tubing set in place of standard Target Cell Bag.
Step/Note. Select the program J6 from the User Programs menu and hit "run".
Step/Note. Follow device prompts to install TS730 tubing set making sure to hang Target Cell Bag containing enriched fraction upside down for draining.
Step/Note. When prompted to verify tubing connections by the device, verify connections are correct and press "yes".
Sub-Step/Note. Device will automatically begin program.
Sub-Step/Note. Total program run time is 57 minutes.
Step/Note. The device will continue the program until completion and will automatically stop and save the program details once completed.
Sub-Step/Note. OPTIONAL: After device adds Concentrated Lentivirus to cells chamber will begin a 30 minute slow speed centrifugation (termed "spinoculation"). Terminate spinoculation by pressing "OK" to stop centrifugation and then "yes" to abort program.
Sub-Step/Note. The CD34 enriched cell fraction and Lentivirus Vector for transduction will be in the device chamber at the end of the program.
Step/Note. Select the program J8 from the User Programs menu and hit "run".
Sub-Step/Note. Device will automatically begin program.
Sub-Step/Note. Total program run time is flexible.
Step/Note. The device will continue the program until the user aborts the program by pressing "OK" and then "yes" to confirm program abort command. The device will then save the program details once completed.
Step/Note. OPTIONAL: In biosafety cabinet draw a second aliquot of required volume of Concentrated Lentivirus into an appropriately sized syringe and connect to luer fitting on tubing at Valve 5 (V5).
Sub-Step/Note. Select program J7 from the User Programs menu and hit "run".
Sub-Step/Note. The device will automatically begin the program.
Sub-Step/Note. Total program run time is 5 minutes.
Sub-Step/Note. The program will run to completion and will automatically stop and save program details.
Sub-Step/Note. Re-initiate J8 program per above following completion of J7 program.
Step/Note. In preparation for purification/formulation, spike a needle-free spike adapter into a 1L bag of Plasmalyte A buffer connected to a second 1L bag of Plasmalyte A.
Step/Note. Replace Complete Transduction Media on V4 with Plasmalyte A via needle-free spike luer.
Step/Note. Inject 60 mL of Plasmalyte A into a 400 mL cryobag in a biosafety cabinet.
Step/Note. Replace Target Cell Bag on TS730 with cryobag containing Plasmalyte A.
Step/Note. Manually open valve pathway from cryobag to waste bag to allow Plasmalyte A to drain through tubing.
Step/Note. To purify/formulate the transduced cell product for infusion, select program J9 from the User Programs menu and hit "run".
Step/Note. When prompted to verify tubing connections by the device, verify connections are correct and press "yes".
Sub-Step/Note. Device will automatically begin program.
Sub-Step/Note. Total program run time is 50 minutes.
Step/Note. The device will continue the program until completion and will automatically stop and save the program details once completed.
Step/Note. Final cell product for release testing and infusion will be in cryobag at Valve 22.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the isolation, genetic modification, purification and formulation of cells from a subject sample.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention can be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method performed by a device, the method comprising:
   receiving, by a treatment chamber, a subject sample
   transferring, by at least one valve and at least one pump, the subject sample from the treatment chamber to at least one target cell selector;
   separating, by the at least one target cell selector, target cells from non-target cells in the subject sample by allowing the non-target cells to pass into a waste bag and retaining the target cells within the at least one target cell selector;
   transferring, by the at least one valve and the at least one pump, the target cells into the treatment chamber;
   introducing a genetic modifier to the target cells to generate genetically-modified target cells;
   pelleting the genetically-modified target cells within the treatment chamber through centrifugation to create a pelleted cell suspension;
   removing a specified supernatant volume from the pelleted cell suspension in the treatment chamber through a first tubing set connected to the treatment chamber;
   diluting the pelleted cell suspension with final formulation media comprising a pharmaceutically acceptable carrier;
   centrifuging the diluted pelleted cell suspension and removing an additional volume of supernatant in the treatment chamber through the first tubing set to form a final cell product formulation; and
   transferring the final cell product formulation into one or more cryobags through a second tubing set connected to the treatment chamber wherein the final cell product formulation is ready for administration to a subject upon completion of transfer into the one or more cryobags.

2. The method of claim 1 wherein a user of the device:
   determines an initial volume of the subject sample;
   determines a hematocrit level of the subject sample;
   determines a volume of buffer to add to the subject sample to reduce the hematocrit level to at least 25% according to the following formula:

$$\left(\frac{\text{starting product volume (mL)} \times \text{obtained hematocrit value (\%)}}{25\% \text{ desired hematocrit value}}\right) - \text{starting product volume (mL)};$$

and wherein the device adds, by the at least one valve and the at least one pump, the determined volume of buffer to the subject sample.

3. The method of claim 1 comprising performing release testing to verify compliance with Current Good Manufacturing Practices wherein the release testing comprises

| Test | Required Result |
| --- | --- |
| Gram Stain | Negative |
| 3 Day Sterility | Negative |
| 14 Day Sterility | Negative |
| Mycoplasma | Negative |
| Endotoxin | ≤0.5 EU/ml |
| Cell Viability by Trypan Blue Dye Exclusion | ≥70%. |

4. The method of claim 1 wherein the introducing of the genetic modifier inserts or alters a gene selected from ABCD1, ABCA3, ABLI, ADA, AKT1, APC, APP, ARSA, ARSB, BCL11A, BLC1, BLC6, BRCA1, BRCA2, BRIP1, C9ORF72, C46, CAR, CAS9, C-CAM, CBFAI, CBL, CCR5, CD4, CD19, CD40, CDA, CFTR, CLN3, C-MYC, CRE, CSCR4, CSFIR, CTLA, CTS-I, CYB5R3, DCC, DHFR, DKC1, DLL1, DMD, EGFR, ERBA, ERBB, EBRB2, ETSI, ETS2, ETV6, F8, F9, FANCA, FANCB, FANCC, FANCD2, FANCE, FANCF, FANCG, FANCI, FANCL, FANCM, FasL, FCC, FGR, FOX, FUS, FUSI, FYN, GALNS, GATA1, GLB1, GNS, GUSB, HBB, HBD, HBE1, HBG1, HBG2, HCR, HGSNAT, HOXB4, HRAS, HYAL1, ICAM-1, iCaspase, IDUA, IDS, JUN, KLF4, KRAS, LCK, LRRK2, LYN, MCC, MDM2, MGMT, MLL, MMACI, MYB, MEN-I, MEN-II, MYC, NAGLU, NANOG, NF-1, NF-2, NKX2.1, NOTCH, OCT4, p16, p21, p27, p53, p57, p73, PALB2, PARK2, PARK7, phox, PINK1, PK, PSEN1, PSEN2, PTPN22, RAD51C, ras, at least one of RPL3 through RPL40, RPLPO, RPLP1, RPLP2, at least one of RPS2 through RPS30, RPSA, SFTPB, SFTPC, SGSH, SLX4, SNCA, SOD1, SOX2, TERC, TERT, TDP43, TINF2, TK, ubiquilin 2, VHL, WAS and WT-I.

5. The method of claim 1 wherein the genetically-modified target cells are hematopoietic stem cells (HSC), hematopoietic progenitor cells (HPC), hematopoietic stem and progenitor cells (HSPC), T cells, natural killer cells, B cells, macrophages, monocytes, mesenchymal stem cells (MSC), white blood cells (WBC), mononuclear cells (MNC), endothelial cells (EC), stromal cells, and/or bone marrow fibroblasts.

6. The method of claim 1 wherein the genetically-modified target cells are CD34+HSPC.

7. The method of claim 1 wherein the genetic modifier comprises a lentiviral vector comprising a pseudotype envelope glycoprotein and a lentiviral RNA molecule wherein the pseudotype envelope glycoprotein comprises vesicular stomatitis virus glycoprotein (VSVG), cocal virus glycoprotein (cocal), the feline endogenous virus glycoprotein (RD114), or modified foamy virus glycoprotein (mFoamy) and wherein the lentiviral RNA molecule comprises a HIV-1-derived, self-inactivating lentivirus backbone which is integration deficient.

8. The method of claim 4 wherein the genetic modifier comprises a foamy viral vector comprising a pseudotype envelope glycoprotein and a foamy viral RNA molecule wherein the pseudotype envelope glycoprotein comprises foamy viral envelope protein (Foamy), or modified foamy viral envelope protein (mFoamy) and wherein the foamy viral RNA molecule comprises a self-inactivating foamy virus backbone which is integration deficient.

9. The method of claim 1 wherein the one or more cryobags are sterile-welded to the second tubing set.

10. The method of claim 1 comprising the treatment chamber receiving the subject sample in a number of stages wherein the number of stages is determined by a user of the device and is obtained by diluting the subject sample and dividing the diluted sample volume in mL by 300mL per stage and rounding up to the next whole number.

11. The method of claim 1 comprising the device receiving a signal that sedimentation is complete and red blood cell (RBC) removal may begin.

12. The method of claim 1 comprising the device receiving a signal determining an initial volume in mL to remove from a RBC sediment layer.

13. The method of claim 1 comprising receiving, by the at least one target cell selector beads or antibodies that selectively bind CD3, CD4, CD8, CD13, CD14, CD15, CD16, CD19, CD20, CD34, CD45, CD45RA, CD45RO, CD49f, CD50, CD56, CD71, CD90, or CD133.

14. The method of claim 1 comprising receiving, by the at least one target cell selector microbeads and intravenous immunoglobulin (IVIg).

15. The method of claim 1 comprising receiving, by the treatment chamber, transduction media wherein the transduction media comprises
(i) a base medium;
(ii) cyto- and/or chemokines comprising recombinant human granulocyte colony stimulating factor (G-CSF), stem cell factor (SCF), thrombopoietin (TPO), a flightless 3 ligand selected from flt3 or flt3L), and/or interleukins selected from interleukin 3 (IL-3) and/or interleukin 6 (IL-6); and
(iii) agents to promote cell survival and gene transfer comprising
(a) aryl-hydrocarbon receptor antagonists selected from StemRegenin-1 ; GNF351, and/or CH223191,
(b) pyrimidoindole derivatives selected from UM171, and/or UM118428,
(c) glucocorticoid receptor antagonists selected from mifepristone, RU-43044, Miconazole, 11-oxa cortisol, 11-oxa prednisolone, and/or dexamethasone mesylate;
(d) protamine sulfate,
(e) rapamycin,
(f) polybrene,
(g) fibronectin fragment,
(h) prostaglandin E2,
(i) antioxidants and/or
(j) nonsteroidal anti-inflammatory drugs selected from celecoxib, diclofenac, diflunisal, etodolac, ibuprofen, indomethacin, ketoprofen, nabumetone, naproxen, oxaprozin, piroxicam, salsalate, sulindac, and/or tolmetin.

16. The method of claim 1 comprising a user of the device drawing a first volume of Concentrated Lentivirus or foamy virus into an appropriately sized syringe and connecting the syringe to a luer fitting and drawing a second volume of Concentrated Lentivirus or foamy virus into an appropriately sized syringe and connecting the syringe to a luer fitting.

17. The method of claim 1 further comprising tagging, by the treatment chamber or the at least one target cell selector, target cells in the subject sample with immunomagnetic beads,
wherein separating the target cells from the non-target cells comprises retaining the immunomagnetic beads on a magnetically susceptible material,
wherein the magnetically susceptible material is disposed between a first electrode and a second electrode, and
wherein introducing the genetic modifier to the target cells comprises inducing pores in the target cells by activating an electric potential between the first electrode and the second electrode when the target cells are located in a chamber of the at least one target cell selector.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Lentivirus (LV)-specific forward primer

<400> SEQUENCE: 1
agagatgggt gcgagagcgt ca                                              22

<210> SEQ ID NO 2
<211> LENGTH: 24
<212> TYPE: DNA
<213> ORGANISM: Artificial Sequence
<220> FEATURE:
<223> OTHER INFORMATION: Lentivirus (LV)-specific reverse primer

<400> SEQUENCE: 2
tgccttggtg ggtgctactc ctaa                                            24

<210> SEQ ID NO 3
<211> LENGTH: 21
<212> TYPE: DNA
<213> ORGANISM: Artificial Sequence
<220> FEATURE:
<223> OTHER INFORMATION: Actin-specific forward primer designed for
      Pigtailed macaques (Macaca nemestrina)
```

<400> SEQUENCE: 3
tcctgtggca ctcacgaaac t                                              21

<210> SEQ ID NO 4
<211> LENGTH: 21
<212> TYPE: DNA
<213> ORGANISM: Artificial Sequence
<220> FEATURE:
<223> OTHER INFORMATION: Actin specific reverse primer designed for
      Pigtailed macaques (Macaca nemestrina)

<400> SEQUENCE: 4
gaagcatttg cggtggacga t                                              21

<210> SEQ ID NO 5
<211> LENGTH: 21
<212> TYPE: DNA
<213> ORGANISM: Artificial Sequence
<220> FEATURE:
<223> OTHER INFORMATION: Actin-Specific forward primer designed for
      homo sapiens

<400> SEQUENCE: 5
tcctgtggca tcgacgaaac t                                              21

<210> SEQ ID NO 6
<211> LENGTH: 21
<212> TYPE: DNA
<213> ORGANISM: Artificial Sequence
<220> FEATURE:
<223> OTHER INFORMATION: Actin-specific reverse primer designed for
      homo sapiens

<400> SEQUENCE: 6
gaagcatttg cggtggacga t                                              21

<210> SEQ ID NO 7
<211> LENGTH: 20
<212> TYPE: DNA
<213> ORGANISM: Artificial Sequence
<220> FEATURE:
<223> OTHER INFORMATION: Lentivirus (LV)-specific forward primer

<400> SEQUENCE: 7
tgaaagcgaa agggaaacca                                                20

<210> SEQ ID NO 8
<211> LENGTH: 15
<212> TYPE: DNA
<213> ORGANISM: Artificial Sequence
<220> FEATURE:
<223> OTHER INFORMATION: Lentivirus (LV)-specific reverse primer

<400> SEQUENCE: 8
ccgtgcgcgc ttcag                                                     15

<210> SEQ ID NO 9
<211> LENGTH: 24
<212> TYPE: DNA
<213> ORGANISM: Artificial Sequence
<220> FEATURE:
<223> OTHER INFORMATION: Probe

<400> SEQUENCE: 9
agctctctcg acgcaggact cggc                                           24

```
<210> SEQ ID NO 10
<211> LENGTH: 22
<212> TYPE: DNA
<213> ORGANISM: Artificial Sequence
<220> FEATURE:
<223> OTHER INFORMATION: a Beta-globin-specific forward primer

<400> SEQUENCE: 10
cctatcagaa agtggtggct gg                                              22

<210> SEQ ID NO 11
<211> LENGTH: 23
<212> TYPE: DNA
<213> ORGANISM: Artificial Sequence
<220> FEATURE:
<223> OTHER INFORMATION: a Beta-globin-specific reverse primer

<400> SEQUENCE: 11
ttggacagca agaaagtgag ctt                                             23

<210> SEQ ID NO 12
<211> LENGTH: 25
<212> TYPE: DNA
<213> ORGANISM: Artificial Sequence
<220> FEATURE:
<223> OTHER INFORMATION: Probe

<400> SEQUENCE: 12
tggctaatgc cctggcccac aagta                                           25
```